US010118880B2

(12) United States Patent
Sanz Yague et al.

(10) Patent No.: US 10,118,880 B2
(45) Date of Patent: Nov. 6, 2018

(54) PROCESS FOR THE PREPARATION OF HIGHER ALCOHOLS FROM ETHANOL AND N-HEXANOL BY GUERBET CONDENSATION

(71) Applicant: Abengoa Bioenergia Nuevas Tecnologias, S.A., Seville (ES)

(72) Inventors: Juan Luis Sanz Yague, Seville (ES); Francisco Antonio Ladrón De Guevara Vidal, Seville (ES); Laura Sánchez Holgado, Seville (ES); Yolanda Peña Gómez, Seville (ES); Carmen Maria Reyes Valle, Seville (ES); Ana Rosa Sánchez Sánchez, Seville (ES)

(73) Assignee: Abengoa Bioenergia Nuevas Tecnologies, S.A., Seville (ES)

( * ) Notice: Subject to any disclaimer, the term of this patent is extended or adjusted under 35 U.S.C. 154(b) by 0 days.

(21) Appl. No.: 15/526,124

(22) PCT Filed: Nov. 13, 2015

(86) PCT No.: PCT/IB2015/002217
§ 371 (c)(1),
(2) Date: May 11, 2017

(87) PCT Pub. No.: WO2016/075531
PCT Pub. Date: May 19, 2016

(65) Prior Publication Data
US 2017/0327445 A1    Nov. 16, 2017

(30) Foreign Application Priority Data

Nov. 14, 2014  (ES) .................................. 201431667
Nov. 14, 2014  (ES) .................................. 201431669

(51) Int. Cl.
| | | |
|---|---|---|
| C07C 29/34 | (2006.01) |
| C07C 29/80 | (2006.01) |
| B01J 21/00 | (2006.01) |
| B01J 21/10 | (2006.01) |
| B01J 37/03 | (2006.01) |
| B01J 37/06 | (2006.01) |
| B01J 37/02 | (2006.01) |
| B01J 23/44 | (2006.01) |
| B01J 37/08 | (2006.01) |
| B01J 37/18 | (2006.01) |
| B01J 23/648 | (2006.01) |

(Continued)

(52) U.S. Cl.
CPC ............. *C07C 29/34* (2013.01); *B01D 3/009* (2013.01); *B01D 3/143* (2013.01); *B01J 8/0278* (2013.01); *B01J 21/10* (2013.01); *B01J 23/08* (2013.01); *B01J 23/44* (2013.01); *B01J 23/62* (2013.01); *B01J 23/6482* (2013.01); *B01J 23/72* (2013.01); *B01J 23/898* (2013.01); *B01J 37/0213* (2013.01); *B01J 37/0236* (2013.01); *B01J 37/036* (2013.01); *B01J 37/06* (2013.01); *B01J 37/08* (2013.01); *B01J 37/18* (2013.01); *C07C 29/80* (2013.01); *B01J 2208/021* (2013.01)

(58) Field of Classification Search
CPC ................................ C07C 29/34; C07C 29/80
USPC ........................................................ 568/905
See application file for complete search history.

(56) References Cited

U.S. PATENT DOCUMENTS

| | | |
|---|---|---|
| 1,992,480 A | 2/1935 | Fuchs et al. |
| 2,004,350 A | 6/1935 | Scott |

(Continued)

FOREIGN PATENT DOCUMENTS

| | | |
|---|---|---|
| EP | 2080749 A1 | 7/2009 |
| EP | 2679304 A1 | 1/2014 |

(Continued)

OTHER PUBLICATIONS

European Search Report for EP 13 38 2570, dated Jun. 4, 2014, 5 pgs.

(Continued)

*Primary Examiner* — Sikarl A Witherspoon
(74) *Attorney, Agent, or Firm* — Armstrong Teasdale LLP

(57) ABSTRACT

The present disclosure generally relates to processes for preparation of n-butanol, n-octanol and n-decanol from a reaction mixture comprising ethanoi and n-hexanol by Guerbet condensation. In some aspects, the present disclosure relates to improvements in n-octanol and n-decanol yield and selectivity by the selection of process reaction conditions such as, but not limited to, mole ratio of n-hexanol to ethanol. The present disclosure further generally relates to integrated processes for preparation of n-butanol in a n-butanol reactor from a reaction mixture comprising ethanol and hydrogen to produce a n-butanol product stream by Guerbet condensation comprising n-butanol and n-hexanol and for preparation of n-octanol in a n-octanol reactor from a reaction mixture comprising ethanol, n-hexanol and hydrogen to produce a n-octanol product stream by Geurbet condensation comprising n-butanol, n-hexanol and n-octanol. A predominant proportion of the n-hexanol contained in the n-butanol and n-octanol product streams is isolated and recycled to the n-octanol reaction mixture. In some aspects, the present disclosure relates to improvements in n-octanol and n-butanol yield and selectivity by the selection of process reaction conditions such as, but not limited to, mole ratio of n-hexanol to ethanol and recovery and recycle of n-hexanol.

20 Claims, 11 Drawing Sheets

(51) Int. Cl.
  *B01J 23/08* (2006.01)
  *B01J 23/62* (2006.01)
  *B01J 23/72* (2006.01)
  *B01J 23/89* (2006.01)
  *B01J 8/02* (2006.01)
  *B01D 3/14* (2006.01)
  *B01D 3/00* (2006.01)

(56) References Cited

U.S. PATENT DOCUMENTS

| | | |
|---|---|---|
| 5,300,695 A | 4/1994 | Radlowski |
| 6,419,797 B1 | 7/2002 | Scherf et al. |
| 7,700,812 B2 | 4/2010 | Kourtakis et al. |
| 8,071,823 B2 | 12/2011 | Ozer et al. |
| 8,080,695 B2 | 12/2011 | Tsuchida et al. |
| 8,318,990 B2 | 11/2012 | Tanaka et al. |
| 9,266,096 B2 | 2/2016 | Arjona Antolin et al. |
| 9,475,741 B2 | 10/2016 | Arjona Antolin et al. |
| 2009/0056204 A1* | 3/2009 | Tsuchida ............... C07C 29/34 44/452 |
| 2010/0174121 A1 | 7/2010 | Manzer et al. |
| 2010/0298613 A1* | 11/2010 | Tanaka .................. C07C 29/34 568/905 |
| 2012/0271085 A1 | 10/2012 | Nesterenko et al. |
| 2012/0323050 A1 | 12/2012 | Lee et al. |
| 2013/0116481 A1 | 5/2013 | Wass et al. |
| 2016/0326075 A1 | 11/2016 | Sanz Yague et al. |

FOREIGN PATENT DOCUMENTS

| | | |
|---|---|---|
| WO | 9104242 A1 | 4/1991 |
| WO | 2015097285 A1 | 7/2015 |

OTHER PUBLICATIONS

European Search Report for EP 13 38 2572, dated Jun. 4, 2014, 6 pgs.
European Search Report for EP 13 38 2573, dated Jun. 4, 2014, 6 pgs.
European Search Report for EP 13 38 2574, dated Jun. 4, 2014, 6 pgs.
International Search Report and Written Opinion for Application No. PCT/EP2014/0796306, dated Apr. 21, 2015, 11 pgs.
International Search Report and Written Opinion for Application No. PCT/IB2015/002217, dated Feb. 11, 2016, 10 pgs.
International Preliminary Report on Patentability for Application No. PCT/EP2014/0796306, dated Jun. 28, 2016, 7 pgs.

* cited by examiner

PROCESS FOR THE PREPARATION OF HIGHER ALCOHOLS FROM ETHANOL AND N-HEXANOL BY GUERBET CONDENSATION

REFERENCE TO RELATED APPLICATIONS

This application is a United States National Stage Application based on International Patent Application Number PCT/IB2015/002217, filed Nov. 13, 2015, and claims the benefit of Spanish Patent Application Number P201431667, filed Nov. 14, 2014 and of Spanish Patent Application Number P201431669, filed Nov. 14, 2014, the entire contents of which are incorporated herein by reference.

BACKGROUND

This disclosure relates generally to processes for the preparation of higher alcohols from ethanol and n-hexanol by Guerbet condensation.

Higher alcohols, having from 8 to 16 carbon atoms, are valuable for use as plasticizers such as cold-resistant auxiliary plasticizers of plastics, antifoaming agents, dispersing agents, surfactants, mineral separation agents and petroleum additives. Higher alcohols are also valuable for use in other applications such as in cosmetics, printing and dyeing, paint, and photographic film.

Lower alcohols, having from 2 to 4 carbon atoms (ethanol and n-butanol), are useful as fuel additives. However, there are problems associated with the use of ethanol fuel in internal combustion engines, including its water solubility, corrosivity and the differences in its fuel properties compared to gasoline. In order to overcome the disadvantages of ethanol as a fuel, catalytic condensation of ethanol to n-butanol can be carried out. Compared to ethanol, n-butanol has several advantages. For instance, n-butanol can be burned in the existing gasoline engines without practically any engine or car modifications and it has higher energy content and air-to-fuel ratio.

n-butanol can be obtained by means of the well-known Guerbet reaction, which makes it possible to catalytically convert ethanol to n-butanol. Preparation of n-butanol by Guerbet synthesis from ethanol problematically results in the production of significant amounts n-hexanol. Typically from about 0.05 to about 0.1 moles of n-hexanol are generated in Guerbet condensation of ethanol per mole of n-butanol produced. Problematically, as compared to ethanol and butanol and as further compared to higher alcohols having from 8 to 16 carbon atoms, n-hexanol has limited industrial applicability, is of lower value, and is typically incinerated for energy recovery.

A need therefore exists for improved processes for the generation of higher alcohols by Guerbet condensation of lower alcohols wherein the amount of n-butanol and n-octanol produced is maximized and the amount of n-hexanol produced is minimized.

BRIEF SUMMARY

In one aspect of the present disclosure, a method of preparing n-octanol is provided. The method comprises forming a reaction mixture gas comprising a source of ethanol, a source of hydrogen, and a source of n-hexanol comprising at least 50 mole percent recovered n-hexanol, the reaction mixture comprising a mole ratio ethanol to n-hexanol of from about 0.3:1 to about 3:1. The reaction mixture is contacted with a Guerbet catalyst in a gas phase reactor having a fixed catalyst bed at a reaction temperature of from about 150° C. to 450° C. and a reaction pressure of from about 10 to about 200 bara to form a reactor product stream comprising ethanol, water, n-butanol, n-hexanol, n-octanol and hydrogen wherein the selectivity to n-octanol is at least 10% on a carbon basis and wherein the selectivity n-butanol is at least 10% on a carbon basis. The reactor product stream is fractionated to form the recovered n-hexanol, a n-butanol product stream and a n-octanol product stream.

In another aspect of the present disclosure, a Guerbet condensation reaction product mixture is provided. The condensation reaction product mixture comprises from about 0.3 to about 0.5 mole fraction ethanol, from about 0.01 to about 0.08 mole fraction n-butanol, from about 0.25 to about 0.45 mole fraction n-hexanol, and from about 0.03 to about 0.08 mole fraction n-octanol.

In another aspect of the present disclosure, a facility for manufacturing n-butanol, n-octanol and n-decanol from a source of ethanol and a source of n-hexanol is provided. The facility comprises an octanol reactor system comprising at least one gas phase reactor having a fixed catalyst bed, the reactor comprising (i) an inlet for the input of a reactor feed stream gas comprising a source of ethanol, a source of n-hexanol and a source of hydrogen, (ii) a reaction zone containing a heterogeneous catalyst for contact with the reactor feed stream to form an octanol reactor product stream, and (iii) an outlet for the discharge of the octanol reactor product stream, said octanol reactor product stream comprising ethanol, water, n-butanol, n-hexanol, n-octanol, n-decanol and hydrogen, wherein the reactor system is operational at a reaction temperature of from about 150° C. to 450° C. and at a reaction pressure of from about 10 to about 200 bara. The facility further comprises a first system for fractionating the octanol reactor product stream, the first fractionating system comprises a distillation column or a flash column and forms (i) a first fractionated stream, said stream comprising at least 95 mole percent each of the water, the ethanol and the hydrogen contained in the octanol reactor product stream and (ii) a second fractionated stream, said stream comprising at least 95 mole percent each of the n-butanol, the n-hexanol, the n-octanol and the n-decanol contained in the octanol reactor product stream. The facility further comprises a second system for fractionating the first fractionated stream, wherein the first fractionated stream comprises vapor and the second system for fractionating the first fractionated stream comprises a condenser and an ethanol dehydration system wherein (i) the vapor is passed through the condenser to fractionate the recovered hydrogen stream as a gas and wet ethanol as a condensate and (ii) the wet ethanol is dehydrated to form the recovered ethanol stream and a water stream, wherein the second fractionating system forms (i) a recovered ethanol stream comprising at least 95 mole percent of the ethanol and less than 5 mole percent of the water contained in the first fractionated stream and (ii) a recovered hydrogen stream, said stream comprising at least 95 mole percent of the hydrogen contained in the first fractionated stream, wherein the second fractionating system recovered ethanol stream and recovered hydrogen stream are interconnected with the source of ethanol and the source of hydrogen for the octanol reactor system and at least a portion of the recovered ethanol and the recovered hydrogen is recycled to the octanol reactor system. The facility further comprises a third system for fractionating the second fractionated stream, the third fractionating system comprising a distillation column that forms (i) a third fractionated stream, said stream comprising at least 95 mole percent of the n-butanol contained in the second fractionated stream and (ii) a fourth fractionated stream, said stream comprising at least 95 mole percent each of the n-hexanol, the n-octanol and the n-decanol contained in the second fractionated stream. The facility further comprises a fourth system for fractionating the fourth fractionated stream, the fourth fractionating system comprising a distillation column that forms (i) a recovered n-hexanol stream, said stream comprising at least 95 mole percent of the n-hexanol contained in the fourth fractionated stream and (ii) a fifth fractionated, said stream comprising at least 95 mole percent each of the n-octanol and n-decanol contained in the fourth fractionated stream, wherein the fourth fractionating system recovered n-hexanol stream is interconnected with the source of n-hexanol for the octanol reactor system and at least a portion of the recovered n-hexanol is recycled to the octanol reactor system. The facility further comprises a fifth system for fractionating the fifth fractionated stream, the fifth fractionating system to form (i) a n-octanol product stream, said stream comprising at least 95 mole percent of the n-octanol contained in the fifth fractionated stream and (ii) a n-decanol product stream, said stream comprising at least 95 mole percent each of the n-decanol contained in the fifth fractionated stream.

In another aspect of the present disclosure, a continuous process for preparing n-butanol and n-octanol is provided. The process comprises (1) forming a gas phase n-butanol reaction mixture comprising a source of ethanol and a source of hydrogen, (2) reacting the gas phase n-butanol reaction mixture by contact with a Guerbet catalyst in a gas-phase n-butanol reactor at a reaction temperature of from about 150° C. to 450° C. and a reaction pressure of from about 10 to about 200 bara to form a n-butanol reactor product stream comprising n-butanol and n-hexanol and (3) fractionating the n-butanol reactor product stream to form a n-butanol product stream and a recovered n-hexanol stream. The process further comprises (1) forming a gas phase n-octanol reaction mixture comprising a source of n-hexanol comprising at least a portion of the n-hexanol recovered from the n-butanol reaction mixture and the n-octanol reaction mixture, a source of ethanol and a source of hydrogen, (2) reacting the gas phase n-octanol reaction mixture by contact with a Guerbet catalyst in a gas phase n-octanol reactor at a reaction temperature of from about 150° C. to 450° C. and a reaction pressure of from about 10 to about 200 bara to form a n-octanol reactor product stream comprising n-octanol, n-butanol and n-hexanol and (3) fractionating the n-octanol reactor product stream to form a n-octanol product stream, a recovered n-hexanol stream and a n-butanol product stream.

In another aspect of the present disclosure, a facility for manufacturing n-butanol and n-octanol from a source of ethanol and a source of n-hexanol is provided. The facility comprises a n-butanol reactor system comprising at least one gas phase reactor having a fixed catalyst bed, the reactor comprising (1) an inlet for the input of a n-butanol reactor system feed stream gas comprising a source of ethanol and a source of hydrogen, (2) a reaction zone containing a heterogeneous catalyst for contact with the catalyst to form a n-butanol reactor product stream, and (3) an outlet for the discharge of a n-butanol reactor system product stream, the n-butanol reactor product stream comprising ethanol, water, n-hexanol, and hydrogen, wherein the n-butanol reactor system is operational at a reaction temperature of from about 150° C. to 450° C. and at a reaction pressure of from about 10 to about 200 bara. The facility further comprises a n-octanol reactor system comprising at least one gas phase reactor having a fixed catalyst bed, the reactor comprising (1) an inlet for the input of a n-octanol reactor feed stream gas comprising a source of ethanol, a source of n-hexanol and a source of hydrogen, (2) a reaction zone containing a heterogeneous catalyst for contact with the reactor feed stream to form a n-octanol reactor product stream, and (3) an outlet for the discharge of the n-octanol reactor product stream, the n-octanol reactor product stream comprising ethanol, water, n-hexanol, n-octanol and hydrogen, wherein the n-octanol reactor system is operational at a reaction temperature of from about 150° C. to 450° C. and at a reaction pressure of from about 10 to about 200 bara. The facility yet further comprises a first system for fractionating the n-butanol reactor product stream and the n-octanol reactor product stream, wherein the first fractionating system comprises a distillation column or a flash column that forms (1) a first fractionated stream comprising at least 95 mole percent each of the water, the ethanol and the hydrogen contained in the n-butanol reactor product stream and the n-octanol reactor product stream and (2) a second fractionated stream comprising at least 95 mole percent each of the n-butanol, the n-hexanol and the n-octanol contained in the n-butanol reactor stream and the n-octanol reactor product stream. The facility still further comprises a second system for fractionating the second fractionated stream, wherein the second fractionating system comprises a distillation column that forms (1) a n-butanol enriched stream comprising at least 95 mole percent of the n-butanol contained in the second fractionated stream and (2) a fourth fractionated stream comprising at least 95 mole percent each of the n-hexanol and the n-octanol contained in the second fractionated stream. Still further, the facility comprises a third system for fractionating the fourth fractionated stream, wherein the third fractionating system comprises a distillation column that forms (1) a recovered n-hexanol stream comprising at least 95 mole percent of the n-hexanol contained in the fourth fractionated stream, wherein the recovered n-hexanol stream is interconnected with the source of n-hexanol for the n-octanol reactor system and at least a portion of the recovered n-hexanol is recycled to the n-octanol reactor feed stream and (2) a n-octanol stream comprising at least 95 mole percent of the n-octanol contained in the fourth fractionated stream.

DETAILED DESCRIPTION

Figure 1:
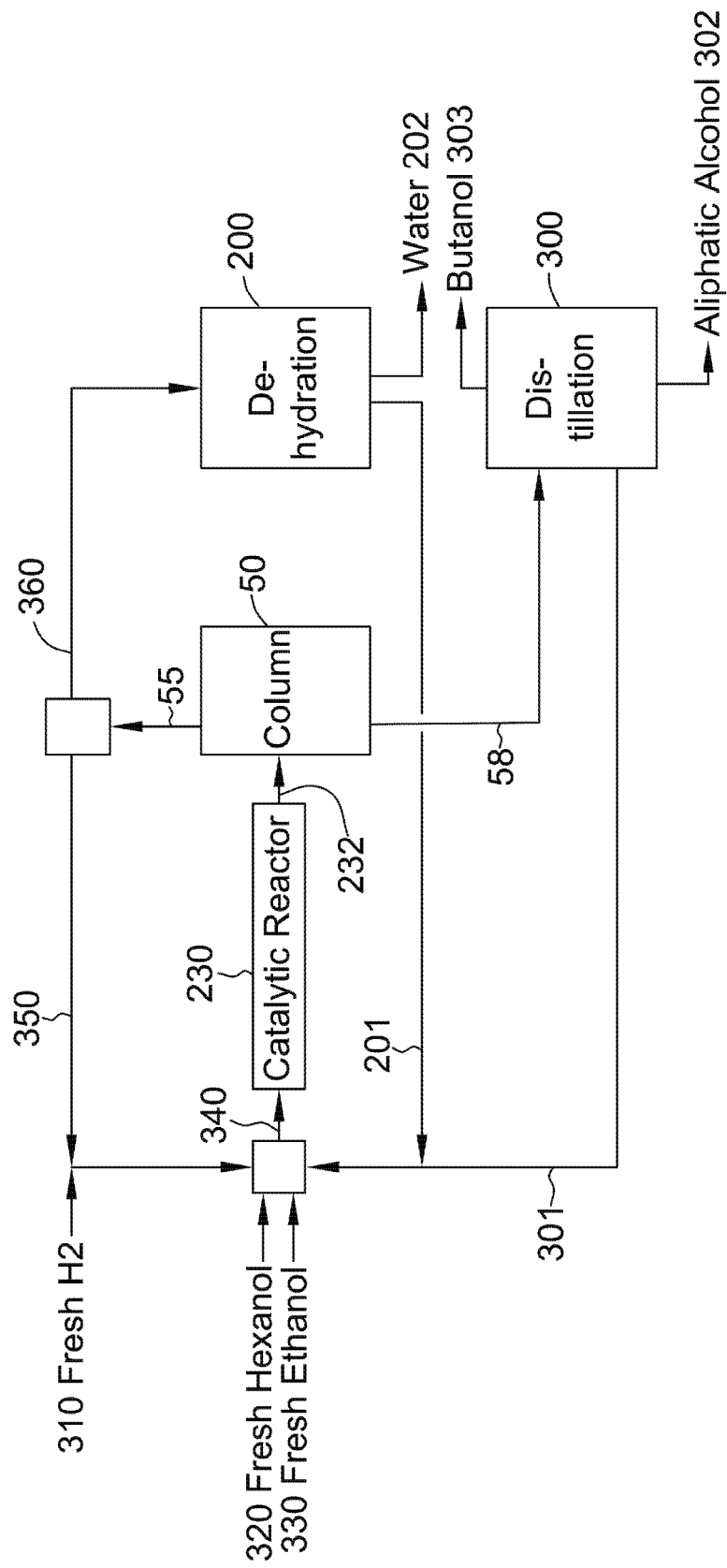
FIG. 1 is a process flow diagram of a first aspect of the present disclosure.

The present disclosure generally relates to a catalytic process for producing $C_4$ and $C_8$ to $C_{16}$ higher alcohols by Guerbet condensation by the catalytic condensation of alcohols under conditions of elevated temperature and pressure by a dehydrogenation, aldol condensation and hydrogenation. In some aspects of the present disclosure, $C_8$ to $C_{16}$ higher alcohols are prepared by Guerbet condensation of a reaction mixture comprising ethanol and a source of n-hexanol comprising recovered n-hexanol. In some aspects of the present disclosure, at least a portion of the n-hexanol is recovered from a n-butanol preparation process wherein a reaction mixture comprising ethanol is contacted with a Guerbet catalyst to form a n-butanol reaction product mixture comprising n-butanol, n-hexanol and unreacted ethanol. In some other aspects of the present disclosure, at least a portion of the n-hexanol is recovered from a n-octanol preparation process wherein a reaction mixture comprising ethanol and n-hexanol is contacted with a Guerbet catalyst to form a n-octanol reaction product mixture comprising n-octanol and unreacted n-hexanol and ethanol. In yet other aspects of the present disclosure, n-hexanol is recovered from both n-butanol and n-octanol reaction product mixtures. In still other aspects of the present disclosure, at least a portion of the ethanol in the reaction mixture for the preparation of n-butanol and/or the reaction mixture for the preparation of n-octanol is recovered from the n-butanol reaction product mixture and/or the n-octanol reaction product mixture.

For the preparation of butanol from ethanol, the reaction sequence may be described as follows:

$$CH_3CH_2OH \rightarrow CH_3CHO + H_2 \quad (1)$$

$$CH_3CH_2OH + CH_3CHO + H_2 \rightarrow C_4H_9OH + H_2O \quad (2)$$

And the overall reaction is as follows:

$$2CH_3CH_2OH \rightarrow C_4H_9OH + H_2O \quad (3)$$

n-hexanol may be generated by the condensation of n-butanol and ethanol according to the overall reaction $CH_3(CH_2)_3OH + CH_3CH_2OH \rightarrow C_6H_{13}OH + H_2O$.

n-octanol may be generated by: (i) the condensation of n-hexanol and ethanol according to the overall reaction $CH_3CH_2OH + C_6H_{13}OH \rightarrow C_8H_{17}OH + H_2O$, (ii) the condensation of two n-butanol molecules according to the overall reaction $2\ CH_3(CH_2)_3OH \rightarrow C_8H_{17}OH + H_2O$ and/or (iii) by the successive condensation of n-butanol with ethanol.

n-decanol may be generated by: (i) the condensation of n-octanol and ethanol according to the overall reaction $CH_3CH_2OH + C_8H_{17}OH \rightarrow C_{10}H_{21}OH + H_2O$ and/or (ii) the condensation of n-butanol and n-hexanol according to the overall reaction $CH_3(CH_2)_3OH + C_6H_{13}OH \rightarrow C_{10}H_{21}OH + H_2O$.

In accordance with the present disclosure, it has been discovered that starting alcohol mixture (e.g., ethanol and n-hexanol) conversion rate, selectivity to Guerbet alcohols (e.g., n-butanol, n-hexanol, n-octanol and n-decanol) and Guerbet alcohol yield are generally affected by a number of factors. It has been further discovered that optimization of those factors, and combinations thereof, enable the preparation of n-butanol, n-octanol and n-decanol in high selectivity and yield. For instance, the following non-limiting list of factors has been discovered to affect the efficiency of the Guerbet reaction of the present disclosure: (i) the catalyst, catalyst loading and catalyst life, (ii) the ratio of ethanol to n-hexanol in the reaction mixture, (iii) the concentration of various impurities and co-reactants in the reactor feed stream and various recycle streams, for instance and without restriction, water and hydrogen, (iv) the ratios of said impurities and co-reactants to starting alcohol, (v) reaction temperature, (vi) reaction pressure, (vii) reactor liquid hourly space velocity ("LHSV"), wherein LHSV refers to the quotient of the entering volumetric flow rate of the reactants divided by the reactor volume and is an indication of the number of reactor volumes of reactant feed that can be treated in a unit time; and (viii) selected combinations of one or more of (i) to (vii).

As used herein, the terms "$C_3$ to $C_{16}$ higher alcohols" is understood to mean any linear or branched alkyl chain with at least one hydroxyl functional group which has between 3 and 16 carbon atoms. Non-limiting examples are propanol, isopropanol, n-butanol, 2-butanol, 2-methyl-2-butanol, 3-methyl-1-butanol-1-pentanol, 2-pentanol, 3-pentanol, 2,2-dimethyl-1-propanol, 3-methyl-2-butanol, 1,5-pentanediol, 2,4-pentanediol, 2,2-dimethyl-1,3-propanediol, 1,2-butanediol, 1,3-butanediol, 1,4-butanediol, 2,3-butanediol, 1-heptanol, 2-heptanol, 3-heptanol, 4-heptanol, 2-methyl-2-hexanol, 2,2-dimethyl-3-pentanol-1-octanol, 2-octanol, 3-octanol, 4-octanol, 2-ethyl-n-hexanol, 3-ethyl-1-hexanol, 2,2-dimethyl-3-hexanol, n-decanol, 2-decanol, 3-decanol, 4-decanol. As used herein, "condensate" refers to a process stream predominantly comprising condensed liquids at the temperature and pressure thereof, but not excluding the present of some amount of gas or vapor. As used herein, "gas" and "vapor" are used interchangeably and may comprise condensable compounds (e.g., ethanol) and essentially non-condensable compounds (e.g., hydrogen), and does not exclude the possibility of some liquid entrainment. As used herein, "predominantly" means greater than 50%, at least 75%, at least 90% or at least 95% on a population %, w/w %, w/v % or v/v % basis. As used herein, "trace amount" and "essential absence" refer to a detectable, but minor amount, such as less than about 0.05 mole % or less than about 0.01 mole %. As used herein "n-butanol," "n-hexanol," "n-octanol" and "n-decanol" refer to 1-butanol, 1-hexanol, 1-octanol and 1-decanol, respectively.

Various non-limiting aspects of the present disclosure are depicted in FIGS. 1 to 11.

FIG. 1 depicts a first aspect of the process of the present disclosure wherein a reaction mixture 340 is formed by combining fresh ethanol 330, recycled ethanol 201, recycled n-hexanol 301, optional fresh n-hexanol 320, fresh hydrogen 310 and recycled hydrogen 350. The reaction mixture is vaporized and contacted with a heterogeneous catalyst under elevated temperature and pressure conditions in octanol reactor system 230 to form a reactor product stream 232 comprising water, hydrogen, ethanol, n-butanol, n-hexanol and $C_8$ and $C_{10}$ aliphatic alcohols including n-octanol and n-decanol. The reactor product stream 232 is fractionated in splitter column 50 to form (i) splitter column bottoms stream 58 predominantly comprising high boiling compounds including n-butanol, i-butanol, n-hexanol and heavier aliphatic alcohols including n-octanol and n-decanol and (ii) a splitter column overhead stream predominantly comprising ethanol, water and hydrogen. The splitter column overhead stream is processed to form recycled hydrogen stream 350 and wet ethanol stream 360. Wet ethanol stream 360 is processed by ethanol dehydration 200 to form recycled ethanol stream 201 and water stream 202. The splitter column bottoms stream 58 is fractionated in a multi-step distillation operation 300 to form a mixed butanol isomer stream 303, n-hexanol for recycle 301 and aliphatic alcohols 302 comprising n-octanol and n-decanol. The mixed butanol isomer stream 303 is optionally fractionated to produce a first stream predominantly comprising n-butanol and a second stream predominantly comprising i-butanol.

Figure 2:
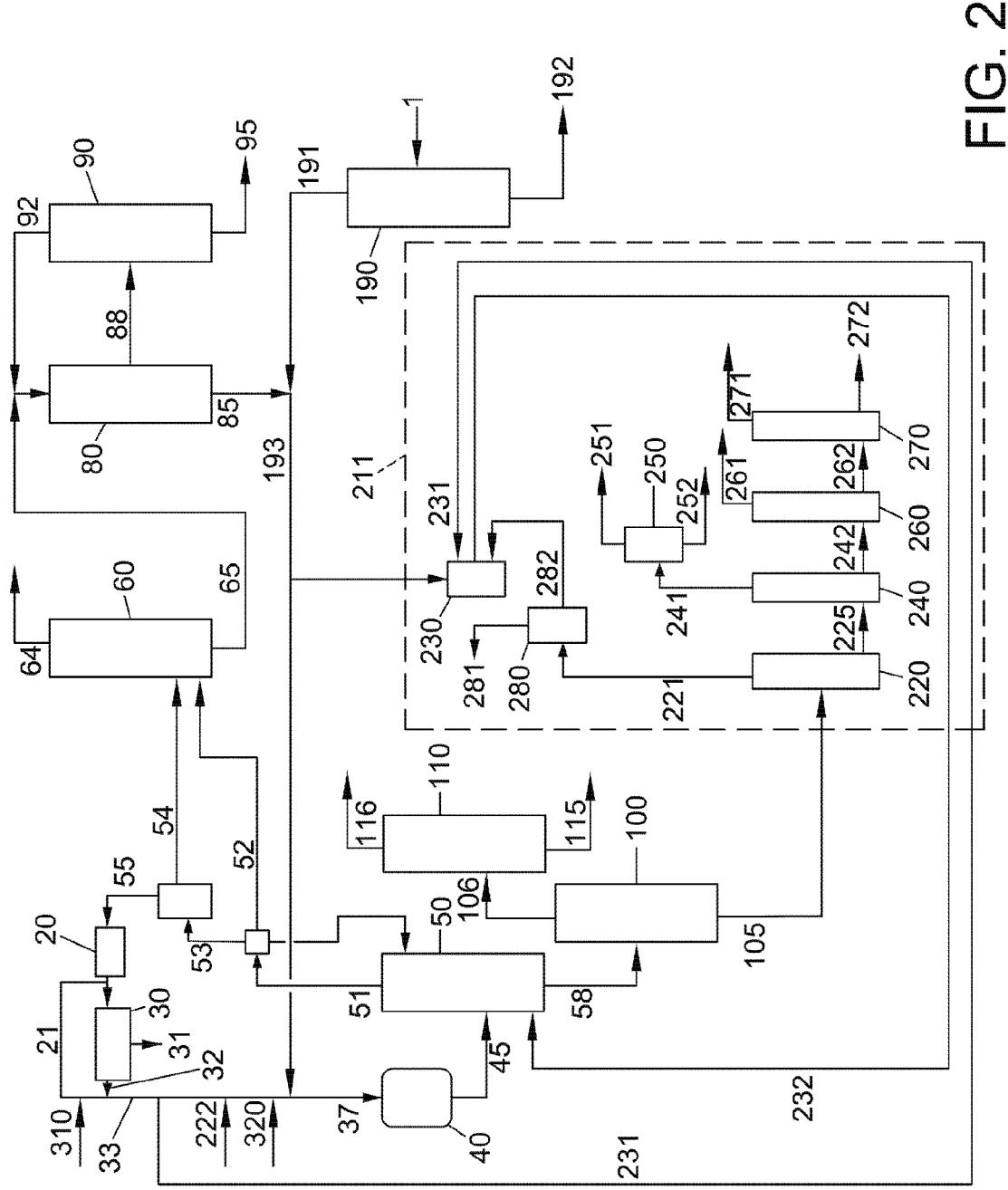
FIG. 2 is a process flow diagram of a second aspect of the present disclosure.

In another aspect of the disclosure, depicted in FIG. 2, hexanol 105 generated as a by-product in an ethanol-to-butanol Guerbet condensation reaction is isolated and reacted in a Guerbet condensation reaction with a source of hydrogen 231 and a source of ethanol 193 to form n-octanol 252 and n-decanol 271 as generally depicted in system 211. In particular, fresh ethanol feed 1 is optionally fractionated in fusel column 190 to a form a distilled fresh ethanol feed stream 191 and a fusel oil stream 192 predominantly comprising amyl alcohol. Fresh ethanol feed 1 or distilled fresh ethanol stream 191 may be optionally passed through a purification bed (not depicted in FIG. 2) for removal of impurities (e.g., salts and ions). Fresh ethanol feed stream 191 may be optionally processed in molecular sieves 80 for water removal. Fresh ethanol feed stream 191 is combined with dry recovered ethanol stream 85 that is characterized by the essential absence of water to form a source of ethanol 193 for butanol reactor system 40 and octanol reactor system 230. A reaction mixture formed from ethanol stream 193 and gas stream 33 comprising recovered hydrogen and optional fresh hydrogen 310 is heated to form reactor feed gas stream 37. In some optional aspects of the disclosure, the reaction mixture further comprises recovered n-hexanol 222 and/or fresh n-hexanol 320. Reactor feed gas stream 37 is contacted with a heterogeneous catalyst under elevated temperature and pressure conditions in butanol reactor system 40 to form a reactor product stream 45 comprising water, hydrogen, acetaldehyde, ethyl acetate, n-butanol, i-butanol, n-hexanol, $C_8$ and $C_{10}$ aliphatic alcohols including n-octanol and n-decanol, and $C_{10+}$ alcohols. In any of the various aspects of the present disclosure depicted in the figures and described herein, a butanol reactor system 40 may comprise two or more reactors arranged in series or in parallel fed by one or more reactor feed gas streams 37. Reactor product stream 45 is fractionated in splitter column 50 to form (i) splitter column bottoms stream 58 predominantly comprising high boiling compounds including n-butanol, i-butanol, n-hexanol, n-octanol and n-decanol and (ii) splitter column first overhead stream 51 comprising ethanol, acetaldehyde, ethyl acetate and hydrogen. Splitter column first overhead stream 51 is passed through a condenser to form (i) first condensate stream 52 that is divided between splitter column 50 reflux and ethyl acetate column 60 feed and (ii) splitter column gas stream 53. Splitter column gas stream 53 is passed through a second condenser to form splitter column second overhead condensate stream 54 and splitter column second gas stream 55. Splitter column second gas stream 55 is pressurized in recycle compressor 20 to form compressed splitter column second gas stream 21 that may be the gas source for gas stream 33. In some other aspects of the present disclosure, compressed splitter column second gas stream 21 may be processed by pressure swing adsorption 30 to form hydrogen gas stream 32 that is the gas source for gas stream 33 and purge stream 31 comprising hydrogen, carbon dioxide, carbon monoxide and ethane. In some other aspects of the present disclosure, a combination of compressed splitter column second gas stream 21 and hydrogen gas stream 32 form gas stream 33. Splitter column second overhead condensate stream 54 and at least a portion of splitter column first condensate stream 52 is forwarded to ethyl acetate column 60 where the streams are fractionated to form ethyl acetate column bottoms stream 65 predominantly comprising ethanol and water and ethyl acetate column overhead purge stream 64 predominantly comprising acetaldehyde, hydrogen and ethyl acetate. In one optional aspect not depicted in FIG. 2, ethyl acetate column overhead purge stream 64 may be partially condensed and a portion of the condensate may be recycled to ethyl acetate column 60 and a portion of the condensate may be purged from the process. Ethyl acetate column 60 bottoms stream 65 comprising wet ethanol is sent to molecular sieve 80 inlet. Ethyl acetate column bottoms stream 65 and wet ethanol stream 92 from the regeneration column are combined and processed in molecular sieves 80 to form water rich stream 88 and dry ethanol stream 85. The molecular sieve water rich feed stream 88 comprises ethanol and is processed in regeneration column 90 where water and isoamyl alcohol (if present) are separated from ethanol to form regeneration column bottoms stream 95 comprising water that is sent to waste water treatment and wet ethanol stream 92 that is then sent to molecular sieve 80 inlet. Splitter column bottoms stream 58 is fractionated in hexanol column 100 to form hexanol column bottoms stream 105 predominantly comprising n-hexanol, n-octanol and n-decanol as major components and hexanol column condenser overhead stream 106 comprising n-butanol and i-butanol. In some optional aspects of the disclosure, splitter column bottoms stream 58 may be fractioned according to system 210 depicted in FIG. 3 (described elsewhere herein) to generate various streams including n-hexanol for conversion to n-octanol in octanol reactor system 230 and n-octanol. Hexanol column condenser overhead stream 106 is fractionated in isobutanol column 110 to form a hexanol column bottoms stream 115 comprising essentially pure n-butanol and a condensed hexanol column overhead stream 116 comprising i-butanol. Hexanol column bottoms stream 105 is fractionated in hexanol purification column 220 to form overhead stream 221 that is fractionated in hexanol finishing column 280 to form bottoms stream 282 predominantly comprising purified n-hexanol and overhead stream 281 predominantly comprising 2-ethyl butanol. Purified n-hexanol stream 282 is combined with a source of ethanol 193 and gas stream 231 (corresponding to gas stream 33) comprising recovered hydrogen, and optionally a source of fresh hydrogen 310 (not depicted) is heated to form a feed gas stream to octanol reactor 230. In octanol reactor 230, the feed gas stream is contacted with a heterogeneous catalyst at elevated temperature and pressure to form octanol reactor product stream 232 comprising ethanol, i-butanol, n-butanol, n-hexanol, hexanal (hexanaldehyde), n-octanol, n-decanol, 2-ethyl-hexanol, i-decanol, and various compounds having a higher boiling point than decanol isomers. Octanol reactor product stream 232 is refluxed to splitter column 50. Components comprising ethanol, water, hydrogen and acetaldehyde are fractionated into overhead stream 51 and organic compounds having four our greater carbon atoms are fractionated into bottom stream 58. Hexanol purification column 220 bottoms stream 225, comprising n-octanol, n-decanol, 2-ethyl-hexanol, and i-decanol is forwarded to octanol column 240 and fractionated to form bottoms stream 242 comprising n-decanol, 2-ethyl-1-octanol (i-decanol), and high boiling compounds and overhead stream 241 comprising n-octanol and 2-ethyl-hexanol. Overhead stream 241 is forwarded to n-octanol purification column 250 and fractionated to form overhead stream 251 predominantly comprising 2-ethyl-hexanol and bottoms stream 252 predominantly comprising n-octanol. Bottoms stream 242 is forwarded to i-decanol column 260 and fractionated to form overhead stream 261 predominantly comprising 2-ethyl-n-octanol and bottoms stream 262 comprising n-decanol and high boiling compounds. Bottoms stream 262 is forwarded to n-decanol column 270 to form overhead stream 271 predominantly comprising n-decanol and bottoms stream 272 predominantly comprising high boiling compounds. In some aspects of the disclosure, the process depicted in FIG. 2 is characterized by the absence of a product or waste stream comprising in excess of 0.001, 0.005 or 0.01 mole percent n-hexanol.

Figure 3:
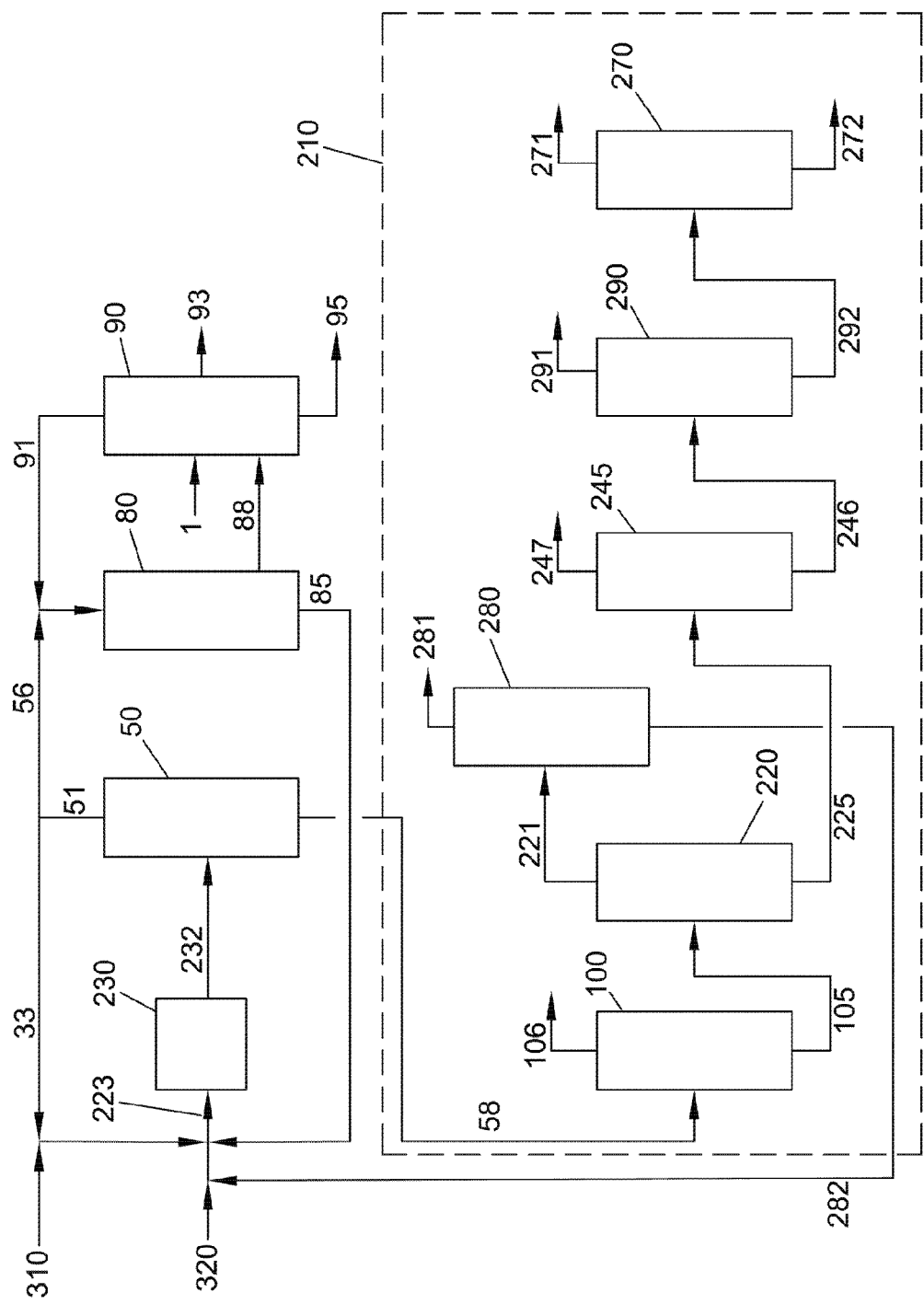
FIG. 3 is a process flow diagram of a third aspect of the present disclosure.

In another aspect of the present disclosure depicted in FIG. 3, fresh ethanol feed 1 is optionally passed through a purification bed (not depicted in FIG. 3) for removal of impurities (e.g., salts and ions) to form a fresh ethanol feed stream comprising ethanol and water. In some aspects of the present disclosure, fresh ethanol may comprise isoamyl alcohol. In such aspects, feed stream 1 may be fractionated in regeneration column 90 to separate water and isoamyl alcohol from ethanol to form regeneration column bottoms stream 95 comprising water that is sent to waste water treatment, isoamyl alcohol stream 93 and regeneration column overhead stream 91 enriched in ethanol that is passed through a condenser to form a reflux stream and a wet ethanol stream that is then sent to molecular sieve 80 inlet. The wet ethanol stream 91 is combined with a recovered ethanol stream 56 and processed in the molecular sieves 80 to form a dry ethanol stream 85 and a water rich ethanol stream 88. Dry recycle stream 85 is fed forward to the octanol reactor system 230 and the water rich ethanol stream 88 is fed forward to the Regeneration Column 90. Dry ethanol stream 85 is combined with gas stream 33 comprising recovered hydrogen, recovered n-hexanol 282, optional fresh hydrogen 310 and fresh n-hexanol 320 to form a reactor feed stream that is heated to form reactor feed gas stream 223. Reactor feed gas stream 223 is contacted with a heterogeneous catalyst under elevated temperature and pressure conditions in reactor system 230 to form a reactor product stream 232 comprising water, hydrogen, acetaldehyde, ethyl acetate, n-butanol, i-butanol, n-hexanol, $C_8$ and $C_{10}$ aliphatic alcohols including n-octanol and n-decanol, and $C_{10+}$ alcohols. Reactor product stream 232 is fractionated in splitter column 50 to form (i) splitter column bottoms stream 58 predominantly comprising having four or more carbon atoms including n-butanol, i-butanol, n-hexanol, n-octanol and n-decanol and (ii) splitter column overhead stream 51 predominantly comprising ethanol, acetaldehyde, ethyl acetate and hydrogen. Splitter column overhead stream 51 is passed through a condenser to form (i) gas stream 33 and (ii) splitter column overhead condensate stream 56 comprising recovered ethanol and water. In some optional aspects, not depicted in FIG. 3, the splitter column overhead stream 56 may be optionally further fractionated in one or more distillation columns and/or condensations to separate certain organic compounds, such as acetaldehyde and ethyl acetate, from ethanol. Splitter column overhead stream 56 is co-processed with regeneration column overhead stream 91 in molecular sieves 80 to generate dry ethanol stream 85. Splitter column bottoms stream 58 is fractionated in distillation system 210 to form process streams including recycled n-hexanol 282, n-octanol 291 and n-decanol 271. In distillation system 210, splitter column bottoms stream 58 is forwarded to butanol column 100 and fractionated to form an overhead stream 101 predominantly comprising n-butanol and i-butanol and a bottoms stream 105 comprising n-hexanol, n-octanol and n-decanol. In optional aspects of the present disclosure not depicted in FIG. 3, overhead stream 101 may be processed in an i-butanol column 110 to fractionate i-butanol (in a condensed overhead stream) from n-butanol (in a bottoms stream). Hexanol column bottoms stream 105 is fed forward to hexanol purification column 220 and fractionated to form overhead stream 221 comprising n-hexanol and 2-ethyl-butanol and bottoms stream 225 comprising 1-2-ethyl-hexanol, n-octanol and n-decanol. Overhead stream 221 is fed forward to 2-ethyl-butanol column 280 and fractionated to form overhead stream 281 predominantly comprising 2-ethyl-butanol and bottoms stream 282 predominantly comprising recovered n-hexanol for recycle to the octanol reactor system 230. Bottoms stream 225 is fed forward to 2-ethyl-hexanol column 245 and fractionated to form overhead stream 247 predominantly comprising 2-ethyl-hexanol and bottoms stream 246 predominantly comprising n-octanol, n-decanol, 2-ethyl-1-octanol (i-decanol) and high boiling compounds. Bottoms stream 246 is fed forward to n-octanol column 290 and fractionated to form overhead stream 291 predominantly comprising n-octanol and bottoms stream 292 predominantly comprising n-decanol and high boiling compounds such as hexa-decanol. Bottom stream 292 is fed forward to n-decanol column 270 and fractionated to form overhead stream 271 predominantly comprising n-decanol and bottoms stream 272 predominantly comprising high boiling compounds (e.g., hexa-decanol). In some aspects of the disclosure, the process depicted in FIG. 3 is characterized by the absence of a product or waste stream comprising in excess of 0.001, 0.005 or 0.01 mole percent n-hexanol.

Figure 4:
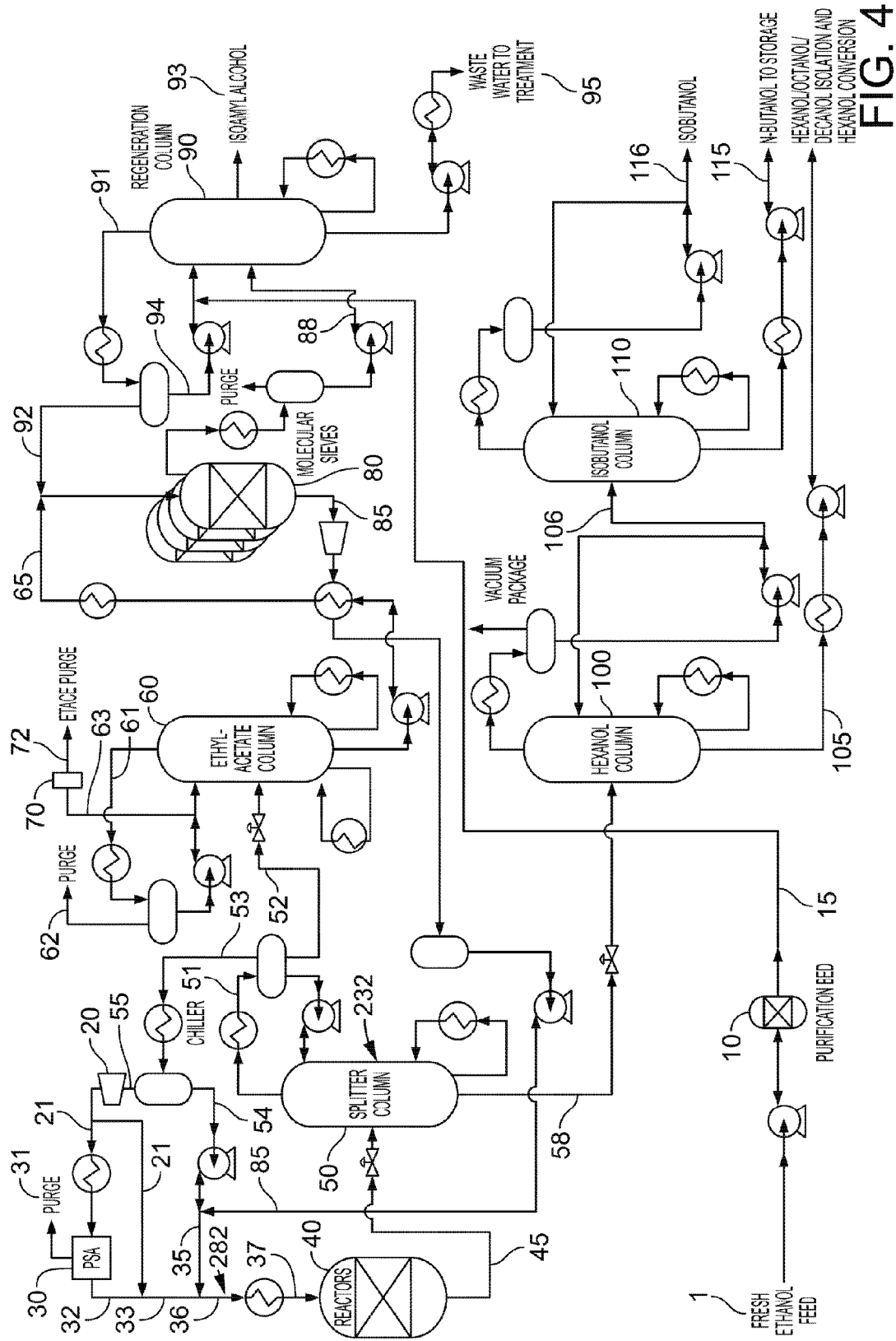
FIG. 4 is a process flow diagram of a fourth aspect of the present disclosure.

In another aspect of the present disclosure depicted in FIG. 4, generally, ethanol is condensed in the presence of hydrogen by contact with a Guerbet catalyst to form a reactor product stream comprising n-butanol and n-hexanol. n-butanol and n-hexanol are isolated by fractionation and the recovered n-hexanol is condensed with ethanol in the presence hydrogen by contact with a Guerbet catalyst to form a reactor product stream comprising n-octanol. In particular, fresh ethanol feed 1 is optionally passed through purification bed 10 for removal of impurities (e.g., salts and ions) to form a fresh ethanol feed stream 15 comprising ethanol and water. In some aspects of the present disclosure, fresh ethanol may comprise isoamyl alcohol. Optionally, fresh ethanol feed 1 or fresh ethanol feed stream 15 may be fractionated in a fusel oil column (not depicted in FIG. 4) to generate a distilled fresh ethanol feed stream that may be fed directly to butanol reactor system 40 and the octanol reactor system 230 and/or that may be combined with a recovered alcohol stream and dehydrated (such as by molecular sieves, a regeneration column and/or extractive distillation). Feed stream 15 is then fractionated in regeneration column 90. A molecular sieve 80 water rich feed stream 88 comprising ethanol is also fractionated in regeneration column 90. Regeneration column 90 separates water and isoamyl alcohol from ethanol to form regeneration column bottoms stream 95 comprising water that is sent to waste water treatment, isoamyl alcohol stream 93 and regeneration column overhead stream 91 that is passed through a condenser to form reflux stream 94 and wet ethanol stream 92 that is then sent to molecular sieve 80 inlet. Ethyl acetate column 60 bottoms stream 65 comprising wet ethanol is also sent to molecular sieve 80 inlet. Ethyl acetate column bottoms stream 65 and wet ethanol stream 92 are processed in molecular sieves 80 to form water rich stream 88 and dry ethanol stream 85 wherein stream 85 is characterized by the essential absence of acetaldehyde and very low water content. Dry ethanol stream 85 is combined with splitter column second overhead stream 54 comprising ethanol and acetaldehyde to form mixed ethanol feed stream 35. In some aspects of the present disclosure, dry ethanol stream 85 is the source of ethanol for the octanol reactor system 230. Mixed alcohol feed stream 35 is combined with gas stream 33 comprising hydrogen. In some optional aspects of the present disclosure, at least a portion of recovered n-hexanol 282 (see FIG. 2) or recovered n-hexanol 282 (see FIG. 3) and/or fresh n-hexanol may be added to reactor feed stream 36. In some other aspects of the present disclosure, gas stream 33 is the source of hydrogen for the octanol reactor system as described elsewhere herein. Reactor feed stream 36 is heated to form reactor feed vapor stream 37 that is sent to butanol reactor system 40 containing one reactor, or two or more reactors. In butanol reactor system 40, ethanol is contacted with a Guerbet catalyst under elevated pressure and temperature conditions to form reactor product stream 45. Reactor product stream 45 is fractionated in splitter column 50 to form splitter column bottoms stream 58 predominantly comprising high boiling compounds including n-butanol, i-butanol, n-hexanol, n-octanol and n-decanol and splitter column first overhead stream 51 comprising ethanol, acetaldehyde, ethyl acetate, hydrogen and carbon monoxide. In some aspects of the disclosure, the octanol reactor product stream 232 may be fractionated in splitter column 50. Splitter column first overhead stream 51 is passed through a condenser to form (i) first condensate stream 52 that is divided between splitter column 50 reflux and ethyl acetate column 60 feed and (ii) splitter column first gas stream 53. Splitter column gas stream 53 is passed through a second condenser to form splitter column second overhead condensate stream 54 and splitter column second gas stream 55. Splitter column second gas stream 55 is pressurized in recycle compressor 20 to form compressed splitter column second gas stream 21 that may be the gas source for gas stream 33. In some other aspects of the present disclosure, compressed splitter column second gas stream 21 may be processed by pressure swing adsorption 30 to form hydrogen gas stream 32 that is the gas source for gas stream 33 and purge stream 31 comprising hydrogen, carbon dioxide, carbon monoxide and ethane. In some other aspects of the present disclosure, a combination of compressed splitter column second gas stream 21 and hydrogen gas stream 32 form gas stream 33. In some further aspects of the present disclosure not depicted in FIG. 4, at least a portion of the hydrogen present in the reaction mixture is provided by a source of fresh hydrogen make-up. At least a portion of splitter column first condensate stream 52 is forwarded to ethyl acetate column 60 where it is fractionated to form ethyl acetate column bottoms stream 65 and ethyl acetate column overhead stream 61. Ethyl acetate column overhead stream 61 is passed through a condenser to form ethyl acetate column overhead gas purge stream 62 comprising acetaldehyde, hydrogen and ethyl acetate as major components and ethyl acetate column overhead condensate stream 63 comprising acetaldehyde, ethanol and ethyl acetate as major components. A portion of stream 63 is recycled to ethyl acetate column 60 and a portion of stream 63 is purged from the process. In one optional aspect of the present disclosure, stream 63 may be purified, such as by distillation column 70, to form purified ethyl acetate stream 72. Splitter column bottoms stream 58 is fractionated in hexanol column 100 to form hexanol column bottoms stream 105 comprising n-hexanol, n-octanol and n-decanol as major components and hexanol column condensed overhead stream 106 comprising n-butanol and minor amounts of n-propanol, i-butanol and 2-butanol. As described elsewhere herein, hexanol column bottoms stream 105 is fractionated in hexanol/octanol/decanol purification system 210 (such as depicted, for instance and without limitation, in FIGS. 2 and 3) to form recovered n-hexanol stream 282 (FIG. 2) or 282 (FIG. 3). As further described elsewhere herein (such as depicted, for instance, in FIGS. 2 and 3), recovered n-hexanol is combined with a source of ethanol and a source of hydrogen and contacted with a heterogeneous catalyst in octanol reactor system 230 under elevated temperature and pressure conditions to form n-octanol and n-decanol. Hexanol column condensed overhead stream 106 is fractionated in isobutanol column 110 to form an isobutanol column bottoms stream 115 comprising essentially pure n-butanol and a condensed isobutanol column overhead stream 116 comprising n-propanol, i-butanol, 2-butanol and n-butanol as major components.

Figure 5:
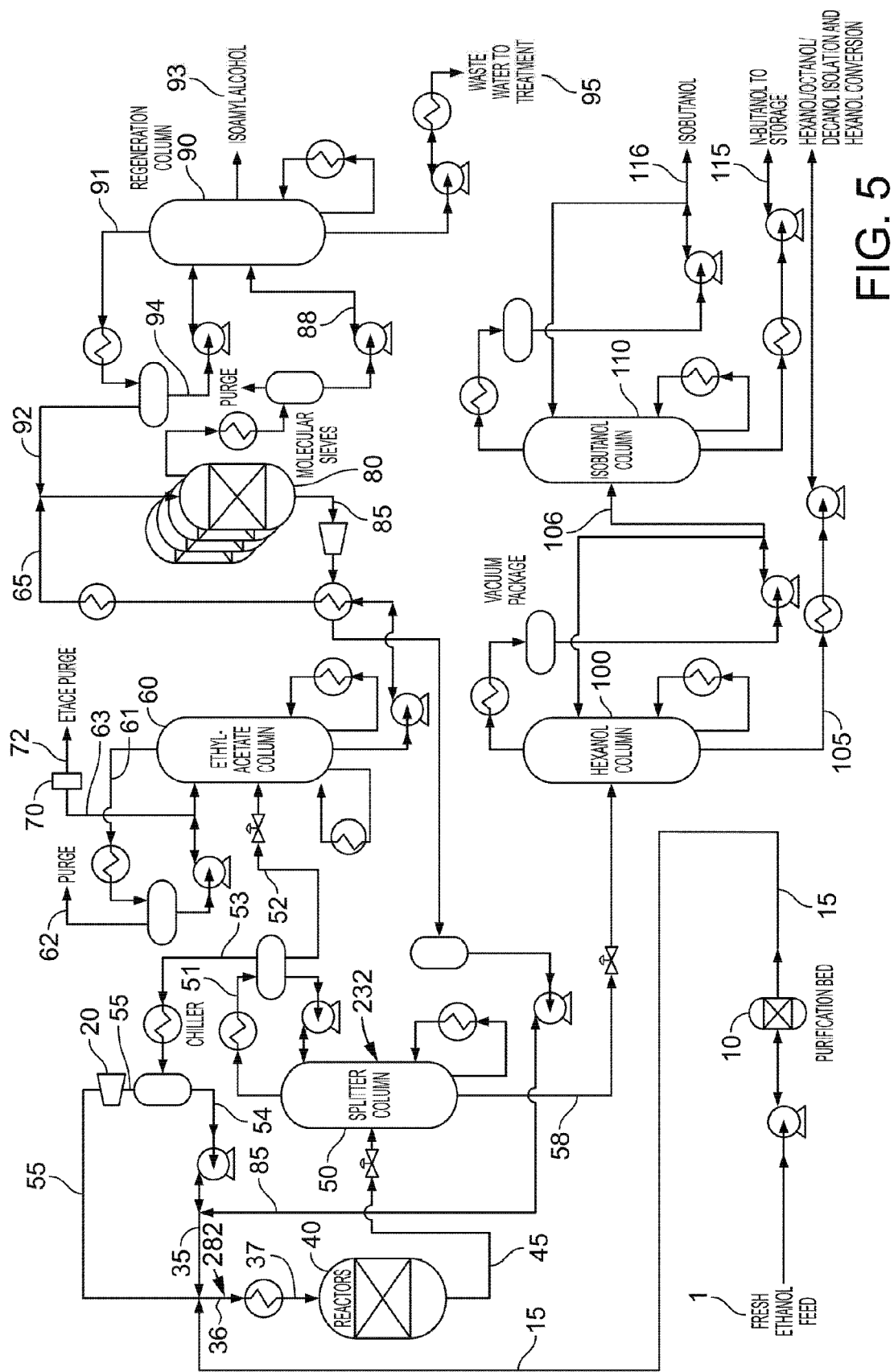
FIG. 5 is a process flow diagram of a fifth aspect of the present disclosure.

In another aspect of the present disclosure, depicted in FIG. 5, generally, ethanol is condensed in the presence of hydrogen by contact with a Guerbet catalyst to form a reactor product stream comprising n-butanol and n-hexanol. n-butanol and n-hexanol are isolated by fractionation and the recovered n-hexanol is condensed with ethanol in the presence hydrogen by contact with a Guerbet catalyst to form a reactor product stream comprising n-octanol. In particular, fresh ethanol feed 1 is optionally passed through purification bed 10 for removal of impurities (e.g., salts and ions) to form a fresh ethanol feed stream 15 comprising ethanol and water. In some aspects of the present disclosure, fresh ethanol may comprise isoamyl alcohol. Optionally, fresh ethanol feed 1 or fresh ethanol feed stream 15 may be fractionated in a fusel oil column (not depicted in FIG. 5) to generate a distilled fresh ethanol feed stream that may be fed directly to butanol reactor system 40 and octanol reactor system 230 and/or that may be combined with a recovered alcohol stream and dehydrated (such as by molecular sieves, a regeneration column and/or extractive distillation). Feed stream 15 is combined with splitter column second gas stream 55 comprising hydrogen (described below), recovered ethanol feed stream 35 (described below) to form reactor feed stream 36. In some optional aspects of the present disclosure, at least a portion of recovered n-hexanol 282 (see FIG. 2) or recovered n-hexanol 282 (see FIG. 3) and/or fresh n-hexanol may be added to the reactor feed stream. Reactor feed stream 36 is heated to form reactor feed vapor stream 37 that is sent to butanol reactor system 40 containing one reactor, or two or more reactors. In butanol reactor system 40, ethanol is contacted with a Guerbet catalyst under elevated pressure and temperature conditions to form reactor product stream 45. Reactor product stream 45 is fractionated in splitter column 50 to form splitter column bottoms stream 58 predominantly comprising high boiling compounds including n-butanol, i-butanol, n-hexanol, n-octanol and n-decanol and splitter column first overhead stream 51 comprising low boiling compounds including ethanol, acetaldehyde, ethyl acetate, hydrogen and carbon monoxide. In some aspects of the disclosure, the octanol reactor product stream 232 may be fractionated in splitter column 50. Splitter column first overhead stream 51 is passed through a condenser to form (i) first condensate stream 52 that is divided between splitter column 50 reflux and ethyl acetate column 60 feed and (ii) splitter column first gas stream 53. Splitter column gas stream 53 is passed through a second condenser to form splitter column second overhead condensate stream 54 and splitter column second gas stream 55. Splitter column second gas stream 55 is pressurized in recycle compressor 20 prior to combination with fresh ethanol feed stream 15 and recovered ethanol feed stream 35. In some further aspects of the present disclosure not depicted in FIG. 5, at least a portion of the hydrogen present in the reaction mixture is provided by a source of fresh hydrogen make-up. In some other aspects of the present disclosure, gas stream 55 is the source of hydrogen for the octanol reactor system as describe elsewhere herein. At least a portion of splitter column first condensate stream 52 is forwarded to ethyl acetate column 60 where it is fractionated to form ethyl acetate column bottoms stream 65 and ethyl acetate column overhead stream 61. Ethyl acetate column overhead stream 61 is passed through a condenser to form ethyl acetate column overhead gas purge stream 62 comprising acetaldehyde, hydrogen and ethyl acetate as major components and ethyl acetate column overhead condensate stream 63 comprising acetaldehyde, ethanol and ethyl acetate as major components. A portion of stream 63 is recycled to ethyl acetate column 60 and a portion of stream 63 is purged from the process. In one optional aspect of the present disclosure, stream 63 may be purified, such as by distillation column 70, to form purified ethyl acetate stream 72. Ethyl acetate column 60 bottoms stream 65 comprising and wet recovered ethanol stream 92 are processed in molecular sieves 80 to form water rich stream 88 and dry recovered ethanol stream 85 wherein stream 85 is characterized by the essential absence of acetaldehyde and very low water content. Dry recovered ethanol stream 85 is combined with splitter column second overhead stream 54 comprising ethanol and acetaldehyde to form recovered ethanol feed stream 35. In some aspects of the present disclosure, dry ethanol stream 85 is the source of ethanol for the octanol reactor system 230. Molecular sieve 80 water rich feed stream 88 comprising ethanol is fractionated in regeneration column 90. Regeneration column 90 separates water and isoamyl alcohol from ethanol to form regeneration column bottoms stream 95 comprising water that is sent to waste water treatment, isoamyl alcohol stream 93 and regeneration column overhead stream 91 that is passed through a condenser to form reflux stream 94 and wet ethanol stream 92 that is then sent to molecular sieve 80 inlet. Splitter column bottoms stream 58 is fractionated in hexanol column 100 to form hexanol column bottoms stream 105 comprising n-hexanol, n-octanol and n-decanol as major components and hexanol column condenser overhead stream 106 comprising n-butanol and minor amounts of n-propanol, i-butanol and 2-butanol. Hexanol column bottoms stream 105 is fractionated in hexanol/octanol/decanol purification system 210 (such as depicted, for instance and without limitation, in FIGS. 2 and 3) to form recovered n-hexanol stream 282 (FIG. 2) or 282 (FIG. 3). As further described elsewhere herein (such as depicted, for instance, in FIGS. 2 and 3), recovered n-hexanol is combined with a source of ethanol and a source of hydrogen and contacted with a heterogeneous catalyst in octanol reactor system 230 under elevated temperature and pressure conditions to form n-octanol and n-decanol. Hexanol column condensed overhead stream 106 is fractionated in isobutanol column 110 to form a isobutanol column bottoms stream 115 comprising essentially pure n-butanol and a condensed hexanol column overhead stream 116 comprising n-propanol, i-butanol, 2-butanol and n-butanol as major components.

Figure 6:
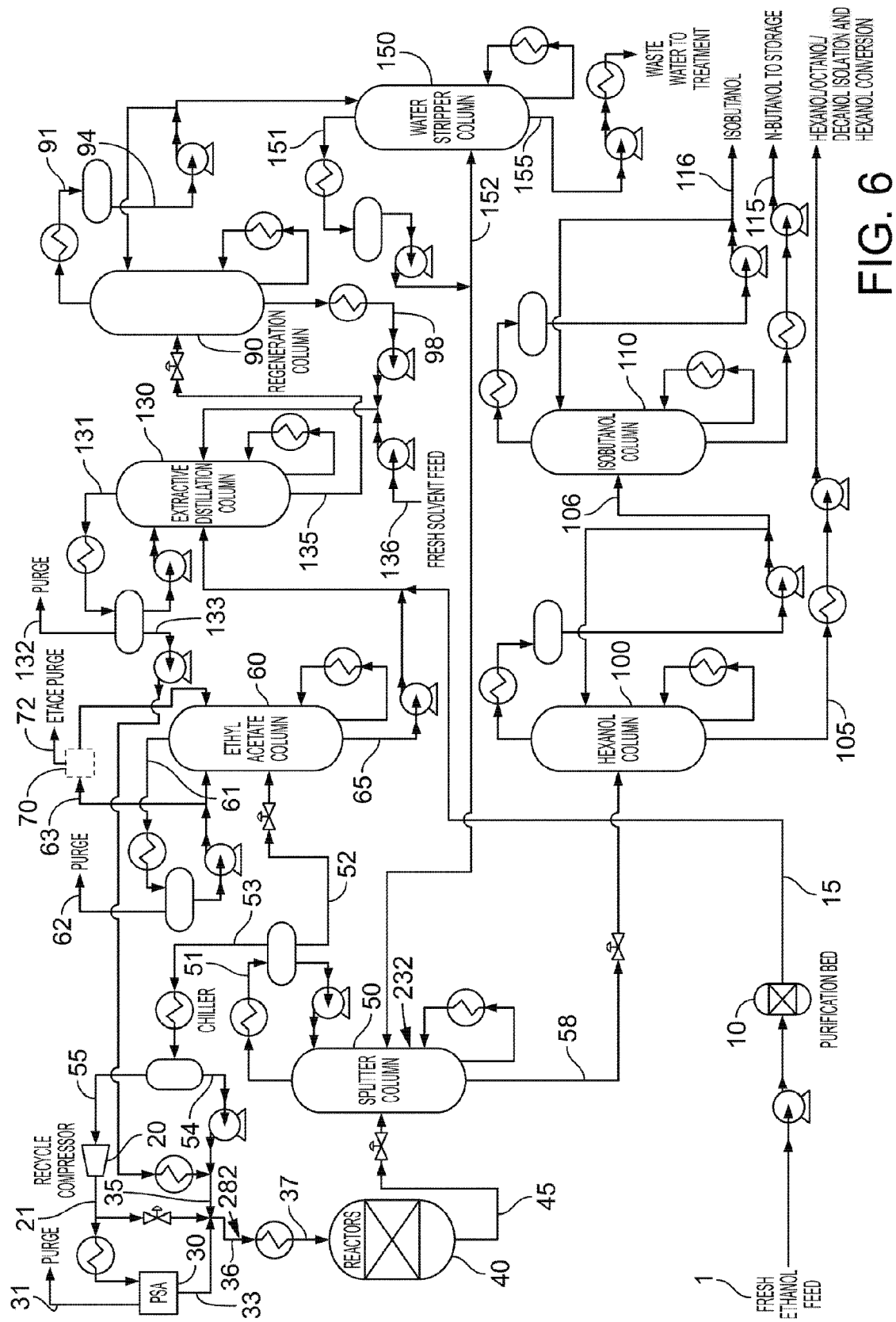
FIG. 6 is a process flow diagram of a sixth aspect of the present disclosure.

In another aspect of the present disclosure, depicted in FIG. 6, generally, ethanol is condensed in the presence of hydrogen by contact with a Guerbet catalyst to form a reactor product stream comprising n-butanol and n-hexanol. n-butanol and n-hexanol are isolated by fractionation and the recovered n-hexanol is condensed with ethanol in the presence hydrogen by contact with a Guerbet catalyst to form a reactor product stream comprising n-octanol. In particular, fresh ethanol feed 1 is optionally passed through purification bed 10 for removal of impurities (e.g., salts and ions) to form a fresh ethanol feed stream 15 comprising ethanol and water. In some aspects of the present disclosure, fresh ethanol may comprise isoamyl alcohol. Optionally, fresh ethanol feed 1 or fresh ethanol feed stream 15 may be fractionated in a fusel oil column (not depicted in FIG. 6) to generate a distilled fresh ethanol feed stream that may be fed directly to butanol reactor system 40 and octanol reactor system 230 and/or that may be combined with a recovered alcohol stream and dehydrated (such as by molecular sieves, a regeneration column and/or extractive distillation). Feed stream 15 is sent to extractive distillation column 130 inlet. Ethyl acetate column bottom stream 65 (comprising ethanol and water) is also sent to extractive distillation column 130 inlet. The combined streams are contacted with an extractive solvent in extractive distillation column 130 to form extractive distillation column overhead stream 131 and bottoms stream 135. Overhead stream 131 is passed through a condenser to form dry ethanol feed stream 133 and purge stream 132. Bottoms stream 135 comprising contaminated extractive solvent is fractionated in regeneration column 90 to generate a bottoms stream comprising recovered extractive solvent 98 that is transferred to extractive distillation column 130. Extractive solvent make-up to extractive distillation column 130 is done via fresh extractive solvent feed 136. Regeneration column overhead stream 91 is passed through a condenser to form regeneration column condensed overhead stream 94 that is rich in water. At least a portion of stream 94 may be refluxed to column 130 and at least a portion is fed to water striper column 150 for removal of organic components therefrom as water stripper column overhead stream 151 that is passed through a condenser to form stream 152. At least a portion of stream 152 may be refluxed to water stripper column 150 and at least a portion is transferred to splitter column 50. Water stripper column bottoms stream 155 is discharged to waste water treatment. Dry ethanol feed stream 133 is combined with splitter column second overhead stream 54 comprising ethanol and acetaldehyde to form mixed ethanol feed stream 35. In some aspects of the present disclosure, dry ethanol stream 133 is the source of ethanol for the octanol reactor system 230. Mixed alcohol feed stream 35 is combined with gas stream 33 comprising hydrogen to form reactor feed stream 36. In some optional aspects of the present disclosure, at least a portion of recovered n-hexanol 282 (see FIG. 2) or recovered n-hexanol 282 (see FIG. 3) and/or fresh n-hexanol may be added to the reactor feed stream. In some further aspects of the present disclosure not depicted in FIG. 6, at least a portion of the hydrogen present in the reaction mixture is provided by a source of fresh hydrogen make-up. In some other aspects of the present disclosure, gas stream 33 is the source of hydrogen for the octanol reactor system as described elsewhere herein. Reactor feed stream 36 is heated to form reactor feed vapor stream 37 that is sent to butanol reactor system 40 containing or reactor, or two or more reactors. In butanol reactor system 40, ethanol is contacted with a Guerbet catalyst under elevated pressure and temperature conditions to form reactor product stream 45. Reactor product stream 45 is fractionated in splitter column 50 to form splitter column bottoms stream 58 predominantly comprising high boiling compounds including n-butanol, i-butanol, n-hexanol, n-octanol and n-decanol and splitter column first overhead stream 51 comprising lower boiling compounds including ethanol, acetaldehyde, ethyl acetate, hydrogen and carbon monoxide. In some aspects of the disclosure, the octanol reactor product stream 232 may be fractionated in splitter column 50. Splitter column first overhead stream 51 is passed through a condenser to form condensate stream 52.

At least a portion of condensate stream 52 may be refluxed to splitter column 50 and as least a portion is fed forward to ethyl acetate column 60 where it is fractionated to form ethyl acetate column bottoms stream 65 and ethyl acetate column overhead stream 61. In some optional aspects of the present disclosure, at least a portion of condensate stream 52 may be purged from the process. Splitter column gas stream 53 passed through a heat exchanger to form splitter column second overhead stream 54 and splitter column second gas stream 55. Splitter column second gas stream 55 is pressurized in recycle compressor 20. In some aspects of the present disclosure, compressed splitter column second gas stream 21 may be the gas source for gas stream 33. In some other aspects of the present disclosure, compressed splitter column second gas stream 21 may be processed by pressure swing adsorption 30 to form gas stream 33 and purge stream 31 comprising hydrogen, carbon dioxide, carbon monoxide and ethane. In some other aspects of the present disclosure, a combination of compressed splitter column second gas stream 21 and gas stream 33 are the gas source for butanol reactor system 40. Ethyl acetate column overhead stream 61 is passed through a condenser to form ethyl acetate column overhead gas purge stream 62 comprising acetaldehyde, hydrogen and ethyl acetate as major components and ethyl acetate column overhead condensate stream 63 comprising acetaldehyde, ethanol and ethyl acetate as major components. A portion of stream 63 is recycled to ethyl acetate column 60 and a portion of stream 63 is purged from the process. In one optional aspect of the present disclosure, stream 63 may be purified, such as by distillation column 70, to form purified ethyl acetate stream 72. Splitter column bottoms stream 58 is fractionated in hexanol column 100 to form hexanol column bottoms stream 105 comprising n-hexanol, n-octanol and n-decanol as major components and hexanol column overhead stream 106 comprising n-butanol and minor amounts of n-propanol, i-butanol and 2-butanol. Hexanol column bottoms stream 105 is fractionated in hexanol/octanol/decanol purification system 210 (such as depicted, for instance and without limitation, in FIGS. 2 and 3) to form recovered n-hexanol stream 282 (FIG. 2) or 282 (FIG. 3). As further described elsewhere herein (such as depicted, for instance, in FIGS. 2 and 3), recovered n-hexanol is combined with a source of ethanol and a source of hydrogen and contacted with a heterogeneous catalyst in octanol reactor system 230 under elevated temperature and pressure conditions to form n-octanol and n-decanol. Hexanol column overhead stream 106 is fractionated in isobutanol column 110 to form a isobutanol column bottoms stream 115 comprising essentially pure n-butanol and a condensed isobutanol column overhead stream 116 comprising n-propanol, i-butanol, 2-butanol and n-butanol as major components.

Figure 7:
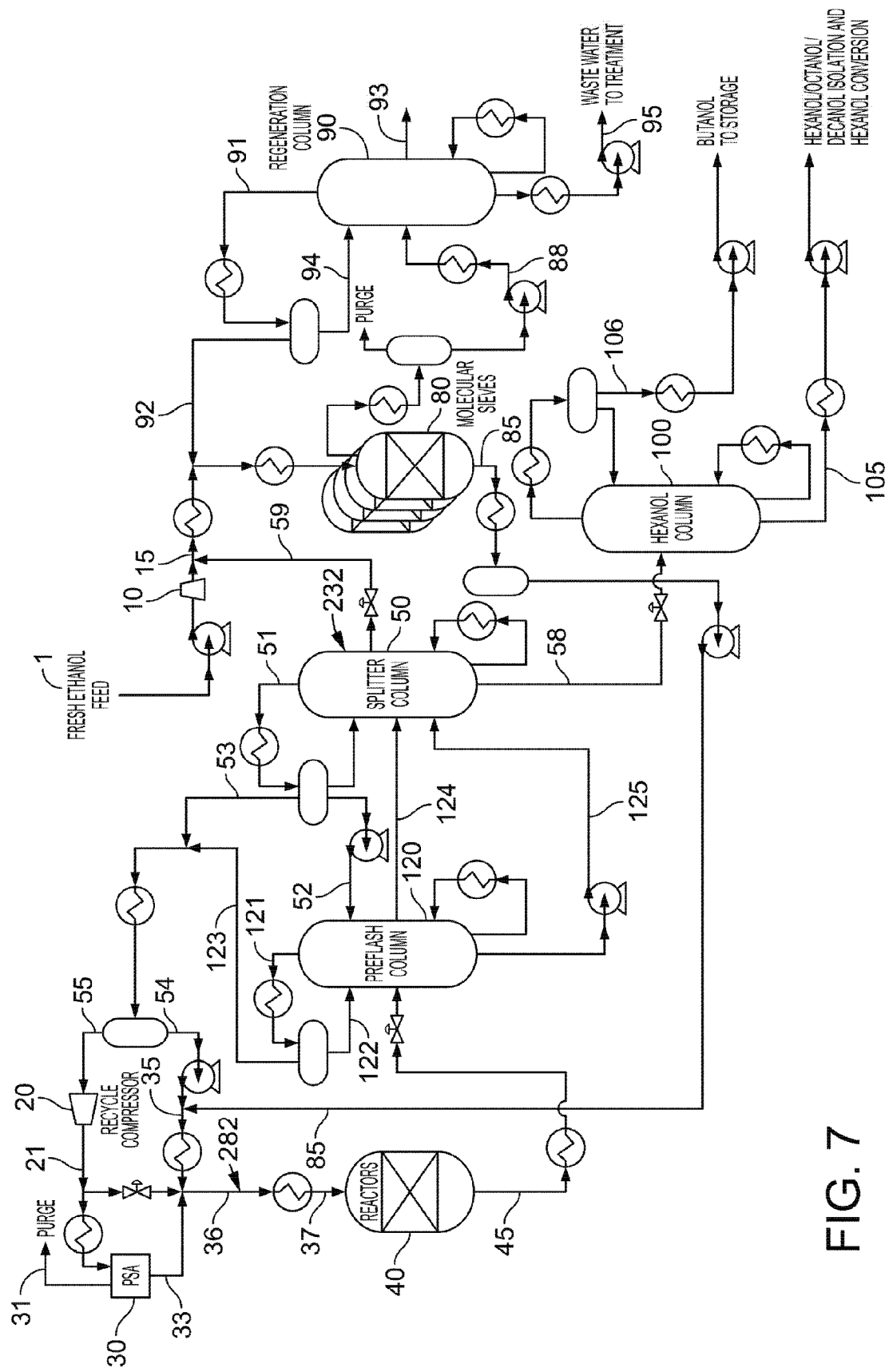
FIG. 7 is a process flow diagram of a seventh aspect of the present disclosure.

In another aspect of the present disclosure, depicted in FIG. 7, generally, ethanol is condensed in the presence of hydrogen by contact with a Guerbet catalyst to form a reactor product stream comprising n-butanol and n-hexanol, n-butanol and n-hexanol are isolated by fractionation and the recovered n-hexanol is condensed with ethanol in the presence hydrogen by contact with a Guerbet catalyst to form a reactor product stream comprising n-octanol. In particular, fresh ethanol feed 1 is optionally passed through purification bed 10 for removal of impurities (e.g., salts and ions) to form a fresh ethanol feed stream 15 comprising ethanol and water. In some aspects of the present disclosure, fresh ethanol may comprise isoamyl alcohol. Optionally, fresh ethanol feed 1 or fresh ethanol feed stream 15 may be fractionated in a fusel oil column (not depicted in FIG. 7) to generate a distilled fresh ethanol feed stream that may be fed directly to butanol reactor system 40 and octanol reactor system 230 and/or that may be combined with a recovered alcohol stream and dehydrated (such as by molecular sieves, a regeneration column and/or extractive distillation). Feed stream 15 is sent to molecular sieve 80 inlet. Splitter column 50 intermediate stream 59 (comprising ethanol and water) and regeneration column 90 wet ethanol stream 92 are also sent to molecular sieve 80 inlet. The combined streams are processed in molecular sieves 80 to form water rich feed stream 88 and dry ethanol stream 85. Molecular sieve water rich feed stream 88 is fractionated in regeneration 90 for the separation of water and isoamyl alcohol from ethanol to form regeneration column bottoms stream 95 comprising water that is sent to waste water treatment, isoamyl alcohol stream 93 and regeneration column overhead stream 91 that is passed through a condenser to form reflux stream 94 and wet ethanol stream 92 that is then sent to molecular sieve 80 inlet. Dry ethanol stream 85 is combined with splitter column second overhead stream 54 comprising ethanol and acetaldehyde to form mixed ethanol feed stream 35. In some aspects of the present disclosure, dry ethanol stream 85 is the source of ethanol for the octanol reactor system 230. Mixed alcohol feed stream 35 is combined with gas stream 33 comprising hydrogen to form reactor feed stream 36. In some optional aspects of the present disclosure, at least a portion of recovered n-hexanol 282 (see FIG. 2) or recovered n-hexanol 282 (see FIG. 3) and/or fresh n-hexanol by be added to the reactor feed stream. In some further aspects of the present invention not depicted in FIG. 7, at least a portion of the hydrogen present in the reaction mixture is provided by a source of fresh hydrogen make-up. In some other aspects of the present disclosure, gas stream 33 is the source of hydrogen for the octanol reactor system as described elsewhere herein. Reactor feed stream 36 is heated to form reactor feed vapor stream 37 that is sent to butanol reactor system 40 containing one reactor, or two or more reactors. In butanol reactor system 40, ethanol is contacted with a Guerbet catalyst under elevated pressure and temperature conditions to form reactor product stream 45. Reactor product stream 45 is fractionated in preflash column 120 to form preflash column bottoms stream 125, preflash column mid-cut stream 124 and preflash column overhead stream 121. Preflash column overhead stream 121 is passed through a condenser to form a condensate stream 122 and preflash column gas stream 123. In some aspects of the present disclosure not depicted in FIG. 7, at least a portion of preflash column condensate stream 122 and/or gas stream 123 may be purged from the process. Preflash column bottoms stream 125 and mid-cut stream 124 are sent to splitter column 50 to form splitter column bottoms stream 58 predominantly comprising high boiling compounds including n-butanol, i-butanol, n-hexanol, n-octanol and n-decanol, splitter column mid-cut stream 59 comprising ethanol and water, and splitter column first overhead stream 51 comprising lower boiling compounds including ethanol, acetaldehyde, ethyl acetate, hydrogen and carbon monoxide. In some aspects of the disclosure, the octanol reactor product stream 232 may be fractionated in splitter column 50. Splitter column first overhead stream 51 is passed through a condenser to form condensate stream 52 that is recycled to preflash column 120 and/or to splitter column 50. In some optional aspects of the present disclosure, at least a portion of condensate stream 52 may be purged from the process. Splitter column gas stream 53 is combined with preflash column gas stream 123 and further condensed to form splitter column second overhead stream 54 and splitter column second gas stream 55. Splitter column second gas stream 55 is pressurized in recycle compressor 20. In some aspects of the present disclosure, compressed splitter column second gas stream 21 may be the gas source for gas stream 33. In some other aspects of the present disclosure, compressed splitter column second gas stream 21 may be processed by pressure swing adsorption 30 to form gas stream 33 and purge stream 31 comprising hydrogen, carbon dioxide, carbon monoxide and ethane. In some other aspects of the present disclosure, a combination of compressed splitter column second gas stream 21 and gas stream 33 are the gas source for butanol reactor system 40. Splitter column bottoms stream 58 is fractionated in hexanol column 100 to form hexanol column bottoms stream 105 comprising n-hexanol, n-octanol and n-decanol as major components and hexanol column condensed overhead stream 106 comprising n-butanol and minor amounts of n-propanol, i-butanol and 2-butanol. Hexanol column bottoms stream 105 is fractionated in hexanol/octanol/decanol purification system 210 (such as depicted, for instance and without limitation, in FIGS. 2 and 3) to form recovered n-hexanol stream 282 (FIG. 2) or 282 (FIG. 3). As further described elsewhere herein (such as depicted, for instance, in FIGS. 2 and 3), recovered n-hexanol is combined with a source of ethanol and a source of hydrogen and contacted with a heterogeneous catalyst in octanol reactor system 230 under elevated temperature and pressure conditions to form n-octanol and n-decanol. Optionally, and not depicted in FIG. 7, hexanol column condensed overhead stream 106 may be fractionated in an isobutanol column to form a hexanol column bottoms stream comprising essentially pure n-butanol and a condensed hexanol column overhead stream comprising n-propanol, i-butanol, 2-butanol and n-butanol as major components.

Figure 8:
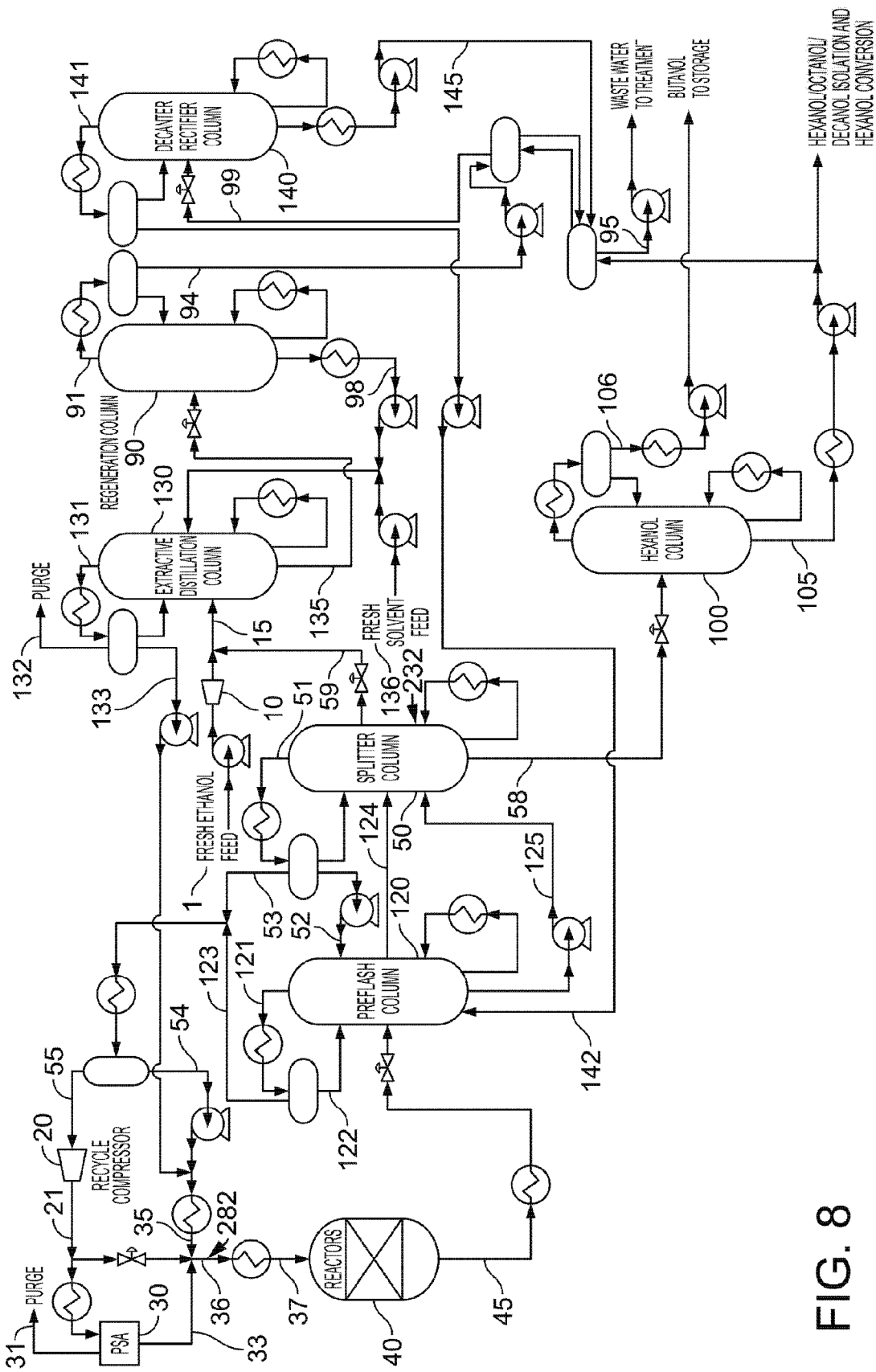
FIG. 8 is a process flow diagram of an eighth aspect of the present disclosure.

In another aspect of the present disclosure, depicted in FIG. 8, generally, ethanol is condensed in the presence of hydrogen by contact with a Guerbet catalyst to form a reactor product stream comprising n-butanol and n-hexanol. n-butanol and n-hexanol are isolated by fractionation and the recovered n-hexanol is condensed with ethanol in the presence hydrogen by contact with a Guerbet catalyst to form a reactor product stream comprising n-octanol. In particular, fresh ethanol feed 1 is optionally passed through purification bed 10 for removal of impurities (e.g., salts and ions) to form a fresh ethanol feed stream 15 comprising ethanol and water. In some aspects of the present disclosure, fresh ethanol may comprise isoamyl alcohol. Optionally, fresh ethanol feed 1 or fresh ethanol feed stream 15 may be fractionated in a fusel oil column (not depicted in FIG. 8) to generate a distilled fresh ethanol feed stream that may be fed directly to butanol reactor system 40 and octanol reactor system 230 and/or that may be combined with a recovered alcohol stream and dehydrated (such as by molecular sieves, a regeneration column and/or extractive distillation). Feed stream 15 is sent to extractive distillation column 130 inlet. Splitter column intermediate stream 59 (comprising ethanol and water) is also sent to extractive distillation column 130 inlet. The combined streams are fractionated by contact with an extractive solvent in extractive distillation column 130 to form extractive distillation column overhead stream 131 and bottoms stream 135. Overhead stream 131 is passed through a condenser to form dry ethanol feed stream 133 and purge stream 132. Bottoms stream 135 comprising contaminated extractive solvent is sent to regeneration column 90 to generate a bottoms stream comprising recovered extractive solvent 98 that is transferred to extractive distillation column 130. Extractive solvent make-up to extractive distillation column 130 is done via fresh solvent feed 136. Column overhead stream 91 is passed through a condenser to form regeneration column condensed overhead stream 94 that is rich in water. At least a portion of stream 94 may be refluxed to column 90 and at least a portion may be discharged to waste water treatment 95. Decanter rectifier column 140 receives various streams containing organic components including regeneration column condensed overhead stream 94, hexanol column bottoms stream 105, and decanter rectifier column bottoms stream 145, depicted as combined stream 99, and strips organic components therefrom as decanter rectifier overhead stream 141 that is passed through a condenser and recycled to preflash column 120 as stream 142. At least a portion of rectifier column bottoms stream 145 is discharged to waste water treatment 95. Dry ethanol feed stream 133 is combined with splitter column second overhead stream 54 comprising ethanol and acetaldehyde to form mixed ethanol feed stream 35. In some aspects of the present disclosure, dry ethanol stream 133 is the source of ethanol for the octanol reactor system 230. Mixed alcohol feed stream 35 is combined with gas stream 33 comprising hydrogen to form reactor feed stream 36. In some optional aspects of the present disclosure, at least a portion of recovered n-hexanol 282 (see FIG. 2) or recovered n-hexanol 282 (see FIG. 3) and/or fresh n-hexanol may be added to the reactor feed stream. In some further aspects of the present invention not depicted in FIG. 8, at least a portion of the hydrogen present in the reaction mixture is provided by a source of fresh hydrogen make-up. In some other aspects of the present disclosure, gas stream 33 is the source of hydrogen for the octanol reactor system as described elsewhere herein. Reactor feed stream 36 is heated to form reactor feed vapor stream 37 that is sent to butanol reactor system 40 containing one reactor, or two or more reactors. In butanol reactor system 40, ethanol is contacted with a Guerbet catalyst under elevated pressure and temperature conditions to form reactor product stream 45. Reactor product stream 45 is fractionated in preflash column 120 to form preflash column bottoms stream 125, preflash column mid-cut stream 124 and preflash column overhead stream 121. Preflash column overhead stream 121 is passed through a condenser to form a condensate stream 122 and preflash column gas stream 123. In some aspects of the present disclosure not depicted in FIG. 8, at least a portion of preflash column condensate stream 122 and/or gas stream 123 may be purged from the process. Preflash column bottoms stream 125 and mid-cut stream 124 are sent to splitter column 50 to and are fractionated to form splitter column bottoms stream 58 predominantly comprising high boiling compounds including n-butanol, i-butanol, n-hexanol, n-octanol and n-decanol, splitter column mid-cut stream 59 comprising ethanol and water, and splitter column first overhead stream 51 comprising lower boiling compounds including ethanol, acetaldehyde, ethyl acetate, hydrogen and carbon monoxide. In some aspects of the disclosure, the octanol reactor product stream 232 may be fractionated in splitter column 50. Splitter column first overhead stream 51 is passed through a condenser to form condensate stream 52 that is recycled to preflash column 120 and/or to splitter column 50. In some optional aspects of the present disclosure, at least a portion of condensate stream 52 may be purged from the process. Splitter column gas stream 53 is combined with preflash column gas stream 123 and further condensed to form splitter column second overhead stream 54 and splitter column second gas stream 55. Splitter column second gas stream 55 is pressurized in recycle compressor 20. In some aspects of the present disclosure, compressed splitter column second gas stream 21 may be the gas source for gas stream 33. In some other aspects of the present disclosure, compressed splitter column second gas stream 21 may be processed by pressure swing adsorption 30 to form gas stream 33 and purge stream 31 comprising hydrogen, carbon dioxide, carbon monoxide and ethane. In some other aspects of the present disclosure, a combination of compressed splitter column second gas stream 21 and gas stream 33 are the gas source for butanol reactor system 40. Splitter column bottoms stream 58 is fractionated in hexanol column 100 to form hexanol column bottoms stream 105 comprising n-hexanol, n-octanol and n-decanol as major components and hexanol column condensed overhead stream 106 comprising n-butanol and minor amounts of n-propanol, i-butanol and 2-butanol. Hexanol column bottoms stream 105 is fractionated in hexanol/octanol/decanol purification system 210 (such as depicted, for instance and without limitation, in FIGS. 2 and 3) to form recovered n-hexanol stream 282 (FIG. 2) or 282 (FIG. 3). As further described elsewhere herein (such as depicted, for instance, in FIGS. 2 and 3), recovered n-hexanol is combined with a source of ethanol and a source of hydrogen and contacted with a heterogeneous catalyst in octanol reactor system 230 under elevated temperature and pressure conditions to form n-octanol and n-decanol. Optionally, and not depicted in FIG. 8, hexanol column condense overhead stream 106 may be fractionated in an isobutanol column to form a hexanol column bottoms stream comprising essentially pure n-butanol and a condensed hexanol column overhead stream comprising n-propanol, i-butanol, 2-butanol and n-butanol as major components.

Figure 9:
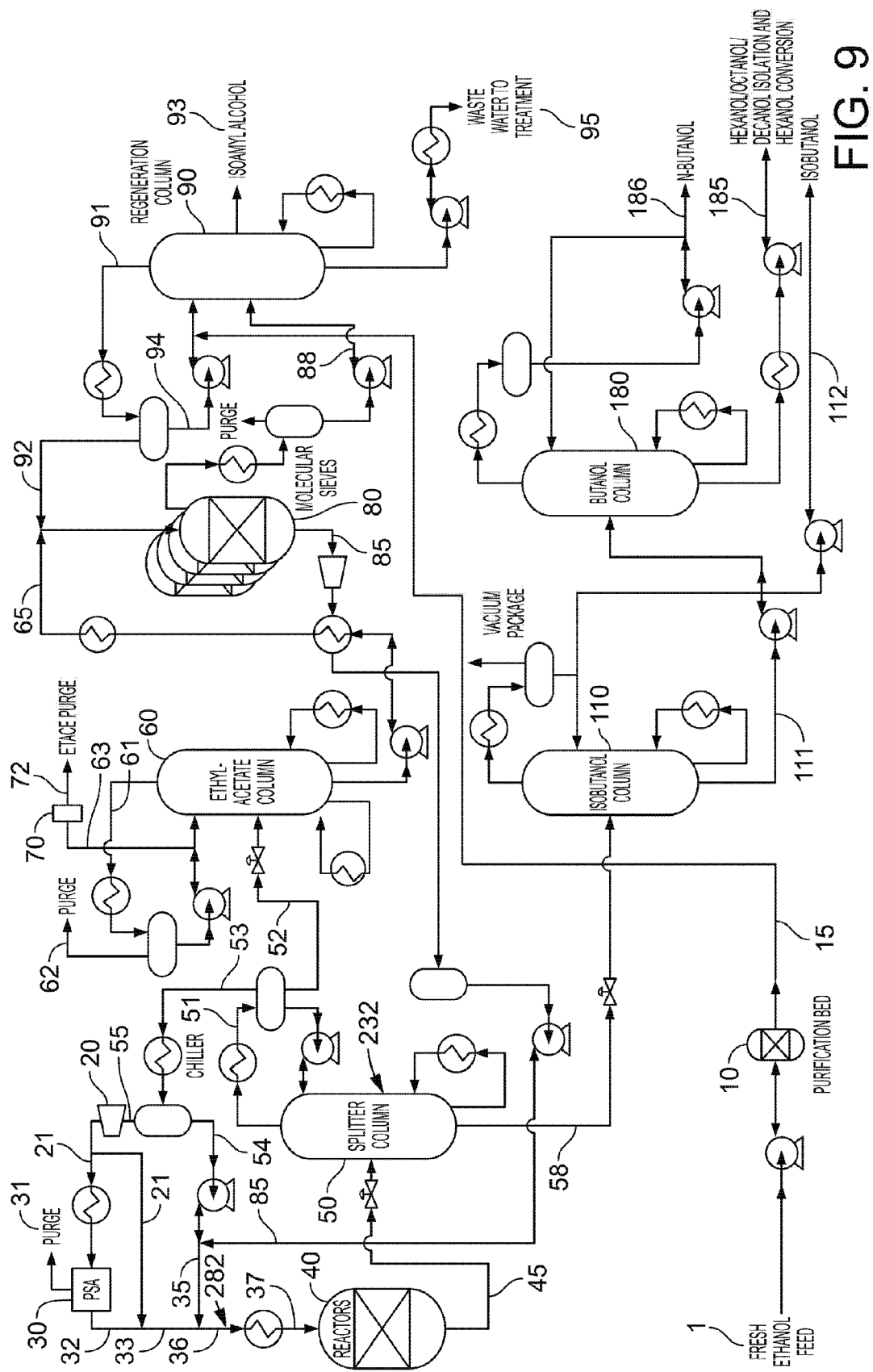
FIG. 9 is a process flow diagram of a ninth aspect of the present disclosure.

In another aspect of the present disclosure, depicted in FIG. 9, splitter column bottoms stream 58 may be processed in an alternate fractionation aspect to form n-butanol, i-butanol, n-hexanol, n-octanol and n-decanol streams. Although FIG. 9 is depicted in reference to the process arrangement of FIG. 4, the FIG. 9 fractionation aspect of the present disclosure can be applied to any aspect of the present disclosure for the fractionation of a process stream comprising n-butanol, i-butanol, n-hexanol, n-octanol and n-decanol such as the aspects of the present disclosure depicted in FIGS. 5 to 8. In the FIG. 9 fractionation aspect of the present disclosure, splitter column bottoms stream 58 is processed in isobutanol column 110 to form isobutanol column bottoms stream 111 comprising n-butanol and hexanol as major components and isobutanol column condenser overhead stream 112 predominantly comprising i-butanol. At least a portion of isobutanol column condenser overhead stream 112 may be refluxed to isobutanol column 110 and at least a portion may be purged from the process. Isobutanol column bottoms stream 111 is processed in butanol column 180 to form a butanol column bottoms stream 185 predominantly comprising hexanol and a butanol column overhead stream 186 comprising essentially pure n-butanol. At least a portion of butanol column overhead stream 186 may be refluxed to butanol column 180.

Figure 10:
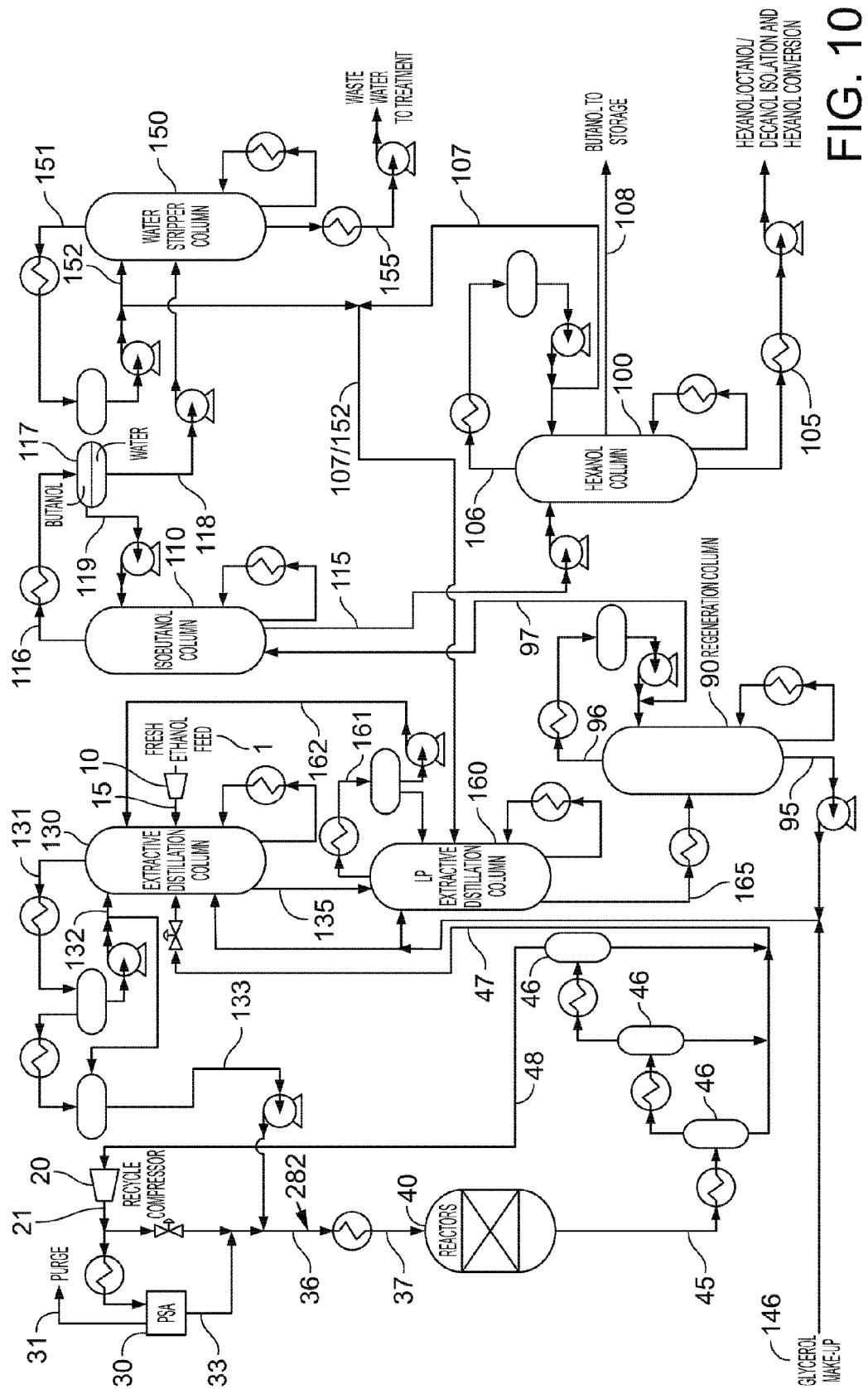
FIG. 10 is a process flow diagram of a tenth aspect of the present disclosure.

In another aspect of the present disclosure, depicted in FIG. 10, generally, ethanol is condensed in the presence of hydrogen by contact with a Guerbet catalyst to form a reactor product stream comprising n-butanol and n-hexanol, n-butanol and n-hexanol are isolated by fractionation and the recovered n-hexanol is condensed with ethanol in the presence hydrogen by contact with a Guerbet catalyst to form a reactor product stream comprising n-octanol. In particular, fresh ethanol feed 1 is optionally passed through purification bed 10 for removal of impurities (e.g., salts and ions) to form a fresh ethanol feed stream 15 comprising ethanol and water. In some aspects of the present disclosure, fresh ethanol further comprises isoamyl alcohol. Optionally, fresh ethanol feed 1 or fresh ethanol feed stream 15 may be fractionated in a fusel oil column (not depicted in FIG. 10) to generate a distilled fresh ethanol feed stream that may be fed directly to butanol reactor system 40 and octanol reactor system 230 and/or that may be combined with a recovered alcohol stream and dehydrated (such as by molecular sieves, a regeneration column and/or extractive distillation). Feed stream 15 is sent to extractive distillation column 130 inlet. Reactor condensate stream 47 and extractive distillation column overhead stream 162 are also fed to extractive distillation column 130. The combined streams are contacted with glycerol in extractive distillation column 130 at a higher pressure than the pressure used in low pressure extractive distillation column 160 to form extractive distillation column overhead stream 131 and bottoms stream 135. For instance, the pressure in extractive distillation column 130 may be at least about 3 bara higher than pressure in low pressure extractive distillation column 160. Overhead stream 131 is passed through a first condenser to form extractive distillation column condensate stream 132 and a gas stream. FIG. 10 depicts passing the gas stream through a second condenser to form an extractive distillation column second condensate stream 133. Condensate stream 132 may optionally refluxed to extractive distillation column 130 and/or be combined with second extractive distillation column condensate stream 133. Although not depicted in FIG. 10, one or more gas purge and/or liquid purge streams may be present in the extractive distillation column 130 overhead system to purge ethyl acetate and acetaldehyde from the process. Extractive distillation column second condensate stream 133 comprises essentially pure dry ethanol and is the ethanol feedstock for butanol reactor system 40. In some aspects of the present disclosure, extractive distillation column second condensate stream 133 is the source of ethanol for the octanol reactor system 230. Reactor product stream 45 generated in butanol reactor system 40 may be passed through one or more condensers and fed forward to separation tank system 46 to form gas stream 48 comprising hydrogen, water, carbon dioxide, carbon monoxide and acetaldehyde and condensate stream 47 comprising n-butanol, ethanol, water, acetaldehyde and ethyl acetate. Gas stream 48 is pressurized in recycle compressor 20 to form compressed splitter column second gas stream 21. In some aspects of the present disclosure, compressed splitter column second gas stream 21 may be the gas source for gas stream 33. In some other aspects of the present disclosure, compressed splitter column second gas stream 21 may be processed by pressure swing adsorption 30 to form gas stream 33 and purge stream 31 comprising hydrogen, carbon dioxide, carbon monoxide and methane. In some other aspects of the present disclosure, a combination of compressed splitter column second gas stream 21 and gas stream 33 are the gas source for butanol reactor system 40. Extractive distillation column second condensate stream 133 is combined with gas stream 33 comprising hydrogen to form reactor feed stream 36. In some optional aspects of the present disclosure, at least a portion of recovered n-hexanol 282 (see FIG. 2) or recovered n-hexanol 282 (see FIG. 3) and/or fresh n-hexanol by be added to the reactor feed stream. In some further aspects of the present invention not depicted in FIG. 10, at least a portion of the hydrogen present in the reaction mixture is provided by a source of fresh hydrogen make-up. In some other aspects of the present disclosure, gas stream 33 is the source of hydrogen for the octanol reactor system as describe elsewhere herein.

Reactor feed stream 36 is heated and pressurized to form reactor feed vapor stream 37 that is sent to butanol reactor system 40 containing one reactor, or two or more reactors. In butanol reactor system 40, ethanol is contacted with a Guerbet catalyst under elevated pressure and temperature conditions to form reactor product stream 45. Extractive distillation column 130 bottoms stream 135 comprising glycerol and n-butanol is fed to low pressure extractive distillation column 160 where the mixture is subjected to a second, lower pressure, distillation. Overhead stream 161 is passed through a condenser to form stream 162 that is refluxed to low pressure extractive distillation column 160 and/or refluxed to extractive distillation column 130. Low pressure extractive distillation column bottoms 165 are fed to regeneration column 90 where organic materials are stripped into overhead steam 96 and glycerol is recovered in bottoms stream 95. Bottoms stream 95 is recycled to extractive distillation columns 130 and/or 160 and fresh glycerol make-up 146 is added as required. In some aspects of the disclosure, not depicted in FIG. 10, the octanol reactor product stream 232 may be fractionated in extractive distillation column 130 or in extractive distillation column 160. Regeneration column overhead stream 96 is passed through a condenser to form regeneration column overhead condensate stream 97 comprising n-butanol, hexanol and water. At least a portion of condensate stream 97 may be refluxed to regeneration column 90 and at least a portion is fed to isobutanol column 110. In isobutanol column 110, overhead stream 116 is formed comprising an azeotrope of butanol and water that is collected in separation vessel 117 as butanol phase 119 and water phase 118. Butanol phase 119 is refluxed to isobutanol column 110 and water phase 118 is fed to water stripper column 150. Organic compounds are stripped from water phase 118 to form overhead stream 151 that is passed through a condenser to form overhead stream 152. At least a portion of overhead stream 152 is refluxed to water stripper column 150 and at least a portion is fed to low pressure extractive distillation column 160. Extractive distillation bottoms stream 155 is processed in waste water treatment. Isobutanol column bottoms stream 115 is fed to hexanol column 100 for the separation of butanol from hexanol. In hexanol column 100, bottoms stream 105 comprising n-hexanol, n-octanol and n-decanol and intermediate cut stream 108 comprising essentially pure butanol are formed. Hexanol column bottoms stream 105 is fractionated in hexanol/octanol/decanol purification system 210 (such as depicted, for instance and without limitation, in FIGS. 2 and 3) to form recovered n-hexanol stream 282 (FIG. 2) or 282 (FIG. 3). As further described elsewhere herein (such as depicted, for instance, in FIGS. 2 and 3), recovered n-hexanol is combined with a source of ethanol and a source of hydrogen and contacted with a heterogeneous catalyst in octanol reactor system 230 under elevated temperature and pressure conditions to form n-octanol and n-decanol. An overhead stream 106 is formed comprising water and low boiling organic compounds that is passed through a condenser to form overhead stream 107. Overhead stream 107 may be fed to low pressure extractive distillation column 160 and/or to water stripper column 150.

Figure 11:
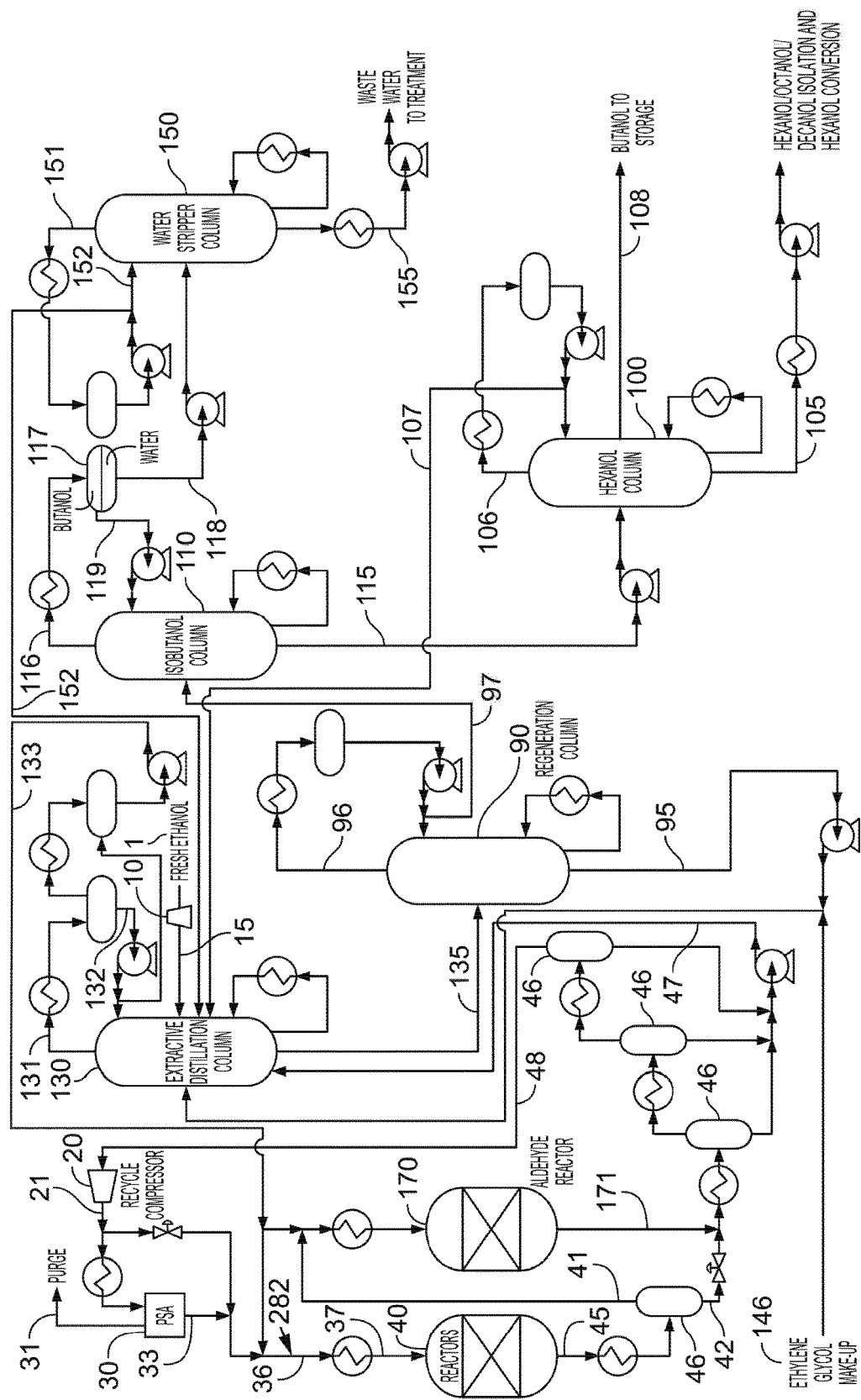
FIG. 11 is a process flow diagram of an eleventh aspect of the present disclosure.

In another aspect of the present disclosure, depicted in FIG. 11, generally, ethanol is condensed in the presence of hydrogen by contact with a Guerbet catalyst to form a reactor product stream comprising n-butanol and n-hexanol. n-butanol and n-hexanol are isolated by fractionation and the recovered n-hexanol is condensed with ethanol in the presence hydrogen by contact with a Guerbet catalyst to form a reactor product stream comprising n-octanol. In particular, fresh ethanol feed 1 is optionally passed through purification bed 10 for removal of impurities (e.g., salts and ions) to form a fresh ethanol feed stream 15 comprising ethanol and water. In some aspects of the present disclosure, fresh ethanol may comprise isoamyl alcohol. Optionally, fresh ethanol feed 1 or fresh ethanol feed stream 15 may be fractionated in a fusel oil column (not depicted in FIG. 11) to generate a distilled fresh ethanol feed stream that may be fed directly to butanol reactor system 40 and octanol reactor system 230 and/or that may be combined with a recovered alcohol stream and dehydrated (such as by molecular sieves, a regeneration column and/or extractive distillation). Feed stream 15 is sent to extractive distillation column 130 inlet. Water stripper column overhead stream 152 and hexanol column overhead stream 107 are also fed to extractive distillation column 130. The combined streams are contacted with ethylene glycol in extractive distillation column 130 to form extractive distillation column overhead stream 131 and bottoms stream 135. Overhead stream 131 is passed through a first condenser to form extractive distillation column condensate stream 132 and a gas stream. FIG. 11 depicts passing the gas stream through a second condenser to form an extractive distillation column second condensate stream 133. Condensate stream 132 may optionally refluxed to extractive distillation column 130 and/or be combined with second extractive distillation column condensate stream 133. Although not depicted in FIG. 11, one or more gas purge and/or liquid purge streams may be present in the extractive distillation column 130 overhead system to purge ethyl acetate and acetaldehyde from the process. In some aspects of the disclosure, not depicted in FIG. 10, the octanol reactor product stream 232 may be fractionated in extractive distillation column 130. Extractive distillation column second condensate stream 133 comprises ethanol and acetaldehyde, and is the ethanol feedstock for butanol reactor system 40. In some aspects of the present disclosure, extractive distillation column second condensate stream 133 is the source of ethanol for the octanol reactor system 230. Reactor product stream 45 generated in butanol reactor system 40 is passed through a condenser and fed forward to separation tank 46 to form gas stream 41 that passes through aldehyde reactor 170 to form stream 171 that is combined with condensed stream 42 (if present). Combined streams 171 and 42 (optionally) pass through one or more condensers and separation tank system 46 to form gas stream 48 comprising hydrogen, carbon dioxide, carbon monoxide and ethanol and condensate stream 47. Gas stream 48 is pressurized in recycle compressor 20 to form compressed splitter column second gas stream 21. In some aspects of the present disclosure, compressed splitter column second gas stream 21 may be the gas source for gas stream 33. In some other aspects of the present disclosure, compressed splitter column second gas stream 21 may be processed by pressure swing adsorption 30 to form gas stream 33 and purge stream 31 comprising hydrogen, carbon dioxide, carbon monoxide and methane. In some optional aspects of the present disclosure, at least a portion of recovered n-hexanol 282 (see FIG. 2) or recovered n-hexanol 282 (see FIG. 3) and/or fresh n-hexanol may be added to the reactor feed stream. In some further aspects of the present invention not depicted in FIG. 11, at least a portion of the hydrogen present in the reaction mixture is provided by a source of fresh hydrogen make-up. In some other aspects of the present disclosure, gas stream 33 is the source of hydrogen for the octanol reactor system as describe elsewhere herein. In some other aspects of the present disclosure, a combination of compressed splitter column second gas stream 21 and gas stream 33 are the gas source for butanol reactor system 40. Extractive distillation column second condensate stream 133 is combined with gas stream 33 comprising hydrogen and recovered n-hexanol stream 282 to form reactor feed stream 36. Reactor feed stream 36 is heated and pressurized to form reactor feed vapor stream 37 that is sent to butanol reactor system 40 containing one reactor, or two or more reactors. In butanol reactor system 40, ethanol is contacted with a Guerbet catalyst under elevated pressure and temperature conditions to form reactor product stream 45. Condensate stream 47 is fed to extractive distillation column 130 to form bottoms stream 135 comprising ethylene glycol and n-butanol that is fed to regeneration column 90 where organic materials are stripped into overhead steam 96 and ethylene glycol is recovered in bottoms stream 95. Bottoms stream 95 is recycled to extractive distillation column 130 and fresh ethylene glycol make-up 146 is added as required. Regeneration column overhead stream 96 is passed through a condenser to form regeneration column overhead condensate stream 97 comprising n-butanol, hexanol and water. At least a portion of condensate stream 97 may be refluxed to regeneration column 90 and at least a portion is fed to isobutanol column 110. In isobutanol column 110, overhead stream 116 is formed comprising an azeotrope of butanol and water that is collected in separation vessel 117 as butanol phase 119 and water phase 118. Butanol phase 119 is refluxed to isobutanol column 110 and water phase 118 is fed to water stripper column 150. Organic compounds are stripped from water phase 118 to form overhead stream 151 that is passed through a condenser to form overhead stream 152. At least a portion of overhead stream 152 is refluxed to water stripper column 150 and at least a portion is fed to extractive distillation column 130. Isobutanol column bottoms stream 115 is fed to hexanol column 100 where bottoms stream 105 comprising n-hexanol, n-octanol and n-decanol and intermediate cut stream 108 comprising essentially pure butanol are formed. Hexanol column bottoms stream 105 is fractionated in hexanol/octanol/decanol purification system 210 (such as depicted, for instance and without limitation, in FIGS. 2 and 3) to form recovered n-hexanol stream 282 (FIG. 2) or 282 (FIG. 3). As further described elsewhere herein (such as depicted, for instance, in FIGS. 2 and 3), recovered n-hexanol is combined with a source of ethanol and a source of hydrogen and contacted with a heterogeneous catalyst in octanol reactor system 230 under elevated temperature and pressure conditions to form n-octanol and n-decanol. An overhead stream 106 is formed comprising water and low boiling organic compounds that is passed through a condenser to form overhead stream 107. Overhead stream 107 may be fed to extractive distillation column 130 and/or to water stripper column 150 (not depicted in FIG. 11).

In some optional aspects of the present disclosure not depicted in the Figures, second overhead condensate stream 54 may be optional partially or totally refluxed to ethyl acetate column 60 (FIG. 4 to 6 or 9) or to splitter column 50 (FIGS. 7 and 8). In some such aspects, such as upon start-up, second overhead condensate stream 54 may be partially or totally refluxed to ethyl acetate column 60 or splitter column 50 until steady state conditions are achieved. In some other aspects, at least a portion of stream 54 may be refluxed to column 60 or column 50 in order to control the ethyl acetate, water and/or acetaldehyde content in reactor feed vapor stream 37. In some other optional aspects of the present disclosure not depicted in the Figures, second overhead condensate stream 54 may be optional partially or totally refluxed to octanol reactor system 230. Selection of a suitable ratio of reflux to feed forward is within the purview of those skilled in the art.

In some other optional aspects of the present disclosure not depicted in FIGS. 4 to 11, recycle compressor 20 may be located and positioned such that reactor feed stream 37 or 38, and not splitter column second gas stream 55 or gas stream 21 is compressed and pressurized.

The process of the present disclosure, such as depicted in FIGS. 1 to 11, may be practiced on a continuous basis. However, the present disclosure is not limited to continuous processes and can be practiced on batch or semi-batch, or discontinuous processes.

Many Guerbet catalysts are known in the art. Homogeneous and heterogeneous catalysts are within the scope of the present disclosure. Such catalysts include alkali metal alkoxides, such as sodium ethoxide (NaOEt) (M. Guerbet, Compt. Rend. 128, 511 (1899) 1002); copper bronze (C. Weizmann, et al., J. Org. Chem 15 (1950) 54); a mixture of potassium hydroxide and boric oxide (M. Sulzbacher, J. Appl. Chem 5 (1955) 637); a mixture of magnesium oxide, carbonate potassium and copper chromite (M. N. Dvornikoff. et al., J. Org. Chem 22 (1957) 540); CaO, MgO and $Na_2CO_3/CuO$ (M. N. Dvornikoff, et al., J. Org. Chem 22 (1957) 540); Ni-Raney, $MnCrO_2$, CuOx and $Zn/CrO_2$ (M. N. Dvornikoff, et al., J. Org. Chem 22 (1957) 540); an alkali metal alcoholate/boric acid ester (U.S. Pat. No. 2,861,110 (1958)); the addition of a nickel catalyst to metal alkoxide (J. Am Chem Soc 76 (1953) 52); and sodium alkoxide mixed with 5 wt. % Rh on alumina (P. L. Burk, et al., J. Mol. Catal. 33 (1985) 15). Some other Guerbet catalysts include cation exchanged zeolites, such as Metal-L (where Metal=K, Na, Ba, Cs, etc.) and Metal-X (where Metal=K, Na, Ba, Cs, among others) (U.S. Pat. No. 5,300,695; and C. Yang, Z. Meng, J. Catal. 142 (1993) 37). Still other Guerbet catalysts include Cu containing multiple basic oxides such as $Cu/ZnO/Al_2O_3$, Cu—$Co/ZnAl_2O_4$ and with K or Cs $Cu_xM$-$g_yCeO_x$ as promoters (J. G. Nunan, C. E. Bogdan, K. Klier, C. Young, R. G. Herman, J. Catal. 116 (1989) 195; U.S. Pat. No. 5,387,570; and M. J. L. Gines, E. Church, J. Catal. 176 (1998) 155). Yet other Guerbet catalysts include $Ru/Al_2O_3$, $Rh/Al_2O_3$, $Pd/Al_2O_3$, $Pt/Al_2O_3$, $Au/Al_2O_3$, $Ni/Al_2O_3$, and $Ag/Al_2O_3$. Still another group of Guerbet catalysts include transition metals (e.g., Mn, Cr, Zn, Al, etc.) supported on MgO (W. Ueda, T. Kuwabara, T. Oshida, Y. Morikawa, J. Chem Soc, Chem Commun. (1990) 1558, and Catal. Lett. 12 (1992) 971). Yet another group of Guerbet catalysts are based on calcium phosphate type hydroxyapatite (U.S. Pat. No. 6,323,383, U.S. 2007/0255079, and WO 2011/031928). Yet other Guerbet catalysts include a Group VIII metal with a phosphine ligand (US 2013/0116481).

Recently, hydrotalcite-based catalytic materials have been reported (WO 2009/026510 A1, U.S. 2010/0160693 and U.S. 2010/0160692). As is known in the art, hydrotalcite is of general formula $Mg_6Al_2(CO_3)(OH)_{16}.4(H_2O)$. Studies performed with these mixed oxides of Mg and Al showed that the catalytic activity of these materials depends on the nature, the density and strength of surface basic sites, and, in turn, on the composition molar Mg/Al (J. I. Di Cosimo, et al., J. Catal. 178 (1998) 499; and J. I. Di Cosimo, et al., J. Catal. 190 (2000) 261). The prior art also been established that mixed oxides derived from hydrotalcites based on Cu/Mg/Al show improved catalytic activity (C. Carlini, et al., J. Mol. Catal. A: Chem 232 (2005) 13) or copper type catalyst systems chromite+mixed oxides of Mg and Al (derived from hydrotalcite precursors). Further, hydrotalcite-type materials (WO 2009/026510) as well as materials derived from hydrotalcites modified by including metal carbonates (WO 2009/026523) and ethylene diamine tetra acetates (WO 2009/026483) have been developed. Improved hydrotalcite-derived mixed oxide catalysts further comprising Ga in combination with Pd and/or Pt have been discovered to produce high n-butanol yield because of a synergistic effect of Ga-Metal in the metal oxide. This improvement is even more pronounced in the case of catalysts containing Pd and Ga.

In some aspects of the present disclosure the catalyst is a metal oxide catalyst (denoted as "Catalyst A") that comprises: (i) at least one bivalent metal, M1, selected from Mg, Zn, Cu, Co, Mn, Fe, Ni and Ca, (ii) at least one trivalent metal, M2, selected from Al, La, Fe, Cr, Mn, Co, Ni and Ga, (iii) at least one noble metal selected from Pd, Pt, Ru, Rh and Re, and, optionally, (iv) V, with the proviso that the catalyst comprises V, Ga or a combination thereof. In some aspects, the catalyst comprises V and/or Ga in combination with Pd.

In some other Catalyst A aspects, the Guerbet catalyst is a metal oxide that comprises (i) at least one bivalent metal selected from the list comprising Mg, Zn, Cu, Co, Mn, Fe. Ni and Ca, (ii) trivalent Ga, and (iii) a noble metal selected from the list comprising Pd, Pt, Ru, Rh and Re, preferably Pd. In some aspects, the Guerbet catalyst further comprises an additional trivalent metal selected from the list comprising Al, La, Fe, Cr, Mn, Co and Ni.

In some Catalyst A aspects, the catalyst is obtained by total or partial decomposition of a hydrotalcite of the formula $[M1_{(1-x)}M2_x(OH)_2][A^{m-}_{(x/m)}.nH_2O]$ that is impregnated with a metal oxide comprising at least one noble metal selected from Pd, Pt, Ru, Rh and Re and, optionally, V, wherein the catalyst comprises V, Ga, or a combination thereof. In some other aspects, V and of at least one noble metal selected from Pd, Pt, Ru, Rh and Re are added to the hydrotalcite after total or partial decomposition thereof. In this aspect: M1 and M2 are as described above; A is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II); x is a value between 0 and 1 or between 0.1 and 0.8; m is an integer between 1 and 4; and n is greater than 0, between 0 and 100 or between 0 and 20.

In some Catalyst A aspects, the hydrotalcite as described above is obtained by the co-precipitation of M1 and M2 compounds.

Preferably, the co-precipitation is performed in the aqueous phase. The co-precipitation of the compounds may be preferably performed following the addition of a solution of at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II) to a solution of at least one M1 compound and at least one compound of M2. This anion may be introduced between the sheets of the resulting hydrotalcite. In order to obtain solutions of the anion, sodium and/or potassium salts thereof may be used. Preferably, the at least one anion is selected from carbonate, bicarbonate and hydroxide. The best results are obtained when the co-precipitation is performed at a pH higher than 7, preferably between 10 and 14. Moreover, in order to regulate the pH, sodium and/or potassium hydroxide are preferably used.

In some Catalyst A aspects, prior to the precipitation of said compounds, there is dissolution of at least one M1 compound and at least one compound of M2. Soluble M1 and M2 compounds is understood to mean any salt that, when in contact with a solvent, is dissociated, preferably a polar solvent, more preferably water. Examples of soluble M1 and M2 compounds may be nitrates, halides, sulfates, carboxylates and, in general, oxoacids that comprise M1 or M2; preferably, the soluble M1 and M2 compounds are nitrates.

In some Catalyst A aspects of the present disclosure, M1 comprises Mg or consists essentially of Mg. In some other aspects, M2 is Al, Ga, or a combination thereof. In yet other aspects, the catalyst comprises V. In some other aspects, M2 comprises Al, Ga or any of its combinations. In other aspects, M2 comprises Al. In yet other aspects, M2 comprises Al and Ga. In other aspects, M1 is Mg, M2 is Al and Ga and the catalyst comprises V. In yet other aspects, M is Mg, M2 is Al and the catalyst comprises V. In other aspects, M1 is Mg. M2 comprises Ga and the catalyst does not comprise V In still other Catalyst A aspects, A is at least one anion selected from the list comprising $CO_3^{2-}$, $HCO_3^-$, $O_2^-$, $OH^-$, $Cl^-$, $NO_3^{2-}$, $Cl^-$, $F^-$, $Br^-$, $I^-$, $ClO_4^-$, $CH_3COO^-$, $C_6H—COO^-$, and $SO_4^{2-}$; from the list comprising $CO_3^{2-}$, $HCO_3^-$, $O_2^-$ and $OH^-$; or from the list comprising $CO_3^{2-}$, $HCO_3^-$, $O_2^-$ and $OH^-$.

The Catalyst A gels resulting from the co-precipitation as described above are filtered, washed with water and adequately dried. The presence of a hydrotalcite-type structure may be corroborated by means of X-ray diffraction analysis (XRD), whilst the composition (quantity and type of constituent) of the hydrotalcite or the corresponding mixed oxide obtained by thermal decomposition of the aforementioned hydrotalcite may be determined by means of inductive coupled plasma mass spectrometry (ICP-MS) and chemical analysis, amongst others.

In another Catalyst A aspect of the present disclosure, thermal decomposition of hydrotalcite is performed by means of calcination under atmosphere of oxygen, nitrogen or any mixture thereof at a temperature ranging between 250° C. and 650° C., preferably between 350° C. and 550° C. The thermal decomposition of hydrotalcite is preferably performed for an interval of 0.5 to 48 hours, preferably between 1 and 24 hours. This process may be performed by heating the hydrotalcite in a gaseous atmosphere and may be performed in a static oven or a calcination reactor with a controlled gas flow, the latter being the preferred system. The gas may be an oxidising gas or a non-oxidising gas. Examples of oxidising gases may include air and oxygen. Examples of non-oxidising gases may be inert gases, such as nitrogen, argon, helium and reducing gases, such as, for example, carbon dioxide, hydrogen and ammonia. Preferably, the calcination is performed in the presence of oxygen, nitrogen or mixtures thereof, and, even more preferably, in the presence of oxygen and nitrogen.

In another Catalyst A aspect of the present disclosure, the V and/or the noble metal is added to the metal oxide by wet impregnation, incipient volume impregnation or deposition-precipitation, preferably the V and the noble metal are added to the metal oxide by wet impregnation, incipient volume impregnation or deposition-precipitation, more preferably by incipient volume impregnation. The incipient volume impregnation method, also called incipient wetness impregnation method, is based on the use of a minimum quantity of liquid for the impregnation, only that which is necessary to reach the maximum saturation of the corresponding solid.

In another Catalyst A aspect of the present disclosure, the noble metal comprises Pd, or the noble metal is Pd. It has been discovered that the best yields to n-octanol are obtained when the calcined hydrotalcites containing Ga and/or V are impregnated with Pd. It has been further discovered that, at a given concentration of palladium, the hydrotalcite-derived catalysts that comprise gallium and/or vanadium in their structure provide higher yields of n-octanol in a nitrogen atmosphere than their analogues without gallium/vanadium.

In another Catalyst A aspect of the process as described above, the concentration of the noble metal in the catalyst is between 0.001 wt. % and 10 wt. % or between 0.01 wt. % and 5 wt. % with respect to the total catalyst, and the concentration of V is between 0.001 wt. % and 10 wt. % or between 0.01 wt. % and 5 wt. % with respect to the total catalyst.

In another Catalyst A aspect of the present disclosure, a calcination step is done following the addition of the noble metal. Calcination is preferably done in a static oven or in a reactor with a controlled gas flow in the presence of an oxidizing gas (e.g., air and/or oxygen), an inert gas (e.g., nitrogen, argon and/or helium) or a reducing gas (e.g., carbon dioxide, hydrogen and/or ammonia), or combinations thereof, at a temperature between 250° C. and 650° C. or between 350° C. and 550° C., and for a time period between 0.5 and 48 hours, between 1 and 24 hours or between 1 and 6 hours. In some such aspects, the calcination is done in the presence of oxygen, nitrogen, or mixtures thereof, or in the presence of oxygen and nitrogen.

In some Catalyst A aspects of the present disclosure, a reduction step is done after calcination for reduction of the noble metal active sites wherein the catalyst is exposed to a $H_2$ atmosphere at a temperature between 200° C. and 500° C. or between 250° C. and 450° C. and for a time period of between 0.5 and 48 hours, between 1 and 24 hours or between 1 and 6 hours.

In some further aspects of the present disclosure, the catalyst can suitably be a partially or fully thermally decomposed hydrotalcite as described in U.S. Pat. No. 8,071,822 (denoted as "Catalyst B") having the empirical formula:

$$[M^{2+}_{1-x}M^{3+}_x(OH)_2][\{M'A'\}^{n'-}]_a A^{n-}_{(1-a)(n'/n)}]_{x/n} \cdot yH_2O$$

wherein $M^{2+}$ is divalent Mg, or a combination of divalent Mg and at least one divalent member selected from the group consisting of Zn, Ni, Pd, Pt, Co, Fe, and Cu; $M^{3+}$ is trivalent Al, or a combination of trivalent Al and at least one trivalent member selected from the group consisting of Fe and Cr; x is 0.66 to 0.1; M' is (i) one or more divalent members selected from the group consisting of Pd, Pt, Rh, Co, and Cu; or (ii) one or more trivalent members selected from the group consisting of Fe, Cr, Au, Ir, and Ru; or (iii) a mixture of one or more of said divalent members with one or more of said trivalent members; A' is the anion of ethylenediaminetetraacetic acid; n' is the absolute value of the sum of the oxidation state of M' (i.e., +2 if M' is one or more divalent members or +3 if M' is one or more trivalent members) and the oxidation state of the anion of ethylenediaminetetraacetic acid (−4) (for example, for M'A' wherein M' is $Pd^{2+}$ with an oxidation state of +2, n' is +2); provided that if M' is said mixture, then n' is calculated according to the following equation:

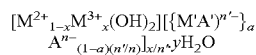

n'=the absolute value of $[X_D(2)+X_D(-4)+X_T(3)+X_T(-4)]$, wherein wherein $X_D$=the sum of the number of moles of all divalent members divided by (the sum of the number of moles of all divalent members+the sum of the number of moles of all trivalent members), and $X_T$=the sum of the number of moles of all trivalent members divided by (the sum of the number of moles of all divalent members+the sum of the number of moles of all trivalent members); $A^{n-}$ is $CO_3^{2-}$ with n=2 or $OH^-$ with n=1; a is 0.001 to 1; and y is 0 to 4.

In one Catalyst B aspect, $M^{2+}$ is divalent Mg; $M^{3+}$ is trivalent Al; M' is Co or Cu; a is 0.01 to 0.44; and $A^{n-}$ is $CO_3^{2-}$ or $OH^-$.

The catalysts described by the U.S. Pat. No. '822 patent are derived from a hydrotalcite of the formula as defined above by a process comprising heating the hydrotalcite for a time and at a temperature sufficient to cause a diminution in the hydrotalcite powder X-ray diffraction pattern peak intensities between 2θ angles of 10 degrees and 70 degrees using CuKα radiation.

In some other Catalyst B aspects of the present disclosure, the metal oxide is obtained from the total or partial thermal decomposition of a hydrotalcite, the catalyst having the formula $[M1_{1-(x+y)}M2_yM3_x(OH)_2][A^{m-}_{(x+y)/m} \cdot nH_2O]$. In connection with this aspect, hydrotalcite is understood to mean the structural family of laminar mixed hydroxides with the formula described above. M1 is at least one bivalent metal (i.e., having a $2^+$ charge) selected from the list comprising Mg, Zn, Cu, Co, Mn, Fe, Ni and Ca; M2 is trivalent Ga; M3 is as described above; A is at least one anion selected from the list comprising hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II); x is a value between 0 and 0.5; x is a value of from 0.1 to 0.5 or from 0.1 to 0.4; y is a value of from 0.00001 to 0.49, of from 0.00005 to 0.45 or from 0.0001 to 0.4; m is an integer of form 1 to 4; and n is greater than 0, such as from 0 to 100 or from 0 to 20; and "n" indicates the number of crystallization water molecules and is dependent on the composition of the hydrotalcite cations.

In some Catalyst B aspects of the present disclosure, the hydrotalcite is obtained by the co-precipitation of at least one M1 compound and at least one compound of a trivalent metal selected from the list that comprises M2 and M3. Is some other aspects, the hydrotalcite is obtained by the co-precipitation of M1, M2 and M3 compounds.

In any of the various aspects of the present disclosure, the butanol reactor system and the octanol reactor system may utilize the same catalyst, or a different catalyst. In aspects of the present invention wherein the butanol reactor system and/or octanol reactor system comprises more than one reactor, each reactor may utilize the same catalyst or a different catalyst.

As depicted in FIGS. 4 to 11, the reaction to butanol takes place in butanol reactor system 40 and the reaction to octanol takes place in octanol reactor system 230. Butanol reactor system 40 and octanol reactor system 230 may each comprise a single reactor or more than one reactor, such as 2, 3 or 4 reactors. Multi-reactor designs may be suitably configured in a sequential or in a parallel reactor arrangement, or a combination thereof. In some aspects of the present disclosure, the reaction to butanol (the butanol reactor system 40) may be carried out in at least two sequential gas phase reactors, or at least three sequential gas phase reactors. In some other aspects of the present disclosure, the reaction to butanol may be carried out in two or more parallel reactors. In yet other aspects, the reaction to butanol may be carried out in two or more parallel reactors and one or more reactors in sequential arrangement there-with. In some aspects of the present disclosure, the reaction to hexanol (the octanol reactor system 230) may be carried out in at least one gas phase reactor. In some other aspects of the disclosure, the reaction to hexanol may be carried out in at least two gas phase reactors arranged in parallel or in sequence.

The selection of suitable reactors is within the purview of those skilled in the art. Reactor designs suitable for the practice of the present disclosure include, for example and without limitation, discontinuous reactors, continuous stirred-tank reactors, fixed-bed continuous reactors, fluidized-bed continuous reactors, and batch reactors. Gas phase reactors having a fixed catalyst bed are generally preferred. Reactors may suitably be of plug flow or turbulent flow design. The reaction conditions may be adiabatic or isothermal, or temperature gradients between reactors in multi-reactor systems may be used. In some aspects of the present disclosure, the reactor system comprises one or more plug flow reactors in having a fixed catalyst bed. In some other aspects of the present disclosure the reactor system can comprise at least one plug flow reactor and at least one turbulent flow reactor. The Guerbet reaction is exothermic and in some aspects of the present disclosure the reactors may have intercooling to allow for temperature control. Oil may be used as the reactor cooling medium, and heat may be recovered from the heated reactor cooling oil in a heat exchanger and used elsewhere in the process. In some multi-reactor aspects of the present disclosure, the recovered heat may be used to heat the feed stream to the first reactor.

In some aspects of the present disclosure, the reaction conditions and concentrations of some of the various components in the butanol reactor system 40 and the octanol reactor system 230, and combinations of components, of the reaction mixture may be controlled in order to maximize alcohol conversion and selectivity to Guerbet alcohol reaction products n-butanol, n-octanol and n-decanol. Control may be done by methods known to those skilled in the art, such as by flow control.

In some aspects of the present disclosure, the reaction mixture 37 for the butanol reactor system 40 comprises ethanol, hydrogen and water and the mole ratio of hydrogen to ethanol may be controlled to from about 0.01:1 to about 10:1, from about 0.1:1 to about 5:1, from about 0.1:1 to about 3:1, from about 0.1:1 to about 1.5:1, from about 0.1:1 to about 0.8:1, from about 0.1:1 to about 0.6:1, from about 0.1:1 to about 0.4:1, from about 0.05:1 to about 3:1 or from about 0.75:1 to about 1.5:1, such as about 0.1:1, 0.2:1, 0.4:1, 0.6:1, 0.8:1, 1:1, 1.5:1, 2:1 or 3:1.

In some aspects of the present disclosure the reaction mixture 37 (feed stream) further comprises acetaldehyde and the mole ratio of acetaldehyde to starting alcohol may be controlled to from about 0.001:1 to about 0.1:1. In some other aspects of the present disclosure, the mole ratio of acetaldehyde to alcohol in the reactor feed stream is controlled to from about 0.001:1 to about 0.005:1 or from about 0.001:1 to about 0.003:1. In yet other aspects of the present disclosure, the mole ratio of acetaldehyde to alcohol in the reactor feed stream is controlled to from about 0.005:1 to about 0.05:1, from about 0.005:1 to about 0.01:1, from about 0.01:1 to about 0.05:1, from about 0.01:1 to about 0.04:1, or from about 0.02:1 to about 0.04:1, such as about 0.001:1, 0.002:1, 0.003:1, 0.004:1, 0.005:1, 0.01:1, 0.02:1, 0.03:1, 0.04:1 or 0.05:1.

In some aspects of the present disclosure, the mole ratio of water to starting alcohol in reaction mixture 37 for the butanol reactor system 40 may be controlled to less than about 0.005:1, less than about 0.05:1, less than about 0.025: 1, from about 0.001:1 to about 0.05:1, from about 0.005:1 to about 0.05:1, or from about 0.01:1 to about 0.03:1, such as about 0.001:1, about 0.005:1, about 0.01:1, about 0.02:1 or about 0.03:1.

In some aspects of the present disclosure, the reaction mixture 37 (feed stream) further comprises carbon monoxide and the mole ratio of carbon monoxide to starting alcohol may be controlled to less than about 0.02:1, less than about 0.01:1, less than about 0.005:1, or less than about 0.003:1, from about 0.0005:1 to about 0.005:1, from about 0.001:1 to about 0.005:1, or from about 0.002:1 to about 0.004:1, such as about 0.005:1, about 0.003:1, about 0.002:1, or about 0.001:1.

In other aspects of the present disclosure, the reaction mixture 37 (feed stream) further comprises ethyl acetate and the mole ratio of ethyl acetate to starting alcohol may be controlled to less than about 0.005:1, less than about 0.002: 1, or less than about 0.001:1, from about 0.0001:1 to about 0.003:1, from about 0.0005:1 to about 0.0015:1, or from about 0.0005:1 to about 0.001:1, such as about 0.0005:1, about 0.001:1, about 0.003:1 or about 0.005:1.

In some particular aspects of the present disclosure, the reaction mixture 37 for the butanol reactor system 40 comprises from about 70 mole % to about 90 mole %, from about 75 mole % to about 85 mole % or from about 78 mole % to about 82 mole % ethanol; from about 5 mole % to about 25 mole %, from about 10 mole % to about 20 mole % or from about 12 mole % to about 18 mole % hydrogen; and from about 0.5 mole % to about 5 mole %, from about 1 mole % to about 3 mole % or from about 2 mole % to about 2.5 mole % water.

In some aspects of the present disclosure, the reaction mixture for the octanol reactor system 230 comprises ethanol, n-hexanol, hydrogen and water and the mole ratio of hydrogen to starting alcohol (predominantly ethanol and n-hexanol) may be controlled to from about 0.01:1 to about 10:1, from about 0.1:1 to about 5:1, from about 0.1:1 to about 3:1, from about 0.1:1 to about 1.5:1, from about 0.1:1 to about 1:1, from about 0.1:1 to about 0.8:1, from about 0.1:1 to about 0.6:1, from about 0.1:1 to about 0.5:1 or from about 0.1:1 to about 0.4:1, such as about 0.1:1, 0.3:1, 0.5:1, 0.7:1, 1:1, 1.5:1, 2:1 or 3:1.

In some aspects of the present disclosure, the mole ratio of water to starting alcohol in the reaction mixture for the octanol reactor system 230 may be controlled to less than about 0.005:1, less than about 0.05:1, less than about 0.025: 1, from about 0.001:1 to about 0.05:1, from about 0.005:1 to about 0.05:1, or from about 0.01:1 to about 0.03:1, such as about 0.001:1, about 0.005:1, about 0.01:1, about 0.02:1 or about 0.03:1.

In some aspects of the present disclosure, the octanol reaction mixture for the octanol reactor system 230 further comprises carbon monoxide and the mole ratio of carbon monoxide to starting alcohol may be controlled to less than about 0.05:1, less than about 0.01:1, or less than about 0.005:1, from about 0.005:1 to about 0.05:1, from about 0.001:1 to about 0.01:1, or from about 0.005:1 to about 0.01:1.

In some aspects of the preset disclosure, the mole ratio of ethanol to n-hexanol in the reaction mixture for the octanol reactor system 230 may be controlled to provide a mole excess of ethanol, at a ratio of about 0.3:1, about 1.2:1, about 1.3:1, about 1.4:1, about 1.5:1, about 2:1, about 2.5:1, about 3:1, about 4:1 or about 5:1, and ranges thereof, such as from about 0.3:1 to about 3:1, from about 1.1:1 to about 5:1, from about 1.1:1 to about 2:1, or from about 1.1:1 to about 1.5:1.

In some optional aspects of the present disclosure, the octanol reaction mixture for the octanol reactor system 230 further comprises at least one aldehyde and the mole ratio of aldehyde to starting alcohol may be controlled to from about 0.001:1 to about 0.1:1. In some aspects of the disclosure, aldehyde is supplied to the octanol reactor system by second overhead condensate stream 54 comprising recovered acetaldehyde. Examples of aldehydes within the scope of the present disclosure include ethanal (acetaldehyde), ethylhexanal, propionaldehyde, butanal (butyraldehyde), hexanal (hexanaldehyde) or octanal. In some other aspects of the disclosure, the aldehyde is hexanal that is recovered from condensed isobutanol column 110 overhead stream 116 (comprising from about 30 to about 50 mole % hexanal) and/or from hexanol column 100 overhead stream 106 (comprising from about 5 to about 15 mole % hexanal). In some other aspects of the present disclosure, the mole ratio of aldehyde to alcohol in the reactor feed stream is controlled to from about 0.001:1 to about 0.005:1 or from about 0.001:1 to about 0.003:1. In yet other aspects of the present disclosure, the mole ratio of aldehyde to alcohol in the reactor feed stream is controlled to from about 0.005:1 to about 0.05:1, from about 0.01:1 to about 0.05:1, from about 0.01:1 to about 0.04:1, or from about 0.02:1 to about 0.04:1, such as about 0.001:1, 0.002:1, 0.003:1, 0.004:1, 0.005:1, 0.01:1, 0.02:1, 0.03:1, 0.04:1 or 0.05:1.

In some particular aspects of the present disclosure, the reaction mixture for the octanol reactor system 230 comprises from about 35 mole % to about 50 mole %, from about 40 mole % to about 45 mole % or from about 41 mole % to about 44 mole % ethanol; from about 25 mole % to about 40 mole %, from about 27 mole % to about 37 mole % or from about 29 mole % to about 35 mole % n-hexanol; from about 15 mole % to about 30 mole %, from about 17 mole % to about 27 mole % or from about 18 mole % to about 26 mole % hydrogen; and from about 0.5 mole % to about 3 mole %, from about 0.8 mole % to about 2 mole % or from about 1 mole % to about 1.5 mole % water.

The reaction mixture feed rate to each of the butanol reactor system 40 and octanol reactor system 232 is preferably controlled to provide a liquid hourly space velocity (LHSV) of from about 0.5 to about 5, from about 0.5 to about 2, from about 0.75 to about 1.5 or from about 0.9 to about 1.1, such as about 0.75, 0.9, 1, 1.1, 1.25, 1.5, 2 or 3.

Various combinations of the process variables described above may be selected to achieve high n-butanol, n-octanol and n-decanol yield and selectivity. For instance, the below Table A lists some possible combinations of butanol reactor system 40 variables (denoted by "X") that may be controlled to achieve the objects of the present disclosure, where "AL" refers to aldehyde, "CO" refers to carbon monoxide, "EA" refers to ethyl acetate, "Alc" refers to total alcohol content in the reactor feed stream and "EtOH:HexOH" refers to the mole ratio of ethanol to n-hexanol in the reactor feed stream.

TABLE A

| Combination | H$_2$:EtOH | AL:EtOH | H$_2$O:EtOH | CO:EtOH | EA:EtOH | LHSV |
|---|---|---|---|---|---|---|
| 1 | X | | | | | |
| 2 | | X | | | | |
| 3 | X | X | | | | |
| 4 | X | | | | X | |
| 5 | | X | | | X | |
| 6 | X | X | | | X | |
| 7 | X | | X | | | |
| 8 | | X | X | | | |
| 9 | X | X | X | | | |
| 10 | X | | | X | | |
| 11 | | X | | X | | |
| 12 | X | X | | X | | |
| 13 | X | | | | | X |
| 14 | | X | | | | X |
| 15 | X | X | | | | X |
| 16 | X | | X | X | | |
| 17 | | X | X | X | | |
| 18 | X | X | X | X | | |
| 19 | X | | X | | X | |
| 20 | | X | X | | X | |
| 21 | X | X | X | | X | |
| 22 | X | | X | X | X | |
| 23 | | X | X | X | X | |
| 24 | X | X | X | X | X | |
| 25 | X | | X | X | | X |
| 26 | | X | X | X | | X |
| 27 | X | X | X | X | | X |
| 28 | X | | X | | X | X |
| 29 | | X | X | | X | X |
| 30 | X | X | X | | X | X |
| 31 | X | | | X | X | X |
| 32 | | X | | X | X | X |
| 33 | X | X | | X | X | X |
| 34 | X | | X | X | X | X |
| 35 | | X | X | X | X | X |
| 36 | X | X | X | X | X | X |

Table B lists some possible combinations of octanol reactor system 230 variables (denoted by "X") that may be controlled to achieve the objects of the present disclosure, where "AL" refers to acetaldehyde, "CO" refers to carbon monoxide, "EA" refers to ethyl acetate, "Alc" refers to total alcohol content in the reactor feed stream and "EtOH:HexOH" refers to the mole ratio of ethanol to n-hexanol in the reactor feed stream.

TABLE B

| Comb | EtOH:HexOH | H$_2$:Alc | H$_2$O:Alc | CO:Alc | AL:Alc |
|------|------------|-----------|------------|--------|--------|
| 1 | X | | | | |
| 2 | X | X | | | |
| 3 | X | | | | X |
| 4 | X | X | | | X |
| 5 | X | X | X | | X |
| 6 | X | X | | X | X |
| 7 | X | X | X | X | X |
| 8 | | X | | | |
| 9 | | X | | | X |

In some aspects of the present disclosure, a butanol reactor system 40 design and/or an octanol reactor system design 230 utilizing multiple feed points along a length of the reactor may be used to maintain a predominantly constant aldehyde concentration in the reaction mixture in the reagent feed section of the reactor in order to optimize n-butanol, n-octanol and n-decanol yield.

n-butanol and n-octanol are produced from ethanol and hexanol, respectively, by a two-step Guerbet reaction wherein, in the first reaction, ethanol or hexanol is dehydrogenated to form the corresponding aldehyde and hydrogen. In the second reaction, ethanol and acetaldehyde or ethanol and hexanal are condensed and hydrogenated to form n-butanol or n-octanol. n-decanol is generated by a similar mechanism. The dehydrogenation reaction is slightly endothermic, the condensation/hydrogenation reaction is slightly exothermic, and the overall Guerbet reaction is slightly exothermic. It has been discovered that, as compared to aldehyde formation, aldehyde is rapidly condensed with ethanol to form butanol or octanol. In the case of acetaldehyde, based on a simulation as reflected in Table C below, it is believed that essentially all of the acetaldehyde present in a reaction mixture is condensed with ethanol in about the first third of the reactor length. The simulation was carried out using a kinetic model developed to represent the behavior of the catalyst under different operating conditions involving combining acetaldehyde with the ethanol and hydrogen reactor stream. The kinetic model was developed using very broad operating conditions of temperature, pressure, hydrogen to ethanol ratio and LHSV. Experimental results for the reaction of a feed stream comprising ethanol, hydrogen and acetaldehyde corresponded to, and validated, the results predicted by the kinetic model. Thus, it is believed that ethanol dehydration to acetaldehyde is the rate limiting step in the Guerbet condensation reaction. It is further believed that a similar kinetic model is applicable to the reaction of hexanal with ethanol to form n-octanol.

TABLE C

| Reactor length | 1$^{st}$ Simulation (acetaldehyde mole fraction) | 2$^{nd}$ Simulation (acetaldehyde mole fraction) |
|----------------|--------------------------------------------------|--------------------------------------------------|
| 0 cm | 0.018 | 0.037 |
| 1.1 cm | 0.006 | 0.015 |
| 2.2 cm | 0.004 | 0.006 |
| 3.3 cm | 0.003 | 0.004 |
| 4.4 cm | 0.003 | 0.003 |
| 5.5 cm | 0.003 | 0.003 |

Based on experimental evidence to date, it has been discovered that reaction of a feed stream comprising up to 0.05 moles of acetaldehyde per mole of ethanol increases n-butanol yield and selectivity. It is further believed that a feed stream comprising up to 0.05 moles of hexanal per mole of ethanol may increase n-octanol yield and selectivity.

Without being bound to any particular theory, it is believed that introducing an aldehyde with the reaction mixture overcomes the rate-limiting dehydrogenation step thereby allowing for the higher concentrations of aldehyde in the reaction mixture and favoring selectivity to n-butanol and n-octanol. It has further been discovered that reaction of a feed stream comprising in excess of about 0.05 moles of aldehyde per mole of ethanol (e.g., about 5 mole % acetaldehyde or hexanal) reduces selectivity to n-butanol and n-octanol and results in increased amounts of higher alcohols as compared to feed streams comprising less than about 0.05 moles of aldehyde to ethanol. It is believed, without being bound by any particular theory, that reduced selectivity results from at least two factors, and combinations thereof. First, at higher aldehyde concentrations, the rate of aldehyde and ethanol condensation may be insufficient to consume essentially all of the aldehyde, thereby resulting in an aldehyde concentration in the reaction mixture high enough to allow for higher rates of condensation with butanol or higher alcohols as per the following example reaction schemes:

Butanol+Acetaldehyde+H$_2$→Hexanol+H$_2$O

Hexanol+Acetaldehyde+H$_2$→Octanol+H$_2$O

Octanol+Acetaldehyde+H$_2$→Decanol+H$_2$O

Ethanol+Hexanal+H$_2$→Octanol+H$_2$O

Second, it has been discovered that aldehyde concentrations in the feed stream in excess of about 5 or about 10 mole % causes temperature spikes, wherein higher reaction temperatures increase byproduct formation.

In accordance with the present disclosure, it has been discovered that a butanol or octanol reactor feed stream comprising aldehyde may be fed at multiple points along the length of the reactor in order to maintain a generally constant aldehyde concentration in at least a portion of the reactor and thereby improve n-butanol and n-hexanol selectivity and yield. For instance, in addition to the inlet, the reactor feed stream may be supplied at one or more injection points along the length of a portion of the reactor, termed the reactor feed section. In some aspects of the disclosure, the reactor feed section comprises at least a first reaction mixture addition site and a last reaction mixture addition site located along a length of the reactor, the reactor section from the first reaction mixture addition site to the last reaction mixture addition site being the reactor feed section. In some other aspects, the reactor feed section comprises at least one intermediate reaction mixture addition site located between the first reaction mixture addition site and the last reaction mixture addition site. In yet other aspects, the first reaction mixture addition site is located at the reactor inlet. In any of the various aspects, two or more injection points can be placed at intervals in the first two-thirds, first half, or first one-third of the length of the reactor. In some aspects of the present disclosure, the feed rate of the aldehyde/ethanol stream to the reactor may be based on measured aldehyde concentration and/or reaction temperature. Determination and selection of the reactor feed stream injection point location and profile, associated reactor feed stream addition rate, and control strategies designed to achieve an aldehyde concentration in the reactor feed section is within the purview of one skilled in the art.

Aldehydes may be isolated from any of the various process streams. For instance, acetaldehyde may be isolated from splitter column overhead stream 51, from ethyl acetate column overhead purge stream 64, from splitter column second gas stream 55 or it may be present in splitter column second overhead stream 54. Condensed isobutanol column 110 overhead stream 116 comprises from about 30 to about 50 mole % hexanal and hexanol column 100 overhead stream 106 comprises from about 5 to about 15 mole % hexanal that may be isolated and recycled to the octanol reactor. Isolation techniques are known in the art and include distillation.

In any of the various reactor multiple feed point aspects of the present disclosure, the mole ratio of aldehyde to ethanol in the reactor feed section of butanol reactor system 40 or the mole ratio of aldehyde to the total of ethanol and n-hexanol in the reactor feed section of octanol reactor system 230 may be controlled to an average of about 0.005:1, 0.01:1, 0.015:1, 0.02:1, 0.025:1, 0.03:1, 0.035:1, 0.04:1, 0.045:1 or 0.05:1, and ranges thereof, such as from about 0.005:1 to about 0.05:1, from about 0.01:1 to about 0.05:1, from about 0.01:1 to about 0.04:1 or from about 0.02:1 to about 0.04:1. In some aspects of the present disclosure, a second reactor feed stream comprising a mole ratio of aldehyde to ethanol or ethanol and n-hexanol in excess of 0.05:1, such as between 0.05:1 and about 0.2:1 can be utilized at one or more injection points in combination with a first reactor feed stream comprising a mole fraction of aldehyde to ethanol of less than 0.05:1. In any of the various aspects of the disclosure, the mole ratio of aldehyde to ethanol or ethanol and n-hexanol in any region of the reactor feed section does not differ by more than 50%, 40%, 30%, 20% or 10% from the average mole ratio of aldehyde to ethanol or ethanol and n-hexanol in the reactor feed section. In general, the temperature profile in the reactor feed section is such that the temperature in any region of the reactor feed section does not differ by more than 15° C., 10° C. or 5° C. from the average temperature along the length of the reactor feed section.

In any of the various aspects of the present disclosure, in addition to the above described process variables and combinations thereof, the reaction pressure in the one or more reactors in each of the butanol reactor system 40 and octanol reactor system 230 is from about 10 bara to about 200 bara, from about 20 bara to about 200 bara, from about 20 bara to about 150 bara, from about 20 bara to about 100 bara, from about 20 bara to about 80 bara, or from about 25 bara to about 60 bara, such as about 25 bara, 30 bara, 35 bara, 40 bara, 45 bara, 50 bara, 55 bara, 60 bara, 65 bara, 70 bara or 75 bara, and ranges thereof. Further, the reaction temperature in the one or more reactors is from about 50° C. to 450° C., from about 100° C. to about 450° C., from about 150° C. to about 450° C., from about 150° C. to about 400° C., from about 150° C. to about 350° C., from about 175° C. to about 400° C., from about 175° C. to about 300° C., from about 200° C. to about 350° C., or from about 200° C. to about 300° C., such as about 200° C., 210° C., 220° C., 230° C. 240° C., 250° C. 260° C., 270° C., 280° C., 290° C., 300° C., 310° C., 320° C., 330° C., 340° C., 350° C., 360° C., 370° C., 380° C., 390° C. or 400° C., and ranges thereof. In some aspects of the present disclosure, the butanol reaction temperature is from about 150° C. to about 350° C., from about 175° C. to about 30° C. or from about 200° C. to about 300° C. and the octanol reaction temperature is from about 200° C. to about 400° C. or from about 250° C. to about 350° C. In aspects of the present disclosure wherein two or more reactors are used in series, temperature and pressure gradients from the first to last reactor can be used. For instance, the temperature for each reactor in series may be about 50° C., 10° C., 15° C., 20° C., 25° C., 30° C. or 35° C. greater than the temperature in the preceding reactor and the pressure may be about 5 bara, 10 bara, 15 bara or 20 bara greater than the pressure in the preceding reactor. In some aspects of the present disclosure, as the catalyst deactivates towards the end of a production run, the conversion may be maintained by increasing gradually inlet temperature. For instance, the inlet temperature may be increased by about 10° C., 20° C., 30° C., 40° C., 50° C., 60° C., 70° C., 80° C., 90° C. or about 100° C. from the beginning of a production run to the termination of the production run. In general, the reaction temperature may be controlled such that the reactor system outlet temperature increases by about the same amount. In some aspects of the present disclosure, the reactor system outlet temperature reaches about 250° C., 260° C., 270° C., 280° C. 290° C., 300° C., 320° C. or 340° C. at the end of the production run. In preferred aspects of the disclosure, the butanol and octanol reactor feed streams are each a gas or vapor and the reaction is a gas phase reaction.

In any of the various butanol reaction system aspects of the present disclosure, an ethanol conversion of about 10%, 15%, 20%, 25%, 30%, 35%, 40%, 45%, 50%, 55% or 60% is achieved, such as from about 15% to about 40%, from about 20% to about 40%, from about 25% to about 40% or from about 25% to about 35%. A n-butanol yield based on ethanol of about 10%, 15%, 20%, 25%, 30% or 35% is achieved, such as such as from about 10% to about 40%, from about 10% to about 35%, from about 10% to about 30%, from about 15% to about 30%, from about 20% to about 30%. Selectivity to n-butanol of about 60%, 65%, 70%, 75%, 80%, 85%, 90% or 95% is achieved, such as from about 65% to about 95%, from about 65% to about 90%, from about 65% to about 85%, from about 65% to about 80%, from about 65% to about 70%, from about 70% to about 90%, from about 75% to about 85%, or from about 80% to about 85%. In some aspects of the present disclosure, the n-butanol yield based on ethanol is from about 15% to about 25% and the selectivity to n-butanol is from about 70% to about 85%, the n-butanol yield based on ethanol is from about 10% to about 15% and the selectivity to n-butanol is from about 90% to about 95%, or the n-butanol yield based on ethanol is from about 30% to about 35% and the selectivity to n-butanol is from about 65% to about 70%.

In any of the various octanol reactor system aspects of the present disclosure, an ethanol conversion of at about 20%, about 30%, about 40%, about 50%, about 60%/a, about 70% or about 75%, such as from about 20% to about 80%, from about 20% to about 60%, or from about 20% to about 40% is achieved. A n-hexanol conversion about 10%, about 15%, about 20%, about 25% or about 30%, such as from about 10% to about 30%, from about 10% to about 25%, from about 15% to about 25% or from about 15% to about 20% is achieved. Selectivity to n-octanol is at least 20%, at least 30%, at least 40%, about 20%, about 25%, about 30%, about 35%, about 40%, about 45% or about 50%, such as from about 20% to about 55%, from about 20% to about 50%, from about 25% to about 45%, from about 30% to about 50%, from about 40% to about 50%, or from about 35% to about 45%. A n-butanol selectivity of at least 10%, at least 15%, at least 20% or at least 25%, about 10%, about 15%, about 20%, about 25%, about 30%, about 35% or about 40% is achieved, such as from about 10% to about 40%, from about 15% to about 40%, or from about 15% to about 25%.

As used herein, selectivity of the reactant compounds to the product compounds is expressed according to the following equation:

$$S_i(\%) = \frac{(F_{i,out} - F_{i,in})(n_{c,i}/M_i)}{\sum_k [(F_{k,in} - F_{k,out})(n_{c,k}/M_k)]} \times 100$$

where: Si (%)=selectivity of compound i; $F_{i,in}$=Flow rate of compound i (kg/hr) in the feed stream; $F_{i,out}$=Flow rate of compound i (kg/hr) in the product stream; $M_i$=Molecular weight of compound i (kg/kmol); $n_{c,i}$=Number of carbon atoms in a molecule of compound i; and the summation index k refers to all reactant compounds for which $F_{k,in}$ is greater than $F_{k,out}$.

The n-butanol reactor product stream typically comprises from about 7 to about 15 mole %, from about 8 to about 13 mole % or form about 9 to about 12 mole % n-butanol, such as about 7, 8, 9, 10, 11, 12, 13, 14 or 15 mole %; from about 35 to about 60 mole % or from about 40 to about 50 mole % ethanol, such as about 42, 44, 46, 48 or 50 mole %; from about 0.3 to about 1.5 or from about 0.5 to about 1.2 mole % acetaldehyde, such as about 0.5, 0.6, 0.7, 0.8, 0.9, 1.0, 1.1 or 1.2 mole %; from about 5 to about 20 mole % water, such as about 10, 15 or 20 mole %; from about 15 to about 30 mole % $H_2$, such as about 15, 20 or 25 mole %; from about 0.05 to about 0.2 mole % ethyl acetate, such as about 0.1 or 0.15 mole %; and from about 0.5 to about 6.5 mole % or from about 1 to about 6 mole % of alcohols other than ethanol and n-butanol, including from about 0.5 to about 2.5 mole % or from about 1 to about 2 mole % n-hexanol, from about 0.1 to about 0.5 mole % or from about 0.1 to about 0.3 mole % n-octanol, and from about 0.2 to about 0.6 mole % or from about 0.3 to about 0.5 mole % i-butanol.

The n-octanol reactor product stream typically comprises from about 2 to about 5 mole %, from 2 to about 4 mole % or form about 2 to about 3 mole % n-octanol, such as about 2, 3, 4 or 5 mole %; from about 0.1 to about 0.6 mole %, from about 0.15 to about 0.5 mole %, or from about 0.2 to about 0.5 mole % n-decanol, such as about 0.1, 0.2, 0.3, 0.4, 0.5 or 0.6 mole %; from about 1 to about 6 mole %, from about 1.5 to about 4 mole %, or from 2 to about 3 mole % n-butanol, such as about 1, 2, 3, 4, 5 or 6 mole %; from about 25 to about 40 mole % or from about 25 to about 35 mole % ethanol, such as about 25, 30, 35 or 40 mole %; from about 20 to about 35 mole % or from about 20 to about 30 mole % n-hexanol, such as about 20, 25, 30 or 35 mole %; and from about from about 20 to about 35 mole % or from about 20 to about 30 mole % hydrogen, such as about 20, 25, 30 or 35 mole %.

The n-octanol reactor product stream, at standard temperature and pressure (not containing volatile components such as hydrogen), typically comprises from about 0.01 to about 0.08 mole fraction n-octanol, from about 0.02 to about 0.07 mole fraction n-octanol, from about 0.025 to about 0.06 mole fraction n-octanol, from about 0.01 to about 0.05 mole fraction n-octanol, or from 0.03 to about 0.05 mole fraction n-octanol, such as about 0.01, 0.02, 0.03, 0.04, 0.05, 0.06 or 0.08 mole fraction; from about 0.001 to about 0.006 mole fraction n-decanol, from about 0.002 to about 0.006 mole fraction n-decanol, or from about 0.003 to about 0.005 mole fraction n-decanol, such as about 0.001, 0.002, 0.003, 0.004, 0.005 or 0.006 mole fraction; 0.01 to about 0.08 mole fraction n-butanol, from about 0.02 to about 0.07 mole fraction n-butanol, from about 0.025 to about 0.06 mole fraction n-butanol, from about 0.01 to about 0.05 mole fraction n-butanol, or from 0.03 to about 0.05 mole fraction n-butanol, such as about 0.01, 0.02, 0.03, 0.04, 0.05, 0.06 or 0.08 mole fraction; from about 0.25 to about 0.5 mole fraction ethanol, from about 0.3 to about 0.5 mole fraction ethanol or from about 0.35 to about 0.45 mole fraction ethanol, such as about 0.3, 0.35, 0.4, 0.45 or 0.5 mole fraction; and from about 0.25 to about 0.45 mole fraction n-hexanol or from about 0.3 to about 0.4 mole fraction n-hexanol, such as about 0.25, 0.3, 0.35, 0.4 or 0.45 mole fraction. The mole ratio of n-octanol to n-butanol is from about 0.5:1 to about 1.5:1, from about 0.8:1 to about 1.2:1, or from about 0.9:1 to about 1.1:1. The mole ratio of n-octanol to n-decanol is from about 5:1 to about 15:1 or from about 8:1 to about 12:1.

In some aspects of the present disclosure as depicted in FIGS. 1 to 9, a splitter fractionation (distillation) column or a preflash fractionation (distillation) column receives and fractionates a reactor product streams from the butanol reactor system 40 and the octanol reactor system 230 comprising n-butanol, n-octanol and n-decanol. In general, the splitter column fractionates the reactor product stream to form a column bottoms stream enriched in relatively high boiling compounds including, but not limited to, n-butanol, i-butanol, n-hexanol, n-octanol and n-decanol as compared to the reactor product stream and a splitter column overhead stream enriched in relatively low boiling condensable and gaseous non-condensable compounds including, but not limited to, ethanol, acetaldehyde, ethyl acetate, hydrogen, carbon dioxide, carbon monoxide, methane, ethane and propane as compared to the reactor product stream. In general, the preflash column fractionates the reactor product stream to form a preflash column bottoms stream enriched in high boiling compounds including, but not limited to, n-butanol, i-butanol, n-hexanol, n-octanol and n-decanol as compared to the reactor product stream, a preflash column mid-cut stream enriched in compounds including, but not limited to, ethanol, water, acetaldehyde and ethyl acetate as compared to the reactor product stream, and a preflash column overhead stream enriched in gaseous non-condensable compounds including, but not limited to, hydrogen, carbon dioxide, carbon monoxide, methane, ethane and propane as compared to the reactor product stream.

Any column design capable of fractionating the various input streams of the present disclosure, such as, for instance, the reactor product stream comprising n-butanol, wet ethanol streams, aqueous streams containing organic compounds, n-butanol/hexanol/octanol/decanol streams, to form the various fractionation streams described herein is suitable for the practice of the present disclosure, and the selection of suitable fractionating columns is within the purview of those skilled in the art. Generally, fractionation (distillation) columns within the scope of the present disclosure include, for example, filling plate, valve plate, perforated plate, bubble plate, packed, and wetted-wall (falling film) column. The columns may also comprise conventional components such as, for example, reflux drums, condensers, reboilers or any combination thereof. Columns of the present disclosure are equipped with one, two or more overhead condensers and one, two or more overhead accumulation tanks and/or separator having gas and liquid (condensate) outlets and reflux capability. In some aspects of the present disclosure, the distillation column has trays and/or packings internal in each of the stripping section and the enrichment section. The term "internal" used in the present disclosure means the part in the distillation column where gas and liquid are actually brought into contact with one another. Examples of trays include a bubble-cap tray, a sieve tray, a ripple tray, a ballast tray, a valve tray, a counterflow tray, an Unifrax tray, a Superfrac tray, a Maxfrac tray, a dual flow trays, a grid plate tray, a turbogrid plate tray, a Kittel tray, or the like. Examples of packings include random packings such as a Raschig ring, a Lessing ring, a Pall ring, a Berl saddle, an Intalox saddle, a Dixon packing, a McMahon packing or Heli-Pak, or structured packings such as Mellapak, Gempak, Technopack, Flexipac, a Sulzer packing, a Goodroll packing, Glitschgrid or the like. A multi-stage distillation column having both a tray portion and a portion packed with packings can also be used.

In some splitter column aspects of the present disclosure, the splitter column bottoms, containing the reactor product stream comprising n-butanol, n-hexanol, n-octanol and n-decanol is heated to a temperature of from about 200° C. to about 300° C., or from about 220° C. to about 260° C. by the splitter column reboiler. In some aspects of the present disclosure, hot oil is used as the reboiler heating medium. The temperature of the top gas fraction passing to the overhead condenser is from about 100° C. to about 180° C. or from about 120° C. to about 160° C. The column pressure is maintained to from about 10 bara to about 30 bara, or from about 15 bara to about 25 bara. In some aspects of the present disclosure, the overhead condenser cooling temperature is used for splitter column pressure control. The splitter column generates an overhead stream enriched in relatively low boiling condensable compounds and gaseous non-condensable compounds including, but not limited to, ethanol, acetaldehyde, ethyl acetate, hydrogen, carbon dioxide, carbon monoxide, methane, ethane and propane as compared to the reactor product stream. The overhead stream is characterized by an essential absence of high boiling compounds such as n-butanol, n-propanol, i-butanol, n-hexanol, n-octanol and n-decanol. In some aspects of the present disclosure, the overhead stream comprises from about 55 to about 85 mole % or from about 75 to about 80 mole % ethanol; from about 0.2 to about 2 mole % or from about 0.5 to about 1.5 mole % acetaldehyde; from about 0.05 to about 0.5 mole % or from about 0.1 to about 0.2 mole % ethyl acetate; from about 1 to about 15 mole %, from about 2 to about 8 mole % or from about 3 to about 8 mole % hydrogen; from about 0.02 to about 0.1 mole % or from about 0.05 to about 0.1 mole % carbon dioxide; and from about 0.1 to about 1 mole % or from about 0.3 to about 0.8 mole % carbon monoxide. The splitter column generates a bottoms stream enriched in the high boiling compounds as compared to the reactor product stream. In some aspects of the present disclosure, the bottoms stream comprises from about 50 to about 95 mole % or from about 85 to about 90 mole % n-butanol; from about 0.02 to about 0.5 mole % or from about 0.2 to about 0.5 mole % i-butanol; from about 4 to about 15 mole % or from about 6 to about 8 mole % n-hexanol; from about 0.2 to about 0.2 mole % n-octanol.

The splitter column overhead stream, generated from the reactor product stream comprising n-butanol, is passed through a condenser to form a first splitter overhead condensate stream and a second splitter column gas stream. In such aspects of the present disclosure, the first (condensate) stream typically comprises from about 65 to about 95 mole % or from about 80 to about 90 mole % ethanol; from about 5 to about 30 mole %, from about 5 to about 20 mole % or from about 10 to about 15 mole % water; from about 0.1 to about 1.5 mole % or from about 0.5 to about 1 mole % acetaldehyde; and from about 0.05 to about 0.5 mole % or from about 0.1 to about 0.3 mole % ethyl acetate. In some aspects of the present disclosure at least a portion of the first stream may be refluxed to the splitter column and at least a portion is fed forward to an ethyl acetate column for the generation of an ethyl acetate stream and a wet ethanol stream. The selection of a suitable ratio of reflux to feed forward is within the purview of one skilled in the art and varies with, among other factors, the composition of the reactor product stream and the desired compositional profile of the first stream. The splitter column overhead gas stream typically comprises, among other components, from about 30 to about 70 mole % or from about 40 to about 60 mole % hydrogen; from about 25 to about 45 mole % or from about 30 to about 40 mole % ethanol; from about 2 to about 10 mole % or from about 3 to about 8 mole % water; from about 0.5 to about 2 mole % or from about 0.8 to about 1.5 mole % acetaldehyde; trace amounts (less than about 0.15 mole %) ethyl acetate; from about 1 to about 8 mole % or from about 2 to about 6 mole % carbon monoxide; and less than about 1, 0.5 or 0.3 mole % of total alcohols other than ethanol.

In some preflash column aspects of the present disclosure, the column bottoms, comprising the reactor product stream comprising n-butanol, n-hexanol, n-octanol and n-decanol is heated to a temperature of from about 110° C. to about 250° C., from about 130° C. to about 220° C., or from about 160° C. to about 200° C. by the preflash column reboiler. In some aspects of the present disclosure, hot oil is used as the reboiler heating medium. The temperature of the top gas fraction passing to the overhead condenser is from about 90° C. to about 125° C., from about 95° C. to about 120° C., or from about 100° C. to about 110° C., such as about 105° C. The temperature of the mid-cut stream fed forward to the splitter column is about 130° C. to about 170° C., from about 135° C. to about 165° C., or from about 140° C. to about 160° C., such as about 150° C. The column pressure is maintained to from about 10 bara to about 30 bara, or from about 15 bara to about 25 bara. In some aspects of the present disclosure, the overhead condenser cooling temperature is used for splitter column pressure control. The preflash column overhead stream is passed through a condenser to form a first overhead stream and a second preflash column overhead gas stream. As compared to the preflash column gas stream, the condensate stream is enriched in ethanol and water. The condensate stream is generally refluxed to the preflash column. In some aspects of the present disclosure, the condensate stream is totally refluxed to the preflash column. In some aspects of the present disclosure at least a portion of the first stream may be refluxed to the splitter column and at least a portion is fed forward to a splitter column, ethyl acetate column, extractive distillation or molecular sieves for recovery of non-ethanolic components and/or the recovery of dry ethanol. The selection of a suitable condenser temperature and reflux to feed forward ratio is within the purview of one skilled in the art and varies with, among other factors, the composition of the reactor product stream, the desired compositional profile of the condensate and gas streams, and the desired preflash column operating pressure. The preflash column gas stream typically comprises, among other components, from about 30 to about 70 mole % or from about 40 to about 60 mole % hydrogen; from about 25 to about 45 mole % or from about 30 to about 40 mole % ethanol; from about 2 to about 10 mole % or from about 3 to about 8 mole % water; from about 0.5 to about 5 mole % or from about 1 to about 3 mole % acetaldehyde; from about 0.03 to about 0.15 mole % or from about 0.05 to about 0.1 mole % ethyl acetate; from about 1 to about 8 mole % or from about 2 to about 6 mole % carbon monoxide; and less than about 1, 0.5 or 0.3 mole % of total alcohols other than ethanol.

The preflash column mid-cut stream, enriched in compounds including, but not limited to, ethanol, water, acetaldehyde and ethyl acetate as compared to the reactor product stream comprising n-butanol, is fed forward to a splitter column fractionation section. The preflash column bottoms stream, enriched in high boiling compounds including, but not limited to, n-butanol, i-butanol, n-hexanol, n-octanol and n-decanol as compared to the reactor product stream, is also fed forward to a splitter column to a fractionation section located between the reboiler and the mid-cut stream inlet. In such aspects of the present disclosure, the splitter column reboiler heats the bottoms to a temperature of from about 220° C. to about 260° C. or from about 230° C. to about 250° C., such as about 240° C. The temperature of the top gas fraction passing to the overhead condenser is from about 110° C. to about 130° C. or from about 115° C. to about 125° C., such as about 115° C. The temperature of the mid-cut stream is about 150° C. to about 190° C. or from about 160° C. to about 180° C., such as about 170° C. The column pressure is maintained to from about 10 bara to about 30 bara, or from about 15 bara to about 25 bara. The splitter column overhead stream, generated from the preflash column feed, is passed through a condenser to form a first overhead condensate stream and a splitter column overhead gas stream. Compositionally, the overhead, first condensate stream and gas streams are similar to the corresponding streams formed from the reactor product stream as described above. The splitter column gas stream may be combined with the preflash column gas stream. The condensate stream may be refluxed to the splitter column, the preflash column, or a combination thereof.

In some aspects of the present disclosure, the splitter column gas stream or a combination of preflash column and splitter column gas streams may be passed through a second condenser to form a splitter or preflash column second overhead condensate stream and splitter or preflash column second overhead gas stream. Such second overhead condensate streams are characterized as typically comprising, among other components, from about 75 to about 95 mole % or from about 80 to about 90 mole % ethanol; from about 5 to about 20 mole % or from about 10 to about 15 mole % water; from about 1 to about 10 mole %, from about 2 to about 8 mole %, or from about 3 to about 5 mole % acetaldehyde; and from about 0.05 to about 0.5 mole % or from about 0.1 to about 0.3 mole % ethyl acetate. Such second gas streams are characterized as typically comprising, among other components, from about 80 to about 95 mole % or from about 80 to about 90 mole % hydrogen; from about 1 to about 10 mole % or from about 4 to about 8 mole % carbon monoxide; from about 1 to about 15 mole % or from about 2 to about 10 mole % total methane, ethane and propane; less than about 0.2 mole % or less than about 0.1 mole % acetaldehyde; and only trace amounts of ethyl acetate.

In some aspects of the present disclosure, depicted in FIGS. 2, 4 to 6 and 9, at least a portion of the splitter column overhead condensate stream is fed forward to an ethyl acetate column for the generation of an ethyl acetate stream and a wet ethanol stream. Any column design capable of fractionating a feed stream to form a bottoms stream enriched in water and ethanol as compared to the feed stream and an overhead stream enriched in acetaldehyde and ethyl acetate as compared to the feed stream is suitable for the practice of the present disclosure. The selection of ethyl acetate fractionating columns is within the purview of those skilled in the art, with suitable columns described above in connection with the splitter column.

In any of the various aspects of the present disclosure, the ethyl acetate column bottoms (comprising the feed stream) is heated to a temperature of from about 70° C. to about 100° C., or from about 75° C. to about 95° C., by one or more ethyl acetate column reboilers. In some aspects of the present disclosure, isobutanol column overhead is used as the heating medium in a first reboiler and splitter column overhead is used as the heating medium in a second reboiler. The temperature of the top gas fraction passing to the overhead condenser is from about 30° C. to about 50° C., or from about 35° C. to about 45° C. The column pressure is operated at atmospheric pressure, or under slight positive pressure such from about 1 bara to about 1.5 bara, or from about 1 bara to about 1.2 bara.

The ethyl acetate column generates an overhead stream enriched in acetaldehyde and ethyl acetate as compared to the ethyl acetate column feed stream. In some aspects of the present disclosure, the overhead stream comprises from about 25 to about 60 mole % or from about 30 to about 50 mole % acetaldehyde; from about 1 to about 40 mole % or from about 15 to about 30 mole % ethyl acetate; and from about 5 to about 35 mole % or from about 20 to about 25 mole % ethanol. The overhead stream is passed through a condenser to form a condensate stream generally corresponding compositionally to the overhead stream and a gas stream comprising from about 30 to about 60 mole % acetaldehyde; from about 1 to about 10 mole % ethyl acetate; and less than about 5 mole % ethanol. In any of the various aspects of the present disclosure, at least a portion of the overhead condensate stream and gas stream are purged from the process. In some other aspects of the present disclosure, the overhead condensate stream may be purified to form an ethyl acetate commodity product.

The ethyl acetate column generates a bottoms stream enriched in ethanol and water as compared to the reactor product stream comprising n-butanol. The bottoms stream typically comprises from about 65 to about 95 mole % or from about 80 to about 90 mole % ethanol; from about 10 to about 30 mole % water; and no more than a trace amount of acetaldehyde and ethyl acetate.

In some aspects of the present disclosure, depicted in FIGS. 2-5, 7 and 9, various wet ethanol streams, including the ethyl acetate column bottoms stream, the splitter column overhead stream generated from preflash column mid-cut and bottoms streams, fresh ethanol feed, and a regeneration column overhead stream, may be processed by molecular sieve to generate a dry ethanol feed stream for conversion to butanol. Molecular sieves which are capable of adsorbing the water and optionally other impurities from an admixture thereof with an alcohol are well known. In one aspect, the molecular sieve material is selected to remove water. In some other aspects, the molecular sieve material is selected to remove addition impurities such as acetic acid and/or ethyl acetate from the third distillate to form the anhydrous ethanol composition. The selection criteria may include, for instance, pore size and volume characteristics. Typically, such molecular sieves are crystalline, although the particular sieve employed is not critical. Such sieves should, however, be capable of adsorbing at least about 2 w/w, from about 2 to about 30% w/w, or from about 5 to about 25% w/w under the adsorption conditions. Suitable molecular sieves include a zeolitic molecular sieve having an average pore diameter of about 3 Angstroms. Typical examples of such molecular sieves are the A type zeolites, such as 3A, 4A and 5A. Other suitable molecular sieves include inorganic adsorbents such as lithium chloride, silica gel, activated alumina, and/or bio-based adsorbents such as corn grits. The molecular sieves may be configured in a molecular sieve bed and multiple molecular sieve beds may be employed sequentially or in a counter-current arrangement.

In any of the various molecular sieve aspects of the present disclosure, one or more wet ethanol feed streams described herein are purified by molecular sieve to generate a dry ethanol stream for conversion to n-butanol, n-hexanol, n-octanol and n-decanol, and a molecular sieve wet ethanol stream containing removed water that may be processed for ethanol recovery, such as by a regeneration column. Wet ethanol streams include ethyl acetate column bottoms stream, splitter column mid-cut stream, fresh ethanol feed stream, and regeneration column overhead stream. The dry ethanol stream is characterized as comprising from about 88 to about 99.9 mole %, from about 98 to about 99.9 mole % or from about 99 to about 99.8 mole % ethanol; less than about 5 mole %, from about 0.05 to about 5 mole %, from about 0.1 to about 1 mole % or from about 0.1 to about 0.3 mole % water; less than about 0.5 mole % or less than about 0.3 mole % alcohol other than ethanol; and only trace amounts (i.e., less than about 0.05 mole %) of acetaldehyde and ethyl acetate. The molecular sieve wet ethanol stream typically comprises from about 35 to about 50 mole % or about 40 to about 45 mole % ethanol; from about 50 to about 65 mole % or about 55 to about 60 mole % water; and trace amounts (less than about 0.05 mole % each) of other compounds.

The molecular sieve wet ethanol stream may be processed in a regeneration column to fractionate the feed stream into recovered alcohol overhead, isoamyl alcohol mid-cut and waste water bottom streams. Any column design as described above capable of fractionating the molecular sieve wet ethanol stream of the present disclosure is suitable for the practice of the present disclosure. The regeneration column bottoms (comprising the wet ethanol feed stream from the molecular sieves) is heated to a temperature of from about 110° C. to about 150° C., or from about 120° C. to about 140° C., by a regeneration column reboiler. In some aspects of the present disclosure, splitter column overhead is used as the heating medium. The temperature of the top gas fraction passing to the overhead condenser is from about 90° C. to about 110° C., or from about 95° C. to about 105° C. The column pressure is operated under a pressure of from about 1.5 bara to about 4 bara, or from about 2 bara to about 3 bara. In some aspects of the present disclosure, the column pressure is controlled by the overhead condenser. In some further aspects of the present disclosure, fresh ethanol is introduced into the regeneration column as reflux.

The regeneration column generates an overhead stream consisting essentially of from about 75 to about 85 mole % ethanol and about 15 to about 25 mole % water with only trace amounts of other components. The overhead stream is recycled to the molecular sieves or is processed by extractive distillation to remove water and generate a dry ethanol stream for conversion to n-butanol, n-hexanol, n-octanol and n-decanol. The regeneration column further generates a side-draw purge stream comprising from about 1 to about 20 mole % or from about 5 to about 15 mole % isoamyl alcohol (3-methyl-1-butanol), from about 80 to about 99 mole % water and minor amounts of n-butanol and ethanol. The regeneration column generates a bottoms stream consisting essentially of water that is discharged from the process in waste water treatment.

In any of the various aspects of the present disclosure, fresh ethanol feed may be processed by molecular sieve, by a combination of the regeneration column and molecular sieve, as described above, by extractive distillation as described herein, by a fusel column, or by the combination of a fusel column and molecular sieve to generate a make-up dry ethanol feed stream for conversion to n-butanol, n-hexanol, n-octanol and n-decanol. Various sources of fresh ethanol are within the scope of the present disclosure including bioethanol generated in fermentation processes, ethanol generated by hydration of ethylene, and ethanol generated in catalytic cracking operations. Ethanol produced from renewable bio-based feedstocks (such as from energy crop or cellulosic sources) may contain a variety of impurities such as fusel oil (amyl alcohol isomers such as 3-methyl-1-butanol and n-amyl alcohol)), tall oil containing esters and rosin acids (cyclic carboxylic acids) alkali metals, phosphorous, fatty acids, ions (organic and inorganic), and surfactants.

Fresh ethanol feed may optionally be passed through a purification bed prior to dehydration and/or the fusel column in order to remove and thereby reduce the concentration of various contaminants including ionic contaminants such as organic salts, inorganic salts, anions and cations. Any purification means capable of removing contaminants from fresh ethanol is within the scope of the present disclosure. In some aspects of the present disclosure, ion exchange resin may be used for fresh ethanol purification. The ion exchange resin can be suitably placed in a column or a packed bed. The resins are in a cation exchange or anion exchange form, or a combination of the two. In principle, cation-exchange resins remove cations such as sodium, potassium, nitrogen containing compounds, or metal ions (e.g., nickel, iron and chromium), and anion-exchange resins remove anions such as sulfate, chloride, acetate and phosphines. In some optional aspects of the present disclosure, prior to or after purification treatment, the fresh ethanol may be treated in a treatment zone with a bleaching earth (e.g., bentonite clay) and/or activated carbon. Fresh ethanol may further optionally be filtered prior to or after purification by methods known to those skilled in the art.

In some aspects of the present disclosure, such as for instance depicted in FIG. 2, fresh ethanol feed comprising fusel oil impurities, such as ethanol sourced from renewable bio-based feedstocks, may be fractionated in a fusel column to generate an overhead stream comprising purified ethanol for conversion to higher alcohols and a bottoms stream comprising fusel oil and water. Suitable fusel columns are as described above. The selection of fractionating conditions necessary for the separation of water and fusel oil (comprising a mixture of amyl alcohol isomers having a boiling point range of from about 113° C. to about 140° C.) from ethanol required to achieve the desired purity is within the purview of one skilled in the art.

In some optional aspects of the present disclosure, purified fresh ethanol may be added to the process directly in the reactor feed stream instead of being initially dehydrated and purified by a molecular sieve, by a regeneration column, by a fusel oil column, as described above, and/or by extractive distillation as described herein.

In any of the various aspects of the present disclosure, at least 50%, at least 60%, at least 70%, at least 80%, at least 90%, at least 95%, at least 96%, at least 97%, at least 98% or at least 99%, such as from about 50% to about 99%, or from about 90% to about 99% of the ethanol present in the butanol and hexanol reaction mixtures is recovered from the reactor product streams and recycled to the butanol reactor system and the octanol reactor system. In some aspects of the disclosure, the source of ethanol for the butanol reactor system and the octanol reactor system comprises at least 50 mole %, at least 60 mole %, at least 65 mole % or at least 70 mole % of the recovered ethanol.

In some aspects of the present disclosure, depicted in FIGS. 6, 8, 10 and 11, various wet ethanol streams, including the ethyl acetate column bottoms stream, the splitter column overhead stream generated from preflash column mid-cut and bottoms streams, fresh ethanol feed, and a regeneration column overhead stream, may be processed by extractive distillation to generate a dry ethanol feed stream for conversion to n-butanol, n-hexanol, n-octanol and n-decanol. As is known in the art, extractive distillation is a method of separating close boiling compounds or azeotropes by carrying out the distillation in a multiplate rectification column in the presence of an added extractive agent (solvent) or solvent mixture, wherein the liquid(s) have a boiling point higher than the compounds being separated. When the compounds to be separated normally form an azeotrope, the extractive distillation agent will cause the compounds to boil separately during extractive distillation and thus make possible a separation in a rectification column that cannot be done at all when no agent is present. The extractive agent should boil higher than any of the close boiling liquids being separated and not form minimum boiling azeotropes with them. For instance, the additional solvent preferably employed for the extractive distillation may have a boiling point at the pressure under which the fractionation takes place which is at least 10° C., at least 20° C. or at least 30° C. higher than the boiling point of the highest-boiling component of the mixture to be separated. In general, the extractive agent is introduced near the top of the column and flows downward until it reaches the reboiler. Its presence on each plate of the rectification column alters the relative volatility of the close boiling compounds in a direction to make the separation on each plate greater and thus require either fewer plates to effect the same separation or make possible a greater degree of separation with the same number of plates. Usually the extractive agent is introduced a few plates from the top of the column to insure that none of the extractive agent is carried over with the lowest boiling component. At the bottom of a continuous column, the less volatile components of the close boiling mixtures and the extractive agent are continuously removed from the column.

Examples of suitable extractive agents include glycerin, propylene glycol, N,N-dimethylformamide, dimethylsulfoxide, 1,3-butanediol, 1,4-butanediol, 1,5-pentanediol, hexylene glycol, diethylene glycol, triethylene glycol and tetraethylene glycol. Examples extractive agent mixtures include two, three or four extractive agents selected from phenol, m-p-cresol, o-sec butylphenol, o-tert butylphenol, catechol, hydroquinone, resorcinol, 1-naphthol, 2-naphthol, acetophenone, ethyl acetoacetate, glycerin, dibutylphthalate, dioctylphthalate, diisooctylphthalate, diisodecylphthalate, ethylene glycol phenyl ether, 1,5-pentanediol, diethylene glycol, triethylene glycol, tetraethylene glycol, hexylene glycol, diethylene glycol diethyl ether, butoxypropanol, dipropylene glycol methyl ether, propylene glycol and dipropylene glycol, dimethylsulfoxide, dimethylformamide, 1,3-butanediol, 1,4-butanediol, 1,6-hexanediol, polyethylene glycol 300, diisobutylphthalate, diisodecylphthalate, N,N-dimethylacetamide and 3-chloro-1,2-propanediol. In some aspects of the present disclosure, the extractive agent is glycerin or ethylene glycol.

Selection of extractive distillation bottoms (reboiler) temperature, gas temperature and column pressure depends on, among other factors, the extractive agent, column feed rate, and desired degree of purity. In the case of glycerin, the column bottoms (comprising the feed stream and extractive agent) are heated to a temperature of from about 150° C. to about 250° C., or from about 180° C. to about 200° C. by one or more reboilers, and the temperature of the top gas fraction passing to the overhead condenser is from about 90° C. to about 110° C., or from about 95° C. to about 105° C. The column pressure is operated at atmospheric pressure, under a slight positive pressure, or at a pressure of from about 1 bara to about 5 bara, or from about 2 bara to about 4 bara. The overhead stream is passed through a condenser to form a dry ethanol stream with a composition as previously described. At least a portion of the non-condensed gasses, including ethyl acetate and acetaldehyde, may be purged from the process. The dry ethanol condensate stream is a source of ethanol for conversion to n-butanol, n-hexanol, n-octanol and n-decanol. At least a portion of the condensed ethanol may be refluxed to the extractive distillation column.

The extractive distillation bottoms stream comprises extractive agent (solvent), water and various extracted impurities. The bottoms stream is purified in a regeneration column to generate a purified solvent bottoms stream that is recycled to the extractive distillation column. The regeneration column overhead stream is passed through a condenser, and the condensate (comprising ethanol, water and organic impurities) is fed forward to a water stripper column. At least a portion of the overhead condensate stream may be refluxed to the extractive distillation column. Extractive solvent losses may be made up with fresh extractive agent. In the case of glycerin extractive agent, the extractive distillation column bottoms (comprising contaminated glycerin) is heated to a temperature of from about 120° C. to about 220° C., or from about 150° C. to about 190° C., by one or more regeneration column reboilers, and the temperature of the top gas fraction passing to the overhead condenser is from about 50° C. to about 100° C., or from about 55° C. to about 80° C. The regeneration pressure is operated at a partial vacuum of from about 0.1 bara to about 0.5 bara.

In some other aspects of the present disclosure, depicted in FIGS. 10 and 11, one or more extractive distillation columns may be used to fractionate the reactor product stream comprising n-butanol to form an overhead stream comprising low boiling organics including ethanol, acetaldehyde, and ethyl acetate and a bottoms stream a bottoms stream comprising water and higher boiling organics including n-butanol, i-butanol, n-hexanol, n-octanol and n-decanol.

In some aspects of the present disclosure, two extractive distillation columns in series are used wherein the first column is operated at a higher pressure than the second column and wherein the bottoms stream from the first column is further purified in the second column. In such aspects, prior to extractive distillation, the reactor product stream comprising n-butanol and higher alcohols is passed through one or more condensers to generate gas and condensate streams. The gas stream typically predominantly comprises non-condensable gasses including from about 80 to about 95 mole % or from about 80 to about 90 mole % hydrogen, and from about 1 to about 10 mole % or from about 4 to about 8 mole % carbon monoxide. The gas stream also comprises other gasses such as from about 1 to about 15 mole % or from about 2 to about 10 mole % total methane, ethane and propane; acetaldehyde; and only trace amounts of ethyl acetate. The condensate stream is fed to the first extractive distillation column for the generation of the overhead and bottoms streams. In the case of glycerin extractive agent, in the first extractive distillation column, the bottoms (reactor product stream and glycerin) are heated to a temperature of from about 150° C. to about 250° C., or from about 180° C. to about 220° C., by one or more reboilers, and the temperature of the top gas fraction passing to the overhead condenser is from about 30° C. to about 80°

C., or from about 40° C. to about 60° C. The column is operated at a pressure of from about 3 bara to about 7 bara, or from about 4 bara to about 6 bara. The overhead stream is condensed in a condenser or two or more sequential condensers to form a dry ethanol condensate stream characterized as comprising from about 98 to about 99.9 mole % or from about 99 to about 99.8 mole % ethanol; from about 0.05 to about 0.5 mole % or from about 0.1 to about 0.3 mole % water; less than about 0.5 mole % or less than about 0.3 mole % alcohol other than ethanol; and only trace amounts (i.e., less than about 0.05 mole %) of acetaldehyde and ethyl acetate. One or more gas streams comprising ethyl acetate and/or acetaldehyde may be purged from the process in the first extractive distillation overhead system.

In such embodiments of the present disclosure, the first extractive distillation column bottoms stream comprising extractive agent, n-butanol, i-butanol, n-hexanol, n-octanol, n-decanol, water, and some reduced quantity of ethanol is subjected to a second extractive distillation. In some aspects of the present disclosure, the same extractive agent is used in the first and second extractive distillation columns. In the case of glycerin, in the second extractive distillation column, the bottoms (comprising contaminated extractive agent) are heated to a temperature of from about 120° C. to about 220° C., or from about 150° C. to about 190° C., by one or more reboilers, and the temperature of the top gas fraction passing to the overhead condenser is from about 30° C. to about 80° C., or from about 40° C. to about 60° C. The column is operated at a pressure of from about 1 bara to about 3 bara, or from about 1.5 bara to about 2.5 bara. The overhead stream is passed through a condenser and refluxed to the first extractive distillation column. The bottoms stream, predominantly comprising extractive agent, n-butanol, i-butanol, n-hexanol, n-octanol, n-decanol and water is processed in a regeneration column as described above to generate a bottoms stream comprising essentially pure extractive agent that is recycled to the first and second extractive distillation column. A regeneration column overhead stream, predominantly comprising n-butanol, i-butanol, n-hexanol, n-octanol, n-decanol and water, is condensed and fed forward to a butanol column. The regeneration column bottoms (comprising contaminated extractive agent) is heated to a temperature of from about 180° C. to about 250° C., or from about 200° C. to about 240° C., by one or more reboilers, and the temperature of the top gas fraction passing to the overhead condenser is from about 25° C. to about 40° C., or from about 30° C. to about 30° C. The column is operated under a partial vacuum at a pressure of from about 0.03 bara to about 0.1 bara, or from about 0.05 bara to about 0.08 bara. In such aspects of the present disclosure, fresh ethanol may be introduced into the process in the first or the second extractive distillation column.

In some aspects of the disclosure, the reactor product stream 45 may optionally be processed in a secondary reactor to convert residual aldehyde (acetaldehyde) to ethanol and thereby increase yield. Such an optional aldehyde reactor is depicted as reactor 170 on FIG. 11. Such an aldehyde reactor may optionally be included in any of the various aspects of the present disclosure, such as the processes depicted in FIGS. 4 to 10. Suitable aldehyde reactors and operation thereof are as described above in connection with butanol reactor system 40.

In some other aspects of the present disclosure, one extractive distillation column is used. In such aspects, prior to extractive distillation, the reactor product stream may be optionally passed through an aldehyde reactor to convert residual aldehyde (e.g. acetaldehyde) to alcohol (e.g., n-butanol) and form a stream having reduced aldehyde content as compared to the reactor product stream comprising n-butanol. In such aspects, prior to extractive distillation, the reactor product stream is passed through a first condenser to form gas and condensate streams wherein the gas stream is passed through the aldehyde reactor. In either aspect, the resulting gas and condensate streams are combined and passed through one condenser, or two or more sequential condensers, to generate a gas comprising recyclable hydrogen and a condensate stream for processing by extractive distillation. The gas stream composition is as described above. The condensate stream is fed to the extractive distillation column for the generation of the overhead and bottoms streams. In the case of glycerin extractive agent, the column is operated at a pressure of from about 10 bara to about 30 bara, or from about 15 bara to about 25 bara and corresponding temperatures. The overhead stream is condensed in a condenser or two or more sequential condensers to form a dry ethanol condensate stream. The dry ethanol condensate stream composition is as described above. One or more gas streams comprising ethyl acetate and/or acetaldehyde may be purged from the process in the extractive distillation overhead system.

The extractive distillation column bottoms stream comprising extractive agent, n-butanol, i-butanol, n-hexanol, n-octanol, n-decanol and water, and some reduced quantity of ethanol is processed in a regeneration column as described above to generate a bottoms stream comprising essentially pure extractive agent that is recycled to the first and second extractive distillation column. A regeneration column overhead stream, predominantly comprising butanol, i-butanol, n-hexanol, n-octanol, n-decanol and water, is condensed and fed forward to a butanol column. Selection of suitable extractive distillation pressure and temperature ranges is within the purview of those skilled in the art based on the extractive agent. In such aspects of the present disclosure, fresh ethanol may be introduced into the process in the extractive distillation column.

In any of the various aspects of the present disclosure, a source of dry ethanol is generated in the process for use in forming the reaction mixture, the dry ethanol comprising recovered ethanol and fresh ethanol and characterized as comprising less than about 0.005 moles of acetaldehyde per mole of alcohol, less than about 0.001 moles each of acetaldehyde and ethyl acetate to alcohol, less than about 0.01 total moles of alcohol other than ethanol to ethanol, and the absence of hydrogen and carbon monoxide.

In aspects of the present disclosure wherein a splitter column or preflash column second overhead condensate stream and a second gas stream are formed, such as depicted in FIGS. 2 and 4 to 9, the second overhead condensate stream is characterized as comprising from about 80 to about 90 mole % ethanol, from about 2 to about 8 mole % acetaldehyde, from about 0.05 to about 0.5 mole % ethyl acetate, and the absence of hydrogen and carbon monoxide, and the second gas stream is characterized as comprising from about 80 to about 95 mole % hydrogen, from about 1 to about 10 mole % carbon monoxide, less than about 0.2 mole % acetaldehyde, and no more than a trace amount of ethyl acetate, water and alcohols other than ethanol.

In aspects of the present disclosure wherein a splitter column or preflash column second overhead condensate stream and a second gas stream are formed, such as depicted in FIGS. 2 and 4 to 9, the acetaldehyde concentration in the reaction mixture may be optionally controlled by combining the dry ethanol stream with the splitter column or preflash column second overhead condensate stream. In such aspects of the present disclosure, isolation of acetaldehyde and reintroduction into the process enables a predetermined acetaldehyde concentration in the reaction mixture to be effectively achieved by mixing ratio control. Moreover, removal of acetaldehyde allows for (i) acetaldehyde recovery and recycle, (ii) acetaldehyde purging from the process and (iii) a second, hydrogen-containing, gas stream that can be further purified prior to recycle into the process. In some acetaldehyde concentration control aspects of the present disclosure, as described above, second overhead condensate stream 54 comprising recovered acetaldehyde may be optional partially or totally refluxed to ethyl acetate column 60 (FIG. 4 to 6 or 9) or to splitter column 50 (FIGS. 7 and 8). Acetaldehyde not refluxed may be fed forward to the Guerbet reaction in reactor feed streams 36 and 37. The ratio of reflux to feed forward may controlled to achieve a preselected acetaldehyde concentration in the butanol reactor system 40 feed streams 36 and 37.

In aspects of the present disclosure wherein a splitter column or preflash column second overhead condensate stream and a second gas stream are formed, such as depicted in FIGS. 2 and 4 to 9, the essential absence of (i.e., no more than a trace amount of) ethyl acetate, water and non-ethanolic alcohols in the reaction mixture may be achieved by the generation of dry ethanol and splitter column or preflash column second overhead condensate streams containing only trace amounts of those compounds.

In aspects of the present disclosure wherein a splitter column or preflash column second overhead condensate stream and a second gas stream are formed, such as depicted in FIGS. 2 and 4 to 9, the hydrogen and carbon monoxide concentration in the reaction mixture may be achieved by combining (i) the dry ethanol and (ii) the splitter column or preflash column second overhead condensate streams with at (iii) at least a portion of the splitter column or preflash column second overhead gas stream.

In some aspects of the present disclosure, the second overhead gas stream can be incorporated directly into the reaction mixture. Such process options are depicted in FIGS. 2, 4 and 6 to 11 (splitter column second gas stream 21) and FIG. 5 (splitter column second gas stream 55). In some other aspects of the present disclosure, the second overhead gas stream 21 can be purified (such as by pressure swing adsorption) to generate a stream consisting essentially of hydrogen that is then incorporated into the reaction mixture. Examples of such process options are depicted in FIGS. 2, 4 and 6 to 11. In some other aspects of the present disclosure, a mixture of purified and unpurified second gas stream can be incorporated into the reaction mixture. In some other aspects of the present disclosure depicted in FIGS. 1 to 3, and within the scope of any of the various aspects of the present disclosure, at least a portion of the hydrogen present in the reaction mixture is provided by a source of fresh hydrogen such as generated hydrogen. Such hydrogen generators are known to those skilled in the art. In yet other aspects of the present disclosure, the Guerbet reaction may be conducted in the presence of only recycled hydrogen without the utilization of make-up hydrogen supplied from a source of generated hydrogen.

In some aspects of the present disclosure, the second overhead gas stream is purified by pressure swing adsorption ("PSA"). Pressure swing adsorption (PSA) processes are known in the art and are used for purifying hydrogen gas. In PSA processes, hydrogen gas included with impurity gases is fed to an adsorption tower filled with an adsorbent. The hydrogen gas passes through the adsorbent at a high pressure, while impurity gases, for example, $N_2$, $CH_4$, CO and $CO_2$ are adsorbed by the adsorbent at high pressure and are purged from the process.

In any of the various stripping column and flash column aspects of the present disclosure, about 100%, from about 50% to about 100%, from about 50% to about 80% or from about 60 to about 75%, at least 50 mole %, at least 60 mole %, mole %, at least 65 mole %, at least 70 mole %, at least 80 mole % or at least 90 mole %, such as about 65% or about 70%, of the hydrogen present in the second gas stream is recovered and recycled to the reaction mixture. Hydrogen concentration in the reaction mixture is controlled based on the rate of hydrogen recovery and recycle rate. For instance, in some aspects of the present disclosure, in one example, 0.1 moles of hydrogen are recovered and recycled for each mole of ethanol in the Guerbet reaction mixture.

In either aspect of the present disclosure for processing the reactor product stream by extractive distillation, as depicted in FIGS. 10 and 11, condensed regeneration column overhead is fed to an isobutanol column for the fractionation and removal of water therefrom. The overhead stream comprises a water-butanol azeotrope. The stream is passed through a condenser and fed to a separation tank. The butanol phase is refluxed to the butanol column and the water phase is fed forward to a water stripper column. The butanol column bottoms stream, comprising dry n-butanol, is fed to a hexanol column. Selection of suitable isobutanol column pressure and temperature ranges is within the purview of those skilled in the art. The overhead stream, comprising water and minor amounts of n-butanol, is passed through a condenser. A portion of the condensate is recycled to the stripper column and a portion of the condensate is fed as reflux to the first or second extractive distillation column. Selection of suitable stripper column pressure and temperature ranges is within the purview of those skilled in the art.

In such extractive distillation aspects of the present disclosure, the bottoms (comprising n-butanol bottoms stream from the butanol column) is heated in the hexanol column to a temperature of from about 180° C. to about 200° C., or from about 170° C. to about 190° C., by one or more reboilers, and the temperature of the top gas fraction passing to the overhead condenser is from about 110° C. to about 150° C., or from about 120° C. to about 140° C. The column is operated at a pressure of from about 1.1 bara to about 3 bara, or from about 1.3 bara to about 2 bara. In an optional aspect of the present disclosure, the hexanol bottoms are heated to a temperature of from about 150° C. to about 190° C., or from about 160° C. to about 180° C., by one or more reboilers, and the temperature of the top gas fraction passing to the overhead condenser is from about 80° C. to about 105° C., or from about 85° C. to about 100° C. The hexanol column is operated under a partial vacuum of about pressure of from about 0.2 to about 0.6 bara, or from about 0.3 bara to about 0.5 bara.

In some aspects of the present disclosure, depicted in FIGS. 1 to 8, any of the various crude stripper bottom streams comprising n-butanol, n-hexanol, n-octanol and n-decanol may be processed in a hexanol column to generate an overhead stream predominantly comprising n-butanol and i-butanol and a bottoms stream comprising n-hexanol, n-octanol and n-decanol. Suitable hexanol columns are as described elsewhere herein in connection with distillation columns. In the hexanol column, the bottoms are heated to a temperature of from about 130° C. to about 190° C., or from about 160° C. to about 180° C., by one or more reboilers, and the temperature of the top gas fraction passing to the overhead condenser is from about 35° C. to about 130°

C., or from about 85° C. to about 100° C. In some aspects of the disclosure, the hexanol column is operated under a partial vacuum of about pressure of from about 0.1 to about 0.6 bara, or from about 0.3 bara to about 0.5 bara. In some other aspects of the disclosure, the hexanol column is operated at about atmospheric pressure. The hexanol column overhead stream comprising n-butanol and i-butanol is passed through a condenser and forwarded to an i-butanol column for the separation of n-butanol from i-butanol. In some aspects of the present disclosure, a gas stream comprising oxygen, nitrogen and water gas may be vented from the process. At least a portion of the condensate is refluxed to the hexanol column and the remainder is fed to the i-butanol column. The hexanol column bottoms stream typically comprises about 70 mole %, about 75 mole %, about 80 mole % or about 85 mole % n-hexanol, and ranges thereof, such as from about 70 to about 85 mole %, or from about 75 to about 85 mole %; about 5 mole %, about 7 mole %, about 9 mole %, about 11 mole %, about 13 mole % or about 15 mole % n-octanol, and ranges thereof, such as from about 5 to about 15 mole %, or from about 7 to about 11 mole %; about 3 mole %, about 4 mole %, about 5 mole %, about 6 mole %, or about 7 mole % 2-ethyl-1-butanol, and ranges thereof, such as from about 3 to about 7 mole %, or from about 4 to about 6 mole %; about 0.5 mole %, about 1 mole %, about 1.5 mole %, about 2 mole %, or about 2.5 mole % 2-ethyl-n-hexanol, and ranges thereof, such as from about 0.5 to about 2.5 mole %, or from about 1 to about 2 mole %; and about 0.3 mole %, about 0.5 mole %, about 1 mole %, about 1.5 mole %, or about 2 mole % n-decanol, and ranges thereof, such as from about 0.3 to about 2 mole %, or from about 0.5 to about 1.5 mole %.

The crude hexanol column overhead condensate predominantly comprising n-butanol and i-butanol is forwarded to the isobutanol column for fractionation. In some aspects of the disclosure, the column is operated under a vacuum of about 0.5 psia, about 1 psia, about 1.5 psia, or about 2 psia (about 0.03 to about 0.15 bara), and ranges thereof, such as from about 0.5 to about 2 psia, or from about 0.5 to about 1 psia. In such aspects, the i-butanol rich overhead stream is condensed at about 10° C. In other aspects of the disclosure, the column bottoms are heated to a temperature of from about 70° C. to about 140° C., or from about 110° C. to about 130° C., by one or more reboilers, and the temperature of the top gas fraction passing to the overhead condenser is from about 80° C. to about 110° C., or from about 95° C. to about 105° C. In such aspects, the isobutanol column is operated under a pressure of from about 1 to about 2 bara, or from about 1.1 bara to about 1.5 bara. The overhead stream is passed through a condenser and is optionally recycled to the ethyl acetate column, splitter column or extractive distillation column as reflux and/or is purged from the process. In any of the various aspects, the i-butanol column overhead stream predominantly comprises ethanol, n-propanol, i-butanol and 2-butanol, and only trace amounts of n-butanol. Butanol column bottoms stream consists of finished n-butanol comprising greater than 99 mole %, greater than 99.5 mole %, such as from 99 to 99.9 or from 99.5 to 99.9 mole % n-butanol with trace amounts of i-butanol, 3-methyl-1-butanol and 2-butanol.

In one process option depicted in FIG. 9, but applicable to any of the various aspects of the present disclosure, any of the various crude stripper bottoms n-butanol streams may be processed in an isobutanol column to generate a bottoms stream predominantly comprising n-butanol, n-hexanol, n-octanol and n-decanol, and an overhead stream predominantly comprising i-butanol. The isobutanol column bottoms stream is fed forward to a butanol column to generate a bottoms stream predominantly comprising n-hexanol, n-octanol and n-decanol and an overhead stream comprising substantially pure n-butanol product.

The hexanol column bottoms stream is forwarded to a hexanol purification column to fractionate and recover n-hexanol from the column overhead for use as a feedstock for the octanol reactor system and generate a bottoms stream comprising n-octanol, n-decanol, 2-ethyl-butanol and 2-ethyl-hexanol. In some aspects of the disclosure, the column is operated at generally at about 15 psia, about 16 psia, about atmospheric pressure, about 18 psia, about 19 psia, about 20 psia, about 21 psia, about 22 psia, or about 25 psia. The overhead stream typically comprises from about 90 mole %, about 91 mole %, about 92 mole %, about 93 mole %, about 94 mole %, about 95 mole %, or about 96 mole % n-hexanol; about 3 mole %, about 4 mole %, about 5 mole %, about 6 mole %, about 7 mole %, about 8 mole %, or about 9 mole % 2-ethyl-1-butanol; about 0.1 mole %, about 0.2 mole %, about 0.3 mole %, about 0.4 mole %, or about 0.5 mole % n-butanol; and trace amounts of other compounds. The bottoms stream typically comprises from about 50 mole %, about 55 mole %, about 60 mole %, about 65 mole %, or about 70 mole % n-octanol; about 5 mole %, about 10 mole %, or about 15 mole % 2-ethyl-n-hexanol; about 5 mole %, about 6 mole %, about 7 mole %, about 8 mole %, about 9 mole %, about 10 mole %, about 11 mole %, or about 12 mole % n-decanol; and about 2 mole %, about 3 mole %, about 4 mole %, about 5 mole %, about 6 mole %, about 7 mole %, or about 8 mole % 2-butyl-n-octanol. In any of the various aspects of the disclosure, at least 95 mole %, at least 96 mole %, at least 97 mole %, at least 98 mole %, at least 99 mole %, at least 99.5 mole % or at least 99.8 mole % of the n-hexanol contained in the hexanol column bottoms stream is recovered and recycled to the octanol reactor system. In some other aspects of the disclosure, at least 95 mole %, at least 96 mole %, at least 97 mole %, at least 98 mole %, at least 99 mole % of the n-hexanol contained in the hexanol reaction system reaction mixture is recovered and recycled to the octanol reactor system. In some aspects, the source of n-hexanol for the octanol reactor system comprises at least 60%, at least 65% or at least 70% recovered n-hexanol.

The overhead stream from the hexanol purification column is forwarded to a 2-ethyl-butanol column to fractionate 2-ethyl-butanol as an overhead stream and form purified n-hexanol as a bottoms stream and for use as n-hexanol feed to the octanol reactor system for condensation with ethanol. The bottoms stream typically comprises about 96 mole %, about 97 mole %, or about 98 mole % n-hexanol; about 2 mole %, about 3 mole % or about 4 mole % 2-ethyl-1-butanol; and trace amounts of other compounds. The overhead stream typically comprises about 90 mole % 2-ethyl-1-butanol, about 7 mole % n-butanol and about 2 mole % n-hexanol. In some aspects of the disclosure, The bottoms stream from the hexanol purification column may be fractionated to recover n-octanol and n-decanol in alternative process schemes.

In a first such process scheme generally depicted in FIG. 2, the hexanol purification column bottoms stream 225 is forwarded to octanol column 240 and fractionated to form bottoms stream 242 comprising n-decanol, 2-ethyl-n-octanol (i-decanol), and high boiling compounds and overhead stream 241 comprising n-octanol and 2-ethyl-hexanol. The overhead stream typically comprises about 80 mole % to about 90 mole % n-octanol and from about 10 mole % to about 20 mole % 2-ethyl-n-hexanol. The bottoms stream typically comprises from about 20 mole % to about 40 mole % n-decanol; from about 2 mole % to about 6 mole % 2-ethyl-n-octanol (i-decanol); from about 1 mole % to about 3 mole % 2-ethyl-n-decanol; from about 15 mole % to about 25 mole % 2-butyl-n-octanol; and from about 40 mole % to about 60 mole % of a mixture of high boiling compounds, such as i-decanol and hexa-decanol.

In the first scheme, the octanol column overhead stream is forwarded to n-octanol purification column 250 and fractionated to form overhead stream 251 predominantly comprising 2-ethyl-hexanol and bottoms stream 252 typically comprising at least 98 mole % or at least 99 mole % n-octanol. The n-octanol stream is forwarded to storage and the 2-ethyl-hexanol stream may optionally be sold as a commodity (optionally further purified) or incinerated for energy recovery.

In the first scheme, the octanol column bottoms stream is forwarded to i-decanol column 260 and fractionated to form overhead stream 261 predominantly comprising 2-ethyl-n-octanol (i-decanol) and bottoms stream 262 comprising n-decanol and high boiling compounds. The overhead stream typically comprises about 35 mole %, about 40 mole %, about 45 mole %, about 50 mole % or about 55 mole % 2-ethyl-n-octanol; about 10 mole %, about 15 mole %, or about 20 mole % hexoxyhexane; and about 1 mole %, about 2 mole %, about 3 mole % or about 4 mole % n-decanol. The bottoms stream typically comprises about 20 mole %, about 25 mole % or about 30 mole % n-decanol; about 10 mole %, about 15 mole %, or about 20 mole % 2-butyl-n-octanol; about 35 mole %, about 40 mole %, about 45 mole %, about 50 mole % or about 55 mole % high boiling compounds; and lesser amount of other components. The overhead stream may optionally be incinerated for energy recovery.

In the first scheme, the i-decanol column bottoms stream is forwarded to n-decanol column 270 to form overhead stream 271 predominantly comprising n-decanol and bottoms stream 272 predominantly comprising high boiling compounds. The overhead stream typically comprises at least 90 mole %, at least 95 mole %, at least 98 mole % or at least 99 mole % n-decanol. The n-decanol stream is forwarded to storage and the bottoms stream may optionally be incinerated for energy recovery.

In a second such process scheme generally depicted in FIG. 3, hexanol purification column bottoms stream 225 is fed forward to 2-ethyl-hexanol column 245 and fractionated to form overhead stream 247 predominantly comprising 2-ethyl-hexanol and bottoms stream 246 predominantly comprising n-octanol, n-decanol, 2-ethyl-n-octanol (i-decanol) and high boiling compounds. The 2-ethyl-hexanol column is typically operated under vacuum, such as about 1 psia, about 2 psia, about 3 psia or about 4 psia (about 0.07 to about 0.3 bara). The overhead stream typically comprises at least 95 mole %, at least 96 mole %, at least 97 mole % or at least 98 mole % 2-ethyl-hexanol. The 2-ethyl-hexanol stream may optionally be sold as a commodity (optionally further purified) or incinerated for energy recovery. The bottoms stream typically comprises about 55 mole %, about 60 mole %, about 65 mole %, about 70 mole %, or about 75 mole % n-octanol; about 10 mole %, about 15 mole %, or about 20 mole % heavy compounds; about 5 mole %, about 10 mole %, or about 15 mole % n-decanol; about 2 mole %, about 5 mole %, or about 8 mole % 2-butyl-n-octanol; about 1 mole %, about 2 mole % or about 3 mole % hexylhexanoate; and trace amounts of other compounds.

In the second scheme, bottoms stream 246 is fed forward to n-octanol column 290 and fractionated to form overhead stream 291 predominantly comprising n-octanol and bottoms stream 292 predominantly comprising n-decanol and high boiling compounds such as hexa-decanol. The n-octanol column is typically operated under slight pressure, such as about 15 psia, about 17 psia, about 19 psia, about 21 psia, or about 23 psia, or about 25 psia (about 1 to about 1.5 bara). The overhead stream typically comprises at least 98 mole % or at least 98 mole % n-octanol. The n-octanol stream is sent to storage. The bottoms stream typically comprises about 1 mole %, about 2 mole %, about 3 mole %, or about 4 mole % n-octanol; about 20 mole %, about 25 mole %, or about 30 mole % n-decanol; about 10 mole %, about 15 mole %, or about 20 mole % 2-butyl-n-octanol; about 2 mole %, about 5 mole %, or about 8 mole % hexylhexanoate; about 30 mole %, about 35 mole % or about 40 mole % high boiling compounds; and trace amounts of other compounds.

In the second scheme, not depicted in FIG. 2, bottoms stream 292 is forwarded to a decanol topping column and fractionated form an overhead stream predominantly comprising 2-ethyl-n-octanol (i-decanol) and a bottoms stream comprising n-decanol and high boiling compounds. The column typically operates under vacuum at a pressure of about 1 psia, about 2 psia, about 3 psia or about 4 psia, or about 5 psia (about 0.07 to about 0.35 bara). The overhead stream typically comprises about 35 mole %, about 40 mole %, about 45 mole %, about 50 mole % or about 55 mole % 2-ethyl-n-octanol; about 10 mole %, about 15 mole %, or about 20 mole % hexoxyhexane; and about 1 mole %, about 2 mole %, about 3 mole % or about 4 mole % n-decanol. The bottoms stream typically comprises about 20 mole %, about 25 mole % or about 30 mole % n-decanol; about 10 mole %, about 15 mole %, or about 20 mole % 2-butyl-n-octanol; about 35 mole %, about 40 mole %, about 45 mole %, about 50 mole % or about 55 mole % high boiling compounds; and lesser amount of other components. The overhead stream may optionally be incinerated for energy recovery.

The bottom stream from the decanol topping column is fed forward to n-decanol column 270 and fractionated to form overhead stream 271 predominantly comprising n-decanol and bottoms stream 272 predominantly comprising high boiling compounds (e.g., hexa-decanol). The column typically operates under slight pressure vacuum at a pressure of about 15 psia, about 16 psia, about 17 psia or about 18 psia, about 19 psia, about 20 psia, about 21 psia, about 22 psia, or about 23 psia (about 1 bara to about 0.07 to about 1.5 bara). The overhead stream typically comprises at least 98 mole % or at least 99 mole % n-decanol. The n-decanol stream is forwarded to storage and the bottoms stream may optionally be incinerated for energy recovery.

In some aspects of the disclosure, a facility for manufacturing n-butanol, n-octanol and n-decanol from a source of ethanol and a source of n-hexanol is provided.

Said facility comprises an octanol reactor system as described elsewhere herein. In some aspects, the octanol reactor system comprises at least one gas phase reactor having a fixed catalyst bed, the reactor comprising (i) an inlet for the input of a octanol reactor feed stream gas comprising a source of ethanol, a source of n-hexanol and a source of hydrogen, (ii) a reaction zone containing a heterogeneous catalyst for contact with the reactor feed stream to form an octanol reactor product stream, and (iii) an outlet for the discharge of the octanol reactor product stream, said octanol reactor product stream comprising ethanol, water, n-butanol, n-hexanol, n-octanol, n-decanol and hydrogen. The reactor system is operational at a reaction temperature of from about 150° C. to 450° C. and at a reaction pressure of from about 10 to about 200 bara. In some aspects, the flow of the octanol reactor feed streams is controlled to provide an octanol reactor LHSV of from about 0.5 to about 5, from about 0.5 to about 2, from about 0.75 to about 1.5 or from about 0.9 to about 1.1. Flow control methods are known to those skilled in the art and include, for instance, a flow control loop comprising a control valve, a flow measurement/transmitter instrument and a computerized flow controller that modulates the flow control valve in response to measured flow in order to maintain the flow around a setpoint. Flow may be suitably based on mass or volume.

Said facility further comprises a first system, as described elsewhere herein, for fractionating an octanol reactor product stream. In some aspects, the first system for fractionating the octanol reactor product stream comprises a distillation column or a flash column that forms (i) a first fractionated stream, said stream comprising at least 95 mole percent each of the water, the ethanol and the hydrogen contained in the octanol reactor product stream and (ii) a second fractionated stream, said stream comprising at least 95 mole percent each of the n-butanol, the n-hexanol, the n-octanol and the n-decanol contained in the octanol reactor product stream.

Said facility further comprises a second system, as described elsewhere herein, for fractionating said first fractionated stream. In some aspects, the second system for fractionating the first fractionated stream comprises a condenser and an ethanol dehydration system. In such aspects (i) the vapor is passed through the condenser to fractionate the recovered hydrogen stream as a gas and wet ethanol as a condensate and (ii) the wet ethanol is dehydrated to form the recovered ethanol stream and a water stream; the second fractionating system forms (i) a recovered ethanol stream comprising at least 95 mole percent of the ethanol and less than 5 mole percent of the water contained in the first fractionated stream and (ii) a recovered hydrogen stream; the second fractionating system recovered ethanol stream and recovered hydrogen stream are interconnected with the source of ethanol and the source of hydrogen for the octanol reactor system, and at least a portion of the recovered ethanol and the recovered hydrogen is recycled to the octanol reactor feed stream.

Said facility further comprises a third system, as described elsewhere herein, for fractionating said second fractionated stream. In some aspects, the third fractionating system comprises a distillation column that forms (i) a third fractionated stream, said stream comprising at least 95 mole percent of the n-butanol contained in the second fractionated stream and (ii) a fourth fractionated stream, said stream comprising at least 95 mole percent each of the n-hexanol, the n-octanol and the n-decanol contained in the second fractionated stream. In some further such aspects, the third fractionated stream enriched in n-butanol further comprises i-butanol and the facility further comprises a third fractionated stream distillation column. Said distillation column forms a n-butanol product stream having a purity in excess of 99 mole percent n-butanol and an impurity stream comprising i-butanol.

Said facility further comprises a fourth system, as described elsewhere herein, for fractionating the fourth fractionated stream. In some aspects, the fourth fractionating system comprises a distillation column that forms (i) a recovered n-hexanol stream, said stream comprising at least 95 mole percent of the n-hexanol contained in the fourth fractionated stream and (ii) a fifth fractionated, said stream comprising at least 95 mole percent of the n-octanol and n-decanol contained in the fourth fractionated stream. Said fourth fractionating system recovered n-hexanol stream is interconnected with the source of n-hexanol for the octanol reactor system and at least a portion of the recovered n-hexanol is recycled to the octanol reactor feed stream.

Said facility further comprises a fifth system, as described elsewhere herein, for fractionating the fifth fractionated stream. In some aspects, the fifth fractionating system comprises a distillation column that forms (i) a n-octanol product stream, said stream comprising at least 95 mole percent of the n-octanol contained in the fifth fractionated stream and (ii) a n-decanol product stream, said stream comprising at least 95 mole percent each of the n-decanol contained in the fifth fractionated stream. In some aspects, the facility further comprises an n-octanol product stream purification distillation column for fractionating the n-octanol product stream to form a n-octanol finished product stream having a purity in excess of 99 mole percent n-octanol. In some other aspects, the facility further comprises a n-decanol product stream distillation column for fractionating the n-decanol product stream form (i) a n-decanol finished product stream comprising at least 90 mole percent or at least 95 mole percent of the n-decanol contained in the crude n-decanol stream and (ii) a decanol column bottoms stream enriched in compounds that boil a temperature greater than the boiling point of n-decanol as compared to the n-decanol product stream.

Said facility for manufacturing n-butanol, n-octanol and n-decanol from a source of ethanol and a source of n-hexanol may further comprise (i) flow control for the source of ethanol to the octanol reactor system, (ii) flow control for the source of n-hexanol to the octanol reactor system, and/or (iii) flow control for the source of hydrogen to the octanol reactor system. In some aspects, the mole ratio of ethanol to n-hexanol in the octanol reactor feed stream may be controlled by flow ratio to from about 0.3:1 to about 3:1, from about 1.1:1 to about 2:1, from about 1.1:1 to about 1.5:1, or about 1.3:1. In some other aspects, the mole ratio of hydrogen to the sum of ethanol and n-hexanol in the octanol reactor feed stream may be controlled by flow ratio to from about 0.1:1 to about 5:1, from about 0.1:1 to about 1:1, from about 0.1:1 to about 0.5:1, or about 0.3:1.

Said facility for manufacturing n-butanol, n-octanol and n-decanol from a source of ethanol and a source of n-hexanol may further comprise a butanol reactor system as described elsewhere herein. In some aspects, the butanol reactor system comprises at least one gas phase reactor having a fixed catalyst bed, the reactor comprising (i) an inlet for the input of a butanol reactor system feed stream gas comprising a source of ethanol comprising recovered ethanol and a source of hydrogen comprising recovered hydrogen, (ii) a reaction zone containing a heterogeneous catalyst for contact with the catalyst to form a butanol reactor product stream, and (iii) an outlet for the discharge of a butanol reactor system product stream. In such aspects, the butanol reactor product stream may comprise ethanol, water, n-butanol, n-hexanol, and hydrogen. The butanol reactor system is operational at temperatures and pressures as described elsewhere herein, such as a reaction temperature of from about 150° C. to 450° C. and a reaction pressure of from about 10 to about 200 bara. In such butanol reactor system aspects, the butanol reactor product stream may be fractionated in the first system for fractionating the octanol reactor product stream, as described elsewhere herein, to separate at least 95 mole percent each of the water, the ethanol and the hydrogen contained in the butanol reactor product stream into the first fractionated stream and to separate at least 95 mole percent each of the n-butanol and the n-hexanol contained in the butanol reactor product stream into the second fractionated stream. In such butanol reactor system aspects, the second fractionating system recovered ethanol stream and recovered hydrogen stream may be further interconnected with the source of ethanol and the source of hydrogen for the butanol reactor system, and at least a portion of the recovered ethanol and the recovered hydrogen is recycled to the butanol reactor feed stream. In some further aspects, flow control for the source of ethanol to the butanol reactor system and flow control for the source of hydrogen to the butanol reactor system is provided and the mole ratio of hydrogen to ethanol may be controlled to from 0.1:1 to about 5:1, from about 0.1:1 to about 0.6:1, from about 0.1:1 to about 0.4:1, from about 0.5:1 to about 3:1, or from about 0.75:1 to about 1.5:1. In some aspects, the flow rate for the butanol reactor feed streams is controlled to provide a butanol reactor LHSV of from about 0.5 to about 5, from about 0.5 to about 2, from about 0.75 to about 1.5 or from about 0.9 to about 1.1.

In any of the various facility aspects for manufacturing n-butanol, n-octanol and n-decanol from a source of ethanol and a source of n-hexanol, at least 50 mole percent, at least 60 mole percent, at least 70 mole percent, at least 80 mole percent, at least 90 mole percent, at least 95 mole percent, or at least 99 mole percent of the n-hexanol present in the octanol reactor product stream and in the butanol reactor product stream is recovered and recycled to the octanol reactor feed stream. In some other such aspects, at least 50 mole percent, at least 60 mole percent, at least 70 mole percent, at least 80 mole percent, at least 90 mole percent or at least 95 mole percent of the ethanol present in the octanol reactor product stream and in the butanol reactor product stream is recovered and recycled to the octanol reactor feed stream, the butanol reactor feed stream, or a combination thereof. In some other such aspects, at least 50 mole percent, at least 60 mole percent, at least 70 mole percent, at least 80 mole percent, at least 90 mole percent or at least 95 mole percent of the hydrogen present in the octanol reactor product stream and in the butanol reactor product stream is recovered and recycled to the octanol reactor feed stream, the butanol reactor feed stream, or a combination thereof. In still other such aspects, the facilities are characterized by the absence of a product or waste stream comprising in excess of 0.001, 0.005 or 0.01 mole percent n-hexanol.

In some other aspects of the disclosure, a facility for manufacturing manufacturing n-butanol and n-octanol from a source of ethanol and a source of n-hexanol is provided.

Said facility comprises a n-butanol reactor system as described elsewhere herein. In some aspects, the n-butanol reactor system comprises at least one gas phase reactor having a fixed catalyst bed, the reactor comprising (1) an inlet for the input of a n-butanol reactor system feed stream gas comprising a source of ethanol and a source of hydrogen, (2) a reaction zone containing a heterogeneous catalyst for contact with the catalyst to form a n-butanol reactor product stream, and (3) an outlet for the discharge of a n-butanol reactor system product stream, the n-butanol reactor product stream comprising ethanol, water, n-hexanol, and hydrogen. The n-butanol reactor system is operational at a reaction temperature of from about 150° C. to 450° C. and at a reaction pressure of from about 10 to about 200 bara. In some aspects, the n-butanol reactor system comprises flow control for the source of ethanol and flow control for the source of hydrogen and the mole ratio of hydrogen to ethanol is controlled by flow control to from 0.1:1 to about 5:1, from about 0.1:1 to about 0.6:1, from about 0.1:1 to about 0.4:1, from about 0.5:1 to about 3:1, or from about 0.75:1 to about 1.5:1. In some other aspects, the n-butanol reactor system comprises flow control for the reactor feed streams and the flow rate of the feed streams is controlled to provide a n-butanol reactor LHSV of from about 0.5 to about 5, from about 0.5 to about 2, from about 0.75 to about 1.5 or from about 0.9 to about 1.1.

Said facility further comprises a n-octanol reactor system as described elsewhere herein. In some aspects, the n-octanol reactor system comprises at least one gas phase reactor having a fixed catalyst bed, the reactor comprising (1) an inlet for the input of a n-octanol reactor feed stream gas comprising a source of ethanol, a source of n-hexanol and a source of hydrogen, (2) a reaction zone containing a heterogeneous catalyst for contact with the reactor feed stream to form a n-octanol reactor product stream, and (3) an outlet for the discharge of the n-octanol reactor product stream, the n-octanol reactor product stream comprising ethanol, water, n-hexanol, n-octanol and hydrogen. The n-octanol reactor system is operational at a reaction temperature of from about 150° C. to 450° C. and at a reaction pressure of from about 10 to about 200 bara. In some aspects, the n-octanol reactor system comprises flow control for the source of ethanol and flow control for the source of n-hexanol. In some such aspects, the mole ratio of ethanol to n-hexanol in the n-octanol reactor feed stream is controlled by flow ratio to from about 0.3:1 to about 3:1, from about 1.1:1 to about 2:1, from about 1.1:1 to about 1.5:1, or about 1.3:1. In some other aspects, the n-octanol reactor system comprises flow control for the source of hydrogen and the mole ratio of hydrogen to the sum of ethanol and n-hexanol in the n-octanol reactor feed stream is controlled by flow ratio to from about 0.1:1 to about 5:1, from about 0.1:1 to about 1:1, from about 0.1:1 to about 0.5:1, or about 0.3:1. In some other aspects, the n-octanol reactor system comprises flow control for the reactor feed streams and the flow rate of the feed streams is controlled to provide a n-octanol reactor LHSV of from about 0.5 to about 5, from about 0.5 to about 2, from about 0.75 to about 1.5 or from about 0.9 to about 1.1.

Said facility further comprises a first system, as described elsewhere herein, for fractionating the n-butanol reactor product stream and the n-octanol reactor product stream. Said first fractionating system comprises a distillation column or a flash column that forms (1) a first fractionated stream comprising at least 95 mole percent each of the water, the ethanol and the hydrogen contained in the n-butanol reactor product stream and the n-octanol reactor product stream and (2) a second fractionated stream comprising at least 95 mole percent each of the n-butanol, the n-hexanol and the n-octanol contained in the n-butanol reactor stream and the n-octanol reactor product stream.

Said facility further comprises a second system, as described elsewhere herein, for fractionating the second fractionated stream. Said second fractionating system comprises a distillation column that forms (1) a n-butanol enriched stream comprising at least 95 mole percent of the n-butanol contained in the second fractionated stream and (2) a fourth fractionated stream comprising at least 95 mole percent each of the n-hexanol and the n-octanol contained in the second fractionated stream. In some aspects, the n-butanol enriched stream further comprises i-butanol, and the facility further comprises a distillation column for fractionating the n-butanol enriched stream to form a n-butanol product stream having a purity in excess of 99 mole percent n-butanol and an impurity stream comprising i-butanol Said facility further comprises a third system, as described elsewhere herein, for fractionating the fourth fractionated stream. Said third fractionating system comprises a distillation column that forms (1) a recovered n-hexanol stream comprising at least 95 mole percent of the n-hexanol contained in the fourth fractionated stream. Said recovered n-hexanol stream is interconnected with the source of n-hexanol for the n-octanol reactor system and at least a portion of the recovered n-hexanol is recycled to the n-octanol reactor feed stream and (2) a n-octanol stream comprising at least 95 mole percent of the n-octanol contained in the fourth fractionated stream. In some other aspects, the n-octanol stream is a crude n-octanol stream further comprising n-decanol and the facility further comprises a distillation column for fractionating the crude n-octanol stream to form (1) a n-octanol product stream comprising at least 95 mole percent of the n-octanol contained in crude n-octanol stream and (ii) a n-decanol enriched stream comprising at least 95 mole percent of the n-decanol contained in the crude n-octanol stream. In some aspects, the facility further comprises a n-octanol product stream purification distillation column. Said distillation column fractionates the n-octanol product stream to form a n-octanol finished product stream having a purity in excess of 99 mole percent n-octanol. In some aspects, the facility further comprises a n-decanol stream distillation column to fractionate the n-decanol enriched stream form (i) a n-decanol product stream comprising at least 90 mole percent or at least 95 mole percent of the n-decanol contained in the crude n-decanol enriched stream and (ii) a n-decanol stream distillation column bottoms stream enriched in compounds that boil a temperature greater than the boiling point of n-decanol as compared to the n-decanol enriched stream In some aspects, said facility further comprises a system, as described elsewhere herein, for fractionating the first fractionated stream. Said first fractionated stream comprises vapor and the system for fractionating the first fractionated stream comprises a condenser and an ethanol dehydration system. The first fractionated stream may be passed through the condenser to form a recovered hydrogen gas stream and a wet ethanol condensate stream and (b) the wet ethanol condensate stream may be dehydrated to form a recovered ethanol stream and a water stream. Said recovered ethanol stream comprises at least 95 mole percent of the ethanol and less than 5 mole percent of the water contained in the first fractionated stream. The recovered ethanol stream and recovered hydrogen stream may be interconnected with the source of ethanol and the source of hydrogen for the n-butanol reactor system and the n-octanol reactor system. At least a portion of the recovered ethanol and the recovered hydrogen may be recycled to the each of the n-butanol reactor feed stream and the n-octanol reactor feed stream.

In some aspects of the disclosure, at least 50 mole percent, at least 60 mole percent, at least 70 mole percent, at least 80 mole percent, at least 90 mole percent, at least 95 mole percent, or at least 99 mole percent of the n-hexanol present in the n-octanol reactor product stream and in the n-butanol reactor product stream is recovered and recycled to the n-octanol reactor feed stream. In some other aspects, at least 50 mole percent, at least 60 mole percent, at least 70 mole percent, at least 80 mole percent, at least 90 mole percent or at least 95 mole percent of the ethanol present in the n-octanol reactor product stream and in the n-butanol reactor product stream is recovered and recycled to the n-octanol reactor feed stream and to the n-butanol reactor feed stream. In some other aspects, at least 50 mole percent, at least 60 mole percent, at least 70 mole percent, at least 80 mole percent, at least 90 mole percent or at least 95 mole percent of the hydrogen present in the n-octanol reactor product stream and in the n-butanol reactor product stream is recovered and recycled to the n-octanol reactor feed stream and to the n-butanol reactor feed stream.

In some aspects, the facility for manufacturing manufacturing n-butanol and n-octanol from a source of ethanol and a source of n-hexanol is characterized by the absence of a process output stream comprising in excess of 0.001, 0.005 or 0.01 mole percent n-hexanol.

This written description uses examples, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

Example 1

Various catalysts were prepared as follows.

T-1 catalyst was prepared by means of a standard co-precipitation process using two solutions. The first solution contained 17.79 g of $Mg(NO_3)_2 \cdot 6H_2O$ and 26.05 g of $Al(NO_3)_3 \cdot 9H_2O$, dissolved in 48.72 g of Milli-Q water, with a molar concentration of Al+Mg of 1.5. The second solution contained 13.95 g of NaOH and 9.86 g of $Na_2CO_3$ in 68.85 g of Milli-Q water, and was used to produce the adequate precipitation of the Al and Mg species, and to set the pH of the total mixture at about 13. Both solutions were added, at a total flow velocity of 20 ml/h for about 4 hours to a container under vigorous stirring at room temperature. A gel formed that was aged at room temperature for 1 to 2 hours after which time it was filtered and washed with distilled water until the carbonate was not detected in the filtered liquid (at pH about 7). Subsequently, the solid was dried in an oven at 60° C. for 18 h. The hydrotalcite obtained was calcined in air at 450° C. and a mixed oxide, designated HT-1, was obtained having a Mg:Al molar ratio about 1,54 and a surface area (BET method) of 310.37 m2/g. The BET method refers to the Brunauer-Emmett-Teller isotherm method.

HT-3 catalyst was prepared by means of a standard co-precipitation process using two solutions. The first solution contained 27.99 g of $Mg(NO_3)_2 \cdot 6H_2O$ and 13.65 g of $Al(NO_3)_3 \cdot 9H_2O$, dissolved in 55.31 g of Milli-Q water, with a molar concentration of Al+Mg of 1.5. The second solution contained 13.13 g of NaOH and 10.23 g of $Na_2CO_3$ in 73.61 g of Milli-Q water, and was used to produce the adequate precipitation of the Al and Mg species, and to set the pH of the total mixture at about 13. Both solutions were added at a total flow velocity of 20 ml/h for about 4 hours to a container under vigorous stirring at room temperature. A gel formed that was aged at room temperature for 12 hours after which time it was filtered and washed with distilled water until the carbonate was not detected in the filtered liquid (at pH about 7). Subsequently, the solid was dried in an oven at 60° C. for 18 hours. The hydrotalcite obtained was calcined in air at 450° C. and a mixed oxide, designated HT-3, was obtained having a Mg:Al molar ratio about 3.10 and a surface area (BET method) of 254.03 $m^2/g$.

HT-4 catalyst was prepared by means of a standard co-precipitation process using two solutions. The first solution contained 36.45 g of $Mg(NO_3)_2 \cdot 6H_2O$ and 13.60 g of $Al(NO_3)_3 \cdot 9H_2O$, dissolved in 67.79 g of Milli-Q water, with a molar concentration of Al+Mg of 1.5. The second solution contained 12.53 g of NaOH and 16.16 g of $Na_2CO_3$ in 89.63 g of Milli-Q water and was used to produce the adequate precipitation of the Al and Mg species and to set the pH of the total mixture at about 13. Both solutions were added, at a total flow velocity of 20 ml/h for about 4 hours to a container under vigorous stirring at room temperature. A gel formed that was aged at room temperature for 1-2 hours after which time it was filtered and washed with distilled water until the carbonate was not detected in the filtered liquid (at pH about 7). Subsequently, the solid was dried in an oven at 60° C. for 18 hours, calcined in air at 450° C. to produce a mixed oxide, designated HT-4, having a Mg:Al molar ratio about 3.80 and a surface area (BET method) of 257 m2/g.

0.70% Pd/HT-1 catalyst was prepared by impregnating the HT-1 catalyst described above with Pd (1.0% by weight, theoretical). Impregnation was done by means of the incipient wetness impregnation method using 0.0360 g of $Pd(NH_3)_4Cl_2.6H_2O$ dissolved in 2 ml of Milli-Q water to impregnate 1.4086 g of HT-1. Once impregnated, the solid obtained was dried in an oven at 100° C. for 12 hours after which time it was calcined in air at 450° C. for 6 hours and then reduced at 450° C. in an $H_2$ atmosphere for 3 hours. The resulting Pd/HT-1 material contained about 0.70% by weight of Pd as characterized by chemical analysis and ICP-MS, 0.78% Pd/HT-3 catalyst was prepared by impregnating the HT-3 catalyst described above with Pd (1.0% by weight, theoretical). Impregnation was done by means of the incipient wetness impregnation method using 0.0308 g of $Pd(NH_3)_4Cl_2.6H_2O$ dissolved in 2 ml of Milli-Q water to impregnate 1.4030 g of HT-3. Once impregnated, the solid obtained was dried in an oven at 100° C. for 12 hours after which time it was calcined in air at 450° C. for 6 hours and then reduced at 450° C. in an $H_2$ atmosphere for 3 hours. The resulting Pd/HT-3 material contained about 0.78% by weight of Pd as characterized by chemical analysis and ICP-MS, 0.77% Pd/HT-4 catalyst was prepared by impregnating the HT-4 catalyst described above with Pd (1.0% by weight, theoretical). Impregnation was done by means of the incipient wetness impregnation method using 0.030 g of $Pd(NH_3)_4Cl_2.6H_2O$ dissolved in 2 ml of Milli-Q water to impregnate 1.014 g of HT-4. Once impregnated, the solid obtained was dried in an oven at 100° C. for 14-16 hours after which time it was calcined in air at 450° C. for 3-4 hours and then reduced at 350° C. in an $H_2$ atmosphere for 3 hours. The resulting Pd/HT-4 material contained about 0.77% by weight of Pd as characterized by chemical analysis and ICP-MS, 0.77% Pd/0.2% V/HT-1 catalyst was prepared by impregnating the HT-1 catalyst described above with Pd (1.0% by weight theoretical) and V (0.2% by weight theoretical). Impregnation was done by means of the incipient wetness impregnation method in two successive steps. In the first step, 0.0353 g of $Pd(NH_3)_4Cl_2.6H_2O$ dissolved in 2 ml of Milli-Q water was used to impregnate 1.4037 g of HT-1. Once impregnated, the solid obtained was dried in an oven at 100° C. for 12 hours. In the second step, the dried solid was impregnated with 0.0098 g of $NH_4VO_3$ dissolved in 1 ml of Milli-Q water and 1 ml of oxalic acid 0.2 M. Once impregnated, the solid obtained was dried in an oven at 100° C. for 12 hours after which time it was calcined in air at 450° C. for 6 hours and then reduced at 350° C. in an $H_2$ atmosphere for 3 hours. The resulting Pd/V/HT-1 material contained about 0.77% by weight of Pd and about 0.2% in weight of V as characterized by chemical analysis and ICP-MS, 0.75% Pd/0.24% V/HT-3 catalyst was prepared by impregnating the HT-3 catalyst describe above with Pd (1.0% by weight, theoretical) and V (0.2% by weight, theoretical). Impregnation was performed by means of the incipient wetness impregnation method in two successive steps. In the first step, 0.03 g of $Pd(NH_3)_4Cl_2.6H_2O$ dissolved in 2 ml of Milli-Q water were used to impregnate 1.2094 g of HT-3. Once impregnated, the solid obtained was dried in an oven at 100° C. for 12 hours. In the second step, the dried solid was impregnated with 0.0084 g of $NH_4VO_3$ dissolved in 0.5 ml of Milli-Q water and 1 ml of oxalic acid 0.2 M. Once impregnated, the solid obtained was dried in an oven at 100° C. for 12 hours after which time it was calcined in air at 450° C. for 6 hours and then reduced at 450° C. in an $H_2$ atmosphere for 3 hours. The resulting Pd/V/HT-3 material contained about 0.75% by weight of Pd and about 0.24% in weight of V as characterized by chemical analysis and ICP-MS, 0.97% Pd/1% V/HT-4 catalyst was prepared by impregnating the HT-4 catalyst described above with Pd (1.0% by weight theoretical) and V (2.0% by weight, theoretical). Impregnation was performed by means of the incipient wetness impregnation method in two successive steps. In the first step, 0.0270 g of $Pd(NH_3)_4Cl_2.6H_2O$ dissolved in 2 ml of Milli-Q water was used to impregnate 1.0 g of HT-4. In the second step, the solid was impregnated V (2.0%, theoretical) with 0.0460 g of $NH_4VO_3$ dissolved in 2 ml of Milli-Q water. Once impregnated, the solid obtained was dried in an oven at 100° C. for 14-16 hours after which time it was calcined in air at 450° C. for 6 h and then reduced at 350° C. in an $H_2$ atmosphere for 3 hours. The resulting Pd/V/HT-4 material contained about 0.97% by weight of Pd and about 1.0% in weight of V as characterized by chemical analysis and ICP-MS, 0.29% Ga/HT-4 catalyst was prepared by a standard co-precipitation process using two solutions. The first solution contained 29.89 g of $Mg(NO_3)_2.6H_2O$, 10.90 g of $Al(NO_3)_3.9H_2O$ and 0.06 g of $Ga(NO_3)_3.9H_2O$ dissolved in 55.2 ml of Milli-Q water, with a molar concentration of (Al+Mg+Ga) of 1.5. The second solution contained 12.52 g of NaOH and 10.52 g of $Na_2CO_3$ in 72.6 ml of Milli-Q water, and was used to produce the adequate precipitation of the Mg, Al and Ga species, and to set the pH of the total mixture at about 13. Both solutions were added, at a total flow velocity of 30 ml/h for about 4 hours to a container under vigorous stirring at room temperature. A gel formed that was aged at room temperature for 1-2 hours after which time it was filtered and washed with distilled water until the carbonate was not detected in the filtered liquid (at pH about 7). The solid obtained was dried in an oven at 60° C. for 14-16 hours. The hydrotalcite (Ga-HT-4) obtained was calcined in air at 450° C. for 3-4 hours to obtain a mixed oxide having a Mg:Al molar ratio of about 3.8, a Ga content of 0.29% by weight (measured by chemical analysis and ICP-MS), and a surface area (BET method) of 262 $m^2/g$.

0.87% Pd/0.29% Ga/HT-4 catalyst was prepared by the process describe above in connection with the 0.29% Ga/HT-4 catalyst wherein the incorporation of Pd (1.0% by weight, theoretical) into the Ga-HT-4 material was performed by means of the incipient wetness impregnation method with 0.03 g of $Pd(NH_3)_4Cl_2.6H_2O$ dissolved in 1.7 ml of Milli-Q water, to impregnate 1.1 g of 0.29% Ga-HT-4. The solid obtained was dried in an oven at 100° C. for 14-16 hours after which time it was calcined in air at 450° C. for 3-4 hours and then reduced at 350° C. in an $H_2$ atmosphere for 3 hours. The resulting Pd/0.29% Ga-HT-4 material contained about 0.87% by weight of Pd as characterised by chemical analysis and ICP-MS.

0.97% Pd/0.29% V/0.29% Ga/HT-4 catalyst was prepared by the process describe above in connection with the 0.29% Ga/HT-4 catalyst wherein the incorporation of Pd (1.0% by weight, theoretical) and V (0.2% by weight, theoretical) into the Ga-HT-4 material was performed by means of the incipient wetness impregnation method in two successive steps. In the first step, 0.0355 g of Pd(NH$_3$)$_4$Cl$_2$.6H$_2$O dissolved in 2 ml of Milli-Q water was used to impregnate 1.4072 g of 0.29% Ga-HT-4. The solid obtained was dried in an oven at 100° C. for 14-16 hours after which time V (0.2%, theoretical) was impregnated into the solid with 0.0096 g of NH$_4$VO$_3$ dissolved in 1 ml of Milli-Q water and 1 ml of oxalic acid 0.2 M. The solid was dried in an oven at 100° C. for 12 hours after which time it was calcined in air at 450° C. for 6 hours and then reduced at 350° C. in an H$_2$ atmosphere for 3 hours. The resulting Pd/V/0.29% Ga-HT-4 material contained about 0.97% by weight of Pd and about 0.29% of V as characterised by chemical analysis and ICP-MS.

4.9% Cu/HT-4 catalyst was prepared by means of a standard co-precipitation process using two solutions. The first solution contained 30.08 g of Mg(NO$_3$)$_2$.6H$_2$O, 10.44 g of Al(NO$_3$)$_3$.9H$_2$O and 1.17 g of Cu(NO$_3$)$_2$.3H$_2$O dissolved in 57.62 ml of Milli-Q water, with a molar concentration of (Al+Mg+Cu) of 1.5. The second solution contained 13.05 g of NaOH and 10.52 g of Na$_2$CO$_3$ in 74.71 ml of Milli-Q water, and was used to produce the adequate precipitation of the Mg, Al and Cu species, and to set the pH of the total mixture at about 13. Both solutions were added (total flow velocity=30 ml/h for about 4 hours) to a container under vigorous stirring at room temperature. A gel formed that was aged at room temperature for 1 to 2 hours after which time it was filtered and washed with distilled water until the carbonate was not detected in the filtered liquid (at pH about 7). The solid was dried in an oven at 60° C. for 18 hours and the hydrotalcite (Cu-HT-4) obtained was calcined in air at 450° C. for 3-4 hours to obtain a mixed oxide with a Mg:Al molar ratio of about 3.8, a Cu content of 4.9% by weight (characterized by chemical analysis and ICP-MS) and a surface area (BET method) of 190.08 m2/g.

0.98% Pd/0.2% V/4.9% Cu/HT-4 catalyst was prepared generally according to the method for preparing the 4.9% Cu/HT-4 catalyst described above wherein the incorporation of Pd (1.0% by weight, theoretical) and V (0.2% by weight, theoretical) into the 4.9% Cu-HT-4 material (Mg+Cu/Al≈4) was performed by means of the incipient wetness impregnation method in two successive steps. In the first step, 0.035 g of Pd(NH$_3$)$_4$Cl$_2$.6H$_2$O dissolved in 2 ml of Milli-Q water was used to impregnate 1.4 g of 4.9% Cu-HT-4. The solid obtained was dried in an oven at 100° C. for 12 hours. The solid was impregnated with V (0.2%, theoretical) with 0.009 g of NH$_4$VO$_3$ dissolved in 1 ml of Milli-Q water and 1 ml of oxalic acid 0.2 M. The impregnated solid was dried in an oven at 100° C. for 12 hours after which time it was calcined in air at 450° C. for 6 hours and then reduced at 350° C. in an H$_2$ atmosphere for 3 hours. The resulting 0.98% Pd/0.2% V/4.9% Cu/HT-4 material contained about 0.98% by weight of Pd and 0.20% of V as characterized by chemical analysis and ICP-MS, Example 2

The catalytic activity for the conversion of ethanol to n-butanol and ethanol and n-hexanol to n-octanol by Guerbet condensation was evaluated for various catalysts described above. In each of the experiments, 1750 mg (38 mmoles) of ethanol, 1790 mg (17.5 mmoles) n-hexanol and 350 mg of one of the above-described catalytic materials were introduced into a stirred 12 ml stainless steel autoclave reactor lined with PEEK (polyether ethyl ketone). The reactor was hermetically closed, and the system contained a first connector to a pressure meter (manometer), a second connector for gas loading and a sampling outlet. The reactor was initially pressurized with 24 bars of N$_2$, and heated to 250° C. to form a gas under continuous stirring, until the total system pressure reached about 35-40 bars (reaction time=0). Liquid samples of from about 50 to 100 µl were taken after 5 hours of reaction time. The samples were filtered and diluted in a 2% by weight of chlorobenzene in acetonitrile standard solution, and analyzed by means of gas chromatography in a GC-3900 Varian equipped with an FID detector and a 60-m TRB-624 capillary column.

The results are reported in Table 1 below wherein conversion is calculated by: ((starting moles−final moles)/(starting moles))*100; and yield is calculated by: ((moles of product)/(moles of all products))*(Ethanol conversion/100). In Table 1, "Exp." refers to experiment number, "Cony. EtOH" refers to ethanol conversion, "Cony. Hex" refers to n-hexanol conversion, "Yield BuOH" refers to n-butanol yield, "Yield OcOH" refers to n-octanol yield, and "Yield C$_{4+}$OH" refers to total yield of linear alcohols having 4 our more carbon atoms (including n-butanol and n-octanol) wherein "Lin" refers to linear and "Bran" refers to branched.

TABLE 1

| Exp. | Catalyst | Conv. EtOH | Conv. HeOH | Yield BuOH | Yield OcOH | Yield C$_{4+}$OH Lin. | Bran. |
|---|---|---|---|---|---|---|---|
| 1 | HT-1 | 11.4 | 3.3 | 0.25 | 0.18 | 0.4 | 0 |
| 2 | HT-3 | 11.2 | 2.8 | 1.50 | 1.08 | 2.5 | 0 |
| 3 | HT-4 | 22.3 | 3.4 | 10.56 | 3.95 | 14.9 | 0.4 |
| 4 | 0.70% Pd/HT-1 | 36.6 | 10.3 | 14.50 | 6.20 | 21.7 | 0.9 |
| 5 | 0.78% Pd/HT-3 | 34.7 | 8.7 | 9.44 | 4.24 | 14.4 | 1.3 |
| 6 | 0.77% Pd/HT-4 | 34.5 | 8.6 | 13.21 | 6.42 | 21.3 | 1.0 |
| 7 | 0.77% Pd/0.20% V/HT-1 | 61.6 | 23.2 | 11.61 | 7.82 | 25.4 | 1.4 |
| 8 | 0.75% Pd/0.24% V/HT-3 | 76.2 | 18.0 | 17.57 | 19.55 | 42.2 | 2.4 |
| 9 | 0.97% Pd/1.0% V/HT-4 | 37.4 | 11.1 | 15.46 | 8.55 | 23.0 | 1.0 |
| 10 | 0.29% Ga/HT-4 | 26.4 | 4.6 | 8.77 | 3.78 | 12.6 | 0.4 |
| 11 | 0.87% Pd/0.29% Ga/HT-4 | 42.6 | 21.3 | 16.52 | 5.69 | 19.0 | 1.1 |

TABLE 1-continued

| Exp. | Catalyst | Conv. EtOH | Conv. HeOH | Yield BuOH | Yield OcOH | Yield $C_{4+}$OH Lin. | Bran. |
|---|---|---|---|---|---|---|---|
| 12 | 0.97% Pd/0.29% V/0.29% Ga/HT-4 | 40.9 | 10.7 | 14.93 | 8.3 | 25.6 | 1.1 |
| 13 | 4.9% Cu/HT-4 | 22.4 | 8.0 | 4.03 | 4.99 | 9.6 | 0.8 |
| 14 | 0.98% Pd/0.2% V/4.9% Cu/HT-4 | 36.1 | 7.9 | 7.28 | 3.87 | 13.1 | 0.4 |

The results show that the incorporation of vanadium into hydrotalcite-derived catalysts with different Mg/Al ratios in their structure achieve higher yields both to n-butanol and to n-octanol, and in general, higher yield to $C_{4+}$ alcohols and improved catalytic activity (ethanol and n-hexanol conversion) as compared to analog catalysts not containing vanadium.

Comparison of the results of experiments 3, 6 and 9 to 12 shows that the incorporation of vanadium into hydrotalcite-derived catalysts comprising Ga in the structure gives higher yields to n-octanol, and in general, higher yield to $C_{4+}$ alcohols than analogue catalysts without vanadium. This effect occurs even with V concentrations lower than 0.3%, as it can be seen in FIG. 4. This indicates the higher stability of the catalysts under reaction conditions.

Comparison of the results of experiments 6, 8, 9, 11, 13 and 14 shows that the incorporation of vanadium into hydrotalcite-derived catalysts with different Mg/Al ratios gives higher yields to n-octanol, and in general, higher yield to $C_{4+}$ alcohols than analogue catalysts without vanadium. However, the production of $C_{4+}$OH decreases substantially when the catalyst comprises Cu in their structure, even in the presence of Pd and V. This indicates the higher stability of the catalysts under reaction conditions.

Example 3

The catalytic activity for catalysts 0.77% Pd/HT-4, 0.97% Pd/1.0% V/HT-4 and 0.87% Pd/0.29% Ga/HT-4 were evaluated for a reaction mixture comprising ethanol without n-hexanol. In each of the experiments, 3500 mg (76 mmoles) of ethanol and 200 mg catalyst were introduced into a stirred 12 ml stainless steel autoclave reactor lined with PEEK. The reactor was hermetically closed, and the system contained a first connector to a pressure meter (manometer), a second connector for gas loading and a sampling outlet. The reactor was initially pressurized with 24 bar of $N_2$, and heated to 200° C. to form a gas with continuous stirring, reaching the full system pressure to about 30 bar (reaction time=0). Liquid samples of from about 50 to 100 ul were taken after 5 hours of reaction time. The samples were filtered and diluted in a standard solution of chlorobenzene 2% by weight in acetonitrile, and analyzed by gas chromatography on a Varian 3900 GC-FID equipped with a capillary column and TRB-624. The conversion in mole percent ethanol ("Cony. EtOH") was calculated by: (initial moles ethanol−final moles ethanol)/(initial moles ethanol)*100. The results are presented in Table 2 below where "Lin." refers to linear and "Bran." refers to branched. The values in brackets refer to molar % yield of products.

TABLE 2

| Ex. | Catalyst | Conv. EtOH | Select. nBuOH | Select. nHeOH | Select. nOctOH | Select. $C_4$+ Alcohols Lin. | Bran. |
|---|---|---|---|---|---|---|---|
| 1 | 0.77% Pd/HT-4 | 15.5 | 76.9 [11.9] | 12.3 [1.9] | 2.6 [0.4] | 93.9 [14.6] | 1.2 [0.2] |
| 2 | 0.97% Pd/1.0% V/HT-4 | 14.0 | 66.8 [9.4] | 13.0 [1.8] | 1.6 [0.2] | 83.1 [11.6] | 0.5 [0.1] |
| 3 | 0.87% Pd/0.29% Ga-HT-4 | 15.8 | 76.5 [12.1] | 12.0 [1.9] | 1.9 [0.3] | 1.4 [14.4] | 1.6 [0.3] |

Other reaction products included aldehydes (ethanal, butanal, hexanal), ethyl acetate and diethoxyethane.

These results show that catalysts derived from hydrotalcite and containing Pd, and the Pd/Ga and Pd/V combinations in the structure provide higher yields n-butanol and 1-hexanol, while yields of n-octanol and especially $C_{4+}$ alcohols are significantly reduced thus maximizing n-butanol yield.

Example 4

The catalytic activity for catalysts 0.77% Pd/HT-4, 0.97% Pd/1.0% V/HT-4, 0.87% Pd/0.29% Ga/HT-4 and 0.97% Pd/0.29% V/0.29% Ga/HT-4 were evaluated for a reaction mixture comprising n-butanol and no ethanol or n-hexanol. In each of the experiments, 35000 mg (47 mmoles) of n-butanol, 1790 mg and 200 mg catalyst were introduced into a stirred 12 ml stainless steel autoclave reactor lined with PEEK. The reactor was hermetically closed, and the system contained a first connector to a pressure meter (manometer), a second connector for gas loading and a sampling outlet. The reactor was initially pressurized with 24 bar of $N_2$, and heated to 250° C. to form a gas with continuous stirring, reaching the full system pressure to about 35-40 bars (reaction time=0). Liquid samples of from about 50 to 100 ul were taken after 5 hours of reaction time. The samples were filtered and diluted in a standard solution of chlorobenzene 2% by weight in acetonitrile, and analyzed by gas chromatography on a Varian 3900 GC-FID equipped with a capillary column and TRB-624. The conversion and selectivity was calculated as per above. The yield was calculated as: {[(moles of product)/(total moles of all products)]*(EtOH conversion)}/100. The results are presented in Table 3 below where "Lin." refers to linear and "Bran." refers to branched. The values in brackets refer to molar % yield of products.

TABLE 3

| Ex. | Catalyst | Conv. n-BuOH | Select. n-butanal | Select. Other Ald. | Select. n-OctOH | Yield C4+ Alcohols Lin. | Bran. |
|---|---|---|---|---|---|---|---|
| 1 | 0.77% Pd/HT-4 | 17.1 | 16.9 [2.9] | 3.5 [0.6] | 0.6 [0.1] | 37.7 [6.4] | 30.9 [5.3] |
| 2 | 0.97% Pd/1.0% V/HT-4 | 35.5 | 3.9 [1.4] | 1.6 [0.6] | 1.7 [0.6] | 63.3 [22.5] | 18.0 [6.4] |
| 3 | 0.87% Pd/0.29% Ga/HT-4 | 32.9 | 5.3 [1.7] | 1.8 [0.6] | 0.6 [0.2] | 64.0 [21.1] | 20.6 [6.8] |
| 4 | 0.97% Pd/0.29% V/0.29% Ga/HT-4 | 25.9 | 7.4 [1.9] | 2.0 [0.5] | 0.7 [0.2] | 57.0 [14.8] | 25.2 [6.5] |

The results show that the catalyst of the invention with butanol as a reagent does not yield octanol in a high percentage. Further, the percentage of branched products is higher than if neither hexanol or ethanol is utilized in the reaction mixture. It is therefore shown that hexanol and ethanol is required to obtain high yields of octanol.

Example 5

The composition of butanol reactor feed and product streams and octanol reactor feed and product streams was simulated for a process depicted in FIG. 2. The process was simulated with Aspen Plus version 7.1. A non-random two liquid (NRTL) activity coefficient model with the Redlich-Kwong equation of state, with non-condensible components defined by Henry's law coefficients was used. The butanol and hexanol reactor were modeled with kinetic reactors and the distillation columns were modeled with Radfrac models. The simulated results are presented in Table 5 in mole %.

TABLE 5

| Component | Butanol Reactor Feed | Butanol Reactor Product | Octanol Reactor Feed | Octanol Reactor Product |
|---|---|---|---|---|
| n-butanol | 0.03 | 10.6 | 0.015 | 2.34 |
| 2-butanol | 0.3 | 0.38 | 0.15 | 0.24 |
| Ethanol | 80.2 | 45.6 | 42 | 28.4 |
| Water | 2.3 | 16.2 | 1.17 | 9.37 |
| Acetaldehyde | 0.009 | 0.94 | 0.012 | 0.49 |
| Butyraldehyde | 0.44 | 0.57 | 0.23 | 0.029 |
| Hexanaldehyde | 0 | 0 | 0.005 | 0.47 |
| ethyl acetate | 0.066 | 0.12 | 0.03 | 0.14 |
| n-hexanol | 0 | 1.46 | 32.0 | 25.4 |
| n-octanol | 0 | 0.2 | 0 | 2.5 |
| n-decanol | 0 | 0.034 | 0 | 0.29 |
| 2-ethyl-1-butanol | 0 | 0.26 | 1.05 | 1.05 |
| 2-ethyl-1-hexanol | 0 | 0.056 | 0 | 0.35 |
| 2-butyl-1-octanol | 0 | 0 | 0 | 0.31 |
| Pentane | 0 | 0 | 0.015 | 0.57 |
| Methane | 0.096 | 0.43 | 0.14 | 0.30 |
| Ethane | 0 | 0.27 | 0.09 | 0.11 |
| Propane | 0 | 0.09 | 0.025 | 0.06 |
| hydrogen | 16.0 | 20.3 | 22.2 | 25.2 |

TABLE 5-continued

| Component | Butanol Reactor Feed | Butanol Reactor Product | Octanol Reactor Feed | Octanol Reactor Product |
|---|---|---|---|---|
| carbon dioxide | 0.28 | 0.85 | 0.27 | 0.69 |
| carbon monoxide | 0.32 | 1.65 | 0.6 | 1.63 |

Examples 6 to 11

In the following examples 6 to 11, "Exp" refers to experiment number, "° C." refers to the reaction temperature, "Bar" refers to the reaction pressure, "EtOH rate" refers to the ethanol feed rate in moles per hour. "H2/EtOH" refers to the mole ratio of hydrogen to ethanol, "LHSV" refers to reactor liquid hourly space velocity, "x-EtOH" refers to the ethanol conversion rate, "s-BuOH" refers to selectivity to butanol, "Yield" refers to butanol yield, "AA/EtOH" refers to the mole ratio of acetaldehyde to ethanol and "CO/EtOH" refers to the mole ratio of carbon monoxide to ethanol.

Example 6

In a fixed-bed reactor, made out of 154-cm long and 2.5 cm diameter stainless steel reactor, a constant flux of gas phase reactants was contacted with 100 g of a metal oxide Guerbet catalyst comprising palladium. The reactor was connected to a synthesis loop, containing a pressure meter (manometer), a regent input connector and an outlet connector. Reactor operating pressure was controlled by a valve sited at the outlet stream. After the desired operating pressure was achieved, reagent was introduced to the reactor synthesis loop. The composition of the outlet stream was measured by gas chromatography in a GC-Agilent 7890N equipped with a FID and TCD detector, a capillary column Rt-U PLOT of 30 m and two packed columns in series (PORAPPACK QS, 3.6-m long, and CARBOXEN 1000, 4.5-m long).

The ethanol conversion, butanol selectivity and butanol yield results, measured after it was determined that the outlet stream composition was stable, are reported in Table 6A below. The ratios of n-butanol to hexanol (BuOH/HexOH), octanol (BuOH/OctOH), i-Butanol (BuOH/iBuOH), 2-Butanol (BuOH/2-BuOH) and 2-ethyl-1-butanol (BuOH/2-Et-1-BuOH) in the product stream are reported in Table 6B below.

TABLE 6A

| | Feed Stream | | | | | Product Stream | | |
|---|---|---|---|---|---|---|---|---|
| Exp | ° C. | Bar | EtOH rate | H$_2$/EtOH | LHSV | x-EtOH | s-BuOH | Yield |
| 101 | 220 | 28 | 2.84 | 0.4 | 1.4 | 5.76 | 79.30 | 4.57 |
| 102 | 240 | 28 | 2.84 | 0.4 | 1.4 | 12.08 | 78.56 | 9.49 |
| 103 | 250 | 28 | 2.84 | 0.4 | 1.4 | 15.70 | 77.44 | 12.16 |
| 104 | 250 | 28 | 3.49 | 0.39 | 1.75 | 14.48 | 77.48 | 11.22 |
| 105 | 250 | 40 | 3.49 | 0.39 | 1.75 | 12.31 | 77.52 | 9.54 |
| 106 | 250 | 50 | 3.49 | 0.39 | 1.75 | 11.65 | 78.25 | 9.12 |

TABLE 6A-continued

| | Feed Stream | | | | | Product Stream | | |
|---|---|---|---|---|---|---|---|---|
| Exp | ° C. | Bar | EtOH rate | H$_2$/EtOH | LHSV | x-EtOH | s-BuOH | Yield |
| 107 | 220 | 30 | 2.84 | 0.1 | 1.4 | 10.20 | 76.70 | 7.82 |
| 108 | 220 | 28 | 2.84 | 0.4 | 1.4 | 5.76 | 79.30 | 4.57 |
| 109 | 250 | 28 | 2.84 | 0.4 | 1.4 | 15.70 | 77.44 | 12.16 |
| 110 | 250 | 28 | 3.49 | 0.39 | 1.75 | 14.48 | 77.52 | 11.23 |
| 111 | 245 | 45 | 3.00 | 0.5 | 1.5 | 10.94 | 81.30 | 8.89 |
| 112 | 230 | 30 | 2.40 | 0.2 | 1.2 | 9.81 | 79.15 | 7.76 |
| 113 | 230 | 60 | 3.58 | 0.2 | 1.8 | 4.92 | 83.70 | 4.12 |
| 114 | 230 | 30 | 3.58 | 0.8 | 1.8 | 4.71 | 82.43 | 3.88 |
| 115 | 230 | 60 | 2.40 | 0.8 | 1.2 | 4.60 | 71.07 | 3.27 |
| 116 | 260 | 30 | 2.40 | 0.8 | 1.2 | 13.28 | 78.78 | 10.46 |
| 117 | 260 | 60 | 3.58 | 0.8 | 1.8 | 10.04 | 83.85 | 8.42 |
| 118 | 245 | 45 | 3.00 | 0.5 | 1.5 | 9.04 | 82.06 | 7.42 |
| 119 | 260 | 60 | 2.40 | 0.2 | 1.2 | 21.24 | 78.59 | 16.69 |
| 120 | 260 | 30 | 3.58 | 0.2 | 1.8 | 18.63 | 76.49 | 14.25 |
| 121 | 260 | 60 | 2.40 | 0.2 | 1.2 | 18.53 | 79.24 | 14.68 |
| 122 | 230 | 30 | 3.58 | 0.26 | 1.8 | 6.71 | 80.81 | 5.42 |

TABLE 6B

| Exp | BuOH/HexOH | BuOH/OctOH | BuOH/iBuOH | BuOH/2-BuOH | BuOH/2-Et-1-BuOH |
|---|---|---|---|---|---|
| 101 | 18.44 | 454.97 | 323.80 | >1000 | 99.85 |
| 102 | 14.64 | 198.17 | 440.04 | 240.45 | 78.81 |
| 103 | 13.72 | 168.08 | 436.84 | 258.30 | 74.41 |
| 104 | 14.23 | 182.98 | 451.05 | 250.52 | 80.92 |
| 105 | 15.51 | 212.50 | 442.88 | 236.81 | 91.01 |
| 106 | 15.82 | 231.86 | 621.89 | 229.92 | 94.34 |
| 107 | 10.83 | 112.23 | 290.73 | >1000 | 55.33 |
| 108 | 18.44 | 454.97 | 323.80 | >1000 | 99.85 |
| 109 | 13.72 | 168.08 | 436.84 | 258.30 | 74.41 |
| 110 | 14.23 | 182.98 | 451.05 | 250.52 | 80.92 |
| 111 | 16.91 | 266.65 | 583.66 | 214.09 | 94.79 |
| 112 | 15.66 | 240.96 | 339.75 | 218.56 | 87.68 |
| 113 | 24.84 | 633.96 | 379.03 | 155.18 | 146.80 |
| 114 | 33.86 | 1104.27 | 378.20 | 107.06 | 201.66 |
| 115 | 30.94 | 1902.63 | 105.50 | 105.50 | 210.25 |
| 116 | 24.88 | 469.54 | 464.80 | 127.84 | 146.85 |
| 117 | 29.37 | 801.26 | 547.82 | 122.70 | 184.25 |
| 118 | 21.46 | 399.23 | 437.18 | 136.70 | 140.03 |
| 119 | 11.30 | 122.25 | 726.00 | 244.37 | 66.52 |
| 120 | 12.17 | 134.55 | 422.38 | 209.57 | 78.21 |
| 121 | 12.17 | 145.28 | 764.18 | 230.90 | 74.47 |
| 122 | 19.60 | 386.46 | 311.29 | 146.17 | 132.17 |

Example 7

Experiments were performed following the protocol detailed in Example 6. The ethanol conversion, butanol selectivity and butanol yield results are reported in Table 7A below. The ratios of n-butanol to hexanol (BuOH/HexOH), octanol (BuOH/OctOH), i-Butanol (BuOH/iBuOH), and 2-Butanol (BuOH/2-BuOH) in the product stream are reported in Table 7B below.

TABLE 7A

| | Feed Stream | | | | | Product Stream | | |
|---|---|---|---|---|---|---|---|---|
| Exp | ° C. | Bar | EtOH rate | H$_2$/EtOH | LHSV | x-EtOH | s-BuOH | Yield |
| 201 | 245 | 45 | 3.00 | 0.5 | 1.5 | 9.77 | 82.93 | 8.10 |
| 202 | 231 | 60 | 2.40 | 0.4 | 1.2 | 6.19 | 85.00 | 5.26 |
| 203 | 248 | 57 | 2.40 | 0.4 | 1.2 | 12.32 | 82.57 | 10.17 |
| 204 | 244 | 63 | 1.80 | 0.35 | 0.9 | 12.10 | 82.58 | 9.99 |
| 205 | 256 | 75 | 2.00 | 0.35 | 1 | 15.92 | 82.01 | 13.06 |
| 206 | 257 | 30 | 2.40 | 0.42 | 1.2 | 18.11 | 77.39 | 14.02 |
| 207 | 257 | 30 | 3.60 | 0.43 | 1.8 | 14.12 | 78.76 | 11.12 |
| 208 | 260 | 30 | 3.60 | 0.4 | 1.8 | 15.67 | 77.84 | 12.19 |
| 209 | 265 | 75 | 2.40 | 0.4 | 1.2 | 19.11 | 80.30 | 15.35 |
| 210 | 263 | 51 | 1.80 | 0.55 | 0.9 | 21.32 | 79.10 | 16.87 |
| 211 | 254 | 49 | 2.40 | 0.4 | 1.2 | 15.17 | 80.68 | 12.24 |
| 212 | 254 | 40 | 2.40 | 0.4 | 1.2 | 15.93 | 79.79 | 12.71 |
| 213 | 245 | 45 | 3.00 | 0.5 | 1.5 | 9.06 | 82.06 | 7.43 |
| 214 | 260 | 60 | 3.60 | 0.4 | 1.8 | 14.36 | 79.84 | 11.47 |
| 215 | 260 | 30 | 3.60 | 0.4 | 1.8 | 15.77 | 77.28 | 12.18 |
| 216 | 260 | 70 | 3.60 | 0.4 | 1.8 | 15.16 | 77.51 | 11.75 |
| 217 | 245 | 45 | 3.00 | 0.5 | 1.5 | 9.39 | 82.16 | 7.71 |

TABLE 7A-continued

| | Feed Stream | | | | | Product Stream | | |
|---|---|---|---|---|---|---|---|---|
| Exp | °C. | Bar | EtOH rate | H₂/EtOH | LHSV | x-EtOH | s-BuOH | Yield |
| 218 | 250 | 50 | 2.40 | 0.4 | 1.2 | 13.11 | 80.54 | 10.56 |
| 219 | 250 | 60 | 2.40 | 0.31 | 1.2 | 13.90 | 81.17 | 11.29 |
| 220 | 250 | 60 | 2.40 | 0.68 | 1.2 | 10.40 | 83.78 | 8.71 |

TABLE 7B

| Exp | BuOH/HexOH | BuOH/OctOH | BuOH/iBuOH | BuOH/2-BuOH | BuOH/2-Et-1-BuOH |
|---|---|---|---|---|---|
| 201 | 18.34 | 258.53 | 584.83 | 139.31 | 122.83 |
| 202 | 22.64 | 477.10 | 425.24 | 134.24 | 142.59 |
| 203 | 16.33 | 224.38 | 481.95 | 171.13 | 118.97 |
| 204 | 15.94 | 203.06 | 513.85 | 164.79 | 101.71 |
| 205 | 14.59 | 170.88 | 530.92 | 185.85 | 91.37 |
| 206 | 12.88 | 125.37 | 359.87 | 171.93 | 83.00 |
| 207 | 15.91 | 192.99 | 339.29 | 174.85 | 106.73 |
| 208 | 14.88 | 171.78 | 335.57 | 161.63 | 98.63 |
| 209 | 13.09 | 146.68 | 544.99 | 201.47 | 83.12 |
| 210 | 12.56 | 129.63 | 504.05 | 193.98 | 77.51 |
| 211 | 14.93 | 181.84 | 436.44 | 177.83 | 96.12 |
| 212 | 14.27 | 168.38 | 408.94 | 176.66 | 91.67 |
| 213 | 20.96 | 374.31 | 466.86 | 132.67 | 141.10 |
| 214 | 13.72 | 146.99 | 461.59 | 178.41 | 94.02 |
| 215 | 13.41 | 132.82 | 359.38 | 169.79 | 91.68 |
| 216 | 14.85 | 136.60 | 347.50 | 159.42 | 102.17 |
| 217 | 19.22 | 296.05 | 421.94 | 138.52 | 131.78 |
| 218 | 14.75 | 163.69 | 457.37 | 173.25 | 97.45 |
| 219 | 13.70 | 161.93 | 485.39 | 190.26 | 89.56 |
| 220 | 19.35 | 298.55 | 600.06 | 148.33 | 131.60 |

Example 8

Experiments were performed following the protocol detailed in Example 6. The ethanol conversion, butanol selectivity and butanol yield results are reported in Table 8A below. The ratios of n-butanol to hexanol (BuOH/HexOH), octanol (BuOH/OctOH), i-Butanol (BuOH/iBuOH), and 2-Butanol (BuOH/2-BuOH) in the product stream are reported in Table 8B below.

TABLE 8A

| | Feed Stream | | | | | | Product Stream | | |
|---|---|---|---|---|---|---|---|---|---|
| Exp | °C. | Bar | EtOH rate | H₂/EtOH | AA/EtOH | LHSV | x-EtOH | s-BuOH | Yield |
| 301 | 231 | 60 | 2.38 | 0.4 | 0.01 | 1.2 | 5.66 | 84.57 | 4.79 |
| 302 | 254 | 49 | 2.38 | 0.4 | 0.01 | 1.2 | 15.27 | 81.73 | 12.48 |
| 303 | 254 | 40 | 2.38 | 0.4 | 0.01 | 1.2 | 15.80 | 81.82 | 12.93 |
| 304 | 256 | 75 | 1.98 | 0.35 | 0.01 | 1 | 15.40 | 83.32 | 12.83 |
| 305 | 260 | 30 | 3.56 | 0.4 | 0.01 | 1.8 | 15.42 | 82.23 | 12.68 |
| 306 | 263 | 51 | 1.78 | 0.55 | 0.01 | 0.9 | 20.41 | 81.33 | 16.60 |
| 307 | 265 | 75 | 2.38 | 0.4 | 0.01 | 1.2 | 18.24 | 82.52 | 15.05 |
| 308 | 260 | 30 | 3.56 | 0.2 | 0.01 | 1.8 | 18.43 | 77.65 | 14.31 |
| 309 | 260 | 60 | 3.56 | 0.4 | 0.01 | 1.8 | 13.82 | 82.91 | 11.45 |
| 310 | 260 | 30 | 3.56 | 0.4 | 0.01 | 1.8 | 15.45 | 81.18 | 12.54 |
| 311 | 260 | 60 | 3.56 | 0.8 | 0.01 | 1.8 | 10.65 | 85.75 | 9.13 |

TABLE 8B

| Exp | BuOH/HexOH | BuOH/OctOH | BuOH/iBuOH | BuOH/2-BuOH | BuOH/2-Et-1-BuOH |
|---|---|---|---|---|---|
| 301 | 18.37 | 303.05 | 332.98 | 137.53 | 104.25 |
| 302 | 12.83 | 137.25 | 392.29 | 192.74 | 78.00 |
| 303 | 12.55 | 121.92 | 368.71 | 192.19 | 78.91 |
| 304 | 13.41 | 150.51 | 494.32 | 204.24 | 81.61 |
| 305 | 13.66 | 142.65 | 332.52 | 181.08 | 89.29 |
| 306 | 11.97 | 114.87 | 505.93 | 204.04 | 73.36 |
| 307 | 12.72 | 133.20 | 520.59 | 216.79 | 78.82 |
| 308 | 9.83 | 72.46 | 340.54 | 224.50 | 63.74 |
| 309 | 12.90 | 133.35 | 420.50 | 220.32 | 84.83 |
| 310 | 13.02 | 128.38 | 373.88 | 192.07 | 84.48 |
| 311 | 17.79 | 241.92 | 563.87 | 155.26 | 116.68 |

Example 9

Experiments were performed following the protocol detailed in Example 6. Experiment A101 was run at 245° C. and all other experiments at 260° C., Experiments A211 and A212 contained BuOH in the feed at a rate of 1.16 mol/h (38 mol % of alcohol feed) and 3.92 mol/h (51 mol % of alcohol feed), respectively. The results are reported in Tables 9A and 9B below. In Table 9B, the product stream results are reported in mole % wherein PeOH refers to pentanol, 2-Et-1-BuOH refers to 2-ethyl-1-butanol, HexOH refers to hexanol, OctOH refers to octanol, DecOH refers to decanol, DodecOH refers to dodecanol, and TetOH refers to tetradecanol.

TABLE 9A

| | Feed Stream | | | | | | | Product Stream | | |
|---|---|---|---|---|---|---|---|---|---|---|
| Exp | Bar | EtOH rate | H$_2$/EtOH | LHSV | CO/EtOH | AA/EtOH | H$_2$O/EtOH | xEtOH | ssBuOH | Yield |
| A101 | 45 | 3.00 | 0.5 | 1.6 | — | — | — | 11.47 | 80.38 | 9.22 |
| A102 | 30 | 3.00 | 0.5 | 1.6 | — | — | — | 20.67 | 72.82 | 15.06 |
| A103 | 40 | 3.00 | 1 | 1.6 | — | — | — | 15.16 | 78.94 | 11.97 |
| A201 | 31 | 3.00 | 0.5 | 1.6 | — | — | 0.01 | 22.77 | 65.14 | 14.83 |
| A202 | 41 | 3.00 | 1 | 1.6 | — | — | 0.01 | 17.10 | 73.69 | 12.60 |
| A203 | 33 | 3.30 | 0.5 | 1.8 | — | — | 0.05 | 15.12 | 64.50 | 9.75 |
| A204 | 43 | 3.30 | 1 | 1.8 | — | — | 0.05 | 10.46 | 72.06 | 7.54 |
| A205 | 33.1 | 3.03 | 0.57 | 1.7 | — | 0.05 | — | 19.64 | 71.34 | 14.01 |
| A206 | 45 | 3.00 | 1.14 | 1.7 | — | 0.05 | — | 10.62 | 79.46 | 8.44 |
| A207 | 30 | 2.81 | 0.5 | 1.6 | — | 0.05 | — | 19.35 | 71.43 | 13.82 |
| A208 | 40 | 2.85 | 1 | 1.6 | — | 0.05 | — | 15.57 | 74.33 | 11.57 |
| A209 | 30 | 2.68 | 0.5 | 1.6 | — | 0.10 | — | 28.99 | 48.36 | 14.02 |
| A210 | 40 | 2.68 | 1 | 1.6 | — | 0.10 | — | 19.53 | 58.61 | 11.44 |
| A211 | 30 | 1.87 | 0.5 | 2.0 | — | — | — | 45.76 | 33.44 | 15.30 |
| A212 | 40 | 3.75 | 0.5 | 4.0 | — | — | — | 15.42 | 0.00 | 0.00 |
| A213 | 31 | 3.00 | 0.5 | 1.6 | 0.05 | — | — | 7.96 | 76.03 | 6.05 |
| A214 | 41 | 3.00 | 1 | 1.6 | 0.05 | — | — | 6.60 | 76.25 | 5.03 |

TABLE 9B

| Exp | BuOH | PenOH | 2-Et-1-BuOH | HexOH | OctOH | DecOH | DodecOH | TetOH |
|---|---|---|---|---|---|---|---|---|
| A101 | 80.4 | 0.11 | 1.2 | 8.6 | 0.92 | 0.14 | 0.09 | 0.04 |
| A102 | 72.8 | 0.18 | 1.75 | 12.2 | 2.39 | 0.69 | 0.19 | 0.07 |
| A103 | 78.9 | 0.15 | 1.17 | 8.91 | 1.11 | 0.17 | 0.08 | 0.04 |
| A201 | 65.1 | 0.34 | 2.28 | 13.7 | 3.89 | 2.13 | 1.01 | 0.38 |
| A202 | 73.7 | 0.2 | 1.74 | 11.8 | 2.16 | 0.6 | 0.17 | 0.05 |
| A203 | 64.5 | 0.16 | 2.66 | 15 | 3.67 | 1.25 | 0.43 | 0.18 |
| A204 | 72.1 | 0.2 | 2.02 | 11.6 | 1.83 | 0.35 | 0.11 | 0.06 |
| A205 | 71.3 | 0.19 | 2.43 | 14 | 3.27 | 1.22 | 0.47 | 0.18 |
| A206 | 79.5 | 0.15 | 1.3 | 9.28 | 1.18 | 0.21 | 0.08 | 0.04 |
| A207 | 71.4 | 0.19 | 2.1 | 13.5 | 3.02 | 1.05 | 0.35 | 0.12 |
| A208 | 74.3 | 0.21 | 1.98 | 12.2 | 2.5 | 0.97 | 0.34 | 0.15 |
| A209 | 48.4 | 0.23 | 3.32 | 15 | 5.76 | 4.31 | 4.48 | 3.74 |
| A210 | 58.6 | 0.18 | 3.05 | 14.8 | 4.95 | 0.03 | 2.55 | 1.38 |
| A211 | 33.4 | 0.3 | 5.33 | 36.2 | 7.3 | 1.95 | 0.73 | 0.21 |
| A212 | 0 | 0 | 8.64 | 61.1 | 7.56 | 1.44 | 0.39 | 0.09 |
| A213 | 76 | 0.2 | 0.52 | 4.1 | 0.31 | 0 | 0 | 0 |
| A214 | 76.3 | 0 | 0.42 | 3.11 | 0.17 | 0.07 | 0 | 0.05 |

Experiments A211 and A212 were terminated early because heavy compounds were generated that blocked the GC inlet. Acetaldehyde trials at a mole ratio of 0.2:1 to ethanol were stopped because the temperature increased to more than 30° C. above the set point.

Example 10

Experiments were performed following the protocol detailed in Example 6 but wherein the reactor was a 33 cm long and 0.83 cm diameter stainless steel fixed bed reactor, a constant flow of the reagents and 50 mL/minute of N$_2$ were fed to the reactor, a reactor catalyst loading of 3 grams was used, and a GC-Agilent 6890N apparatus was used. The ethanol conversion, butanol selectivity and butanol yield results are reported in Table 10A below. The ratios of n-butanol to hexanol (BuOH/HexOH), octanol (BuOH/OctOH), i-Butanol (BuOH/iBuOH), and 2-Butanol (BuOH/2-BuOH) in the product stream are reported in Table 10B below wherein "n.d." refers to not detected. Analysis indicated the absence of i-Butanol and 2-Butanol.

TABLE 10A

| | Feed Stream | | | | | | Product Stream | | | |
|---|---|---|---|---|---|---|---|---|---|---|
| Exp | ° C. | Bar | EtOH rate | H$_2$/EtOH | LHSV | AA/EtOH | x-EtOH | x-AA | s-BuOH | Yield |
| B101 | 220 | 76 | 0.079 | 0.95 | 1.2 | 0.01 | 8.3 | 74.9 | 87.04 | 7.2 |
| B102 | 240 | 76 | 0.079 | 0.68 | 1.2 | 0.01 | 9.5 | 60.3 | 84.97 | 8.0 |
| B103 | 250 | 76 | 0.079 | 0.68 | 1.2 | 0.02 | 10.9 | 79.8 | 83.81 | 9.1 |
| B104 | 250 | 76 | 0.079 | 0.95 | 1.2 | 0.02 | 9.0 | 87.3 | 84.11 | 7.6 |
| B105 | 250 | 66 | 0.079 | 0.95 | 1.2 | 0.02 | 13.4 | 86.2 | 84.12 | 11.2 |
| B106 | 250 | 76 | 0.056 | 1.01 | 0.93 | 0.11 | 9.4 | 95.2 | 66.21 | 6.2 |
| B107 | 220 | 76 | 0.056 | 1.45 | 0.93 | 0.11 | 11.6 | 96.0 | 66.48 | 7.7 |

TABLE 10B

| Exp | BuOH/HexOH | BuOH/OctOH | BuOH/2-Et-1-BuOH |
|---|---|---|---|
| B101 | 22.54 | n.d. | 110.81 |
| B102 | 16.60 | n.d. | 92.20 |
| B103 | 13.92 | n.d. | 73.10 |
| B104 | 15.79 | n.d. | 75.92 |
| B105 | 16.14 | n.d. | 78.77 |
| B106 | 5.73 | 36.80 | n.d. |
| B107 | 6.12 | 40.53 | n.d. |

Example 11

Experiments were performed following the protocol detailed in Example 6 at a temperature of 260° C., a pressure of 40 bara and at a LHSV of 1.84. Reactor gas stream and reactor product streams comprising n-butanol were continuously produced. The gas stream was recycled to the reactor and the product stream was fractionated to generate recycle ethanol and a product stream comprising n-butanol among other compounds. A mole ratio of hydrogen to ethanol of 0.4:1 was used in the reaction. No fresh hydrogen feed was introduced into the reactor. After operating times of start-up (i.e., fresh catalyst), 755 hours, 778 hours, 789 hours, 801 hours and 813 hours the gas and product stream comprising n-butanol were analyzed. The CO and $CO_2$ concentrations (in mole %) are reported in the table 11A below. The reactor product stream composition is also reported in the table below including the (i) the percent ethanol conversion ("xEtOH %"); (ii) ethyl acetate concentration ("EAc"), acetaldehyde concentration ("AA"), 2-butanol concentration ("2-BuOH"), n-butanol concentration ("n-BuOH"), pentanol concentration ("PentOH"), 2-ethyl-1-butanol concentration ("2-Et-1-BuOtH"), hexanol concentration ("HexOH"), 2-ethyl hexanol concentration ("2-Et-HexOH"), octanol concentration ("OctOH"), 2-ethyl-1-octanol concentration ("2-Et-1-OctOH"), decanol concentration ("DecOH"), and dodecanol concentration ("DodecOH") are reported in mole %; and (iii) butanol yield (BuOH %).

TABLE 11A

| | Fresh | 755 hours | 778 hours | 789 hours | 801 hours | 813 hours |
|---|---|---|---|---|---|---|
| CO | 0 | 0.022 | 0.022 | 0.051 | 0.031 | 0.024 |
| $CO_2$ | 0.014 | 0.116 | 0.1 | 0.099 | 0.108 | 0.107 |
| xEtOH % | 16.9 | 14.6 | 15.3 | 16.1 | 15.4 | 15.2 |
| EAc | 0.486 | 0.556 | 0.554 | 0.56 | 0.562 | 0.579 |
| AA | 2.81 | 2.88 | 2.95 | 2.88 | 3.06 | 3.22 |
| 2-BuOH | 1.08 | 1.02 | 1.18 | 1.06 | 1.08 | 1.1 |
| n-BuOH | 76.89 | 78.92 | 77.94 | 77.55 | 77.83 | 77.67 |
| PentOH | 0.165 | 0.066 | 0.214 | 0.174 | 0.176 | 0.185 |
| 2-Et-1-BuOH | 1.46 | 1.34 | 1.41 | 1.41 | 1.41 | 1.36 |
| HexOH | 11.74 | 10.8 | 11.32 | 11.69 | 11.53 | 11.46 |
| 2-Et—HexOH | 0.397 | 0.297 | 0.326 | 0.357 | 0.337 | 0.336 |
| OctOH | 2.2 | 1.77 | 1.97 | 2.09 | 1.96 | 2.03 |
| DecOH | 0.78 | 0.56 | 0.64 | 0.68 | 0.63 | 0.63 |
| 2-Et-1-OctOH | 0.139 | 0.1 | 0.12 | 0.135 | 0.121 | 0.132 |
| DodecOH | 0.278 | 0.211 | 0.231 | 0.241 | 0.229 | 0.208 |
| BuOH % | 13.02 | 11.5 | 11.94 | 12.47 | 12.02 | 11.8 |

The results of this experiment demonstrate that n-butanol can be prepared in high yield and selectivity in a continuous process utilizing only recycled hydrogen (i.e., in the absence of fresh or make-up hydrogen), recycled ethanol, and without purification of recycle gas.

What is claimed is:

1. A method of preparing n-octanol, the method comprising:
    forming an octanol reaction mixture gas comprising a source of ethanol, a source of hydrogen, and a source of n-hexanol comprising at least 50 mole percent recovered n-hexanol, the octanol reaction mixture comprising a mole ratio ethanol to n-hexanol of from about 0.3:1 to about 3:1;
    reacting the octanol reaction mixture gas in a continuous method by contact with a Guerbet heterogeneous metal oxide catalyst in a gas phase octanol reactor having a fixed catalyst bed at a reaction temperature of from about 150° C. to 450° C. and a reaction pressure of from about 10 to about 200 bara to form an octanol reactor product stream comprising ethanol, water, n-butanol, n-hexanol, n-octanol and hydrogen wherein the selectivity to n-octanol is at least 10% on a carbon basis and wherein the selectivity n-butanol is at least 10% on a carbon basis; and
    fractionating the octanol reactor product stream to form recovered n-hexanol, a n-butanol product stream and a n-octanol product stream.

2. The method of claim 1 further comprising: recovering ethanol from the octanol reactor product stream and recycling at least a portion of the recovered ethanol to the octanol reaction mixture, wherein the source of ethanol comprises at least 50 mole percent of the recovered ethanol; and
    recovering hydrogen from the octanol reactor product stream and recycling at least a portion of recovered hydrogen to the octanol reaction mixture, wherein the source of hydrogen comprises at least 50 mole % recovered hydrogen.

3. The method of claim 1 wherein: the mole ratio of hydrogen to the sum of ethanol and n-hexanol in the octanol reaction mixture is from about 0.1:1 to about 5:1; and the mole ratio of ethanol to n-hexanol in the octanol reaction mixture is from about 1.1:1 to about 2:1.

4. The method of claim 1 wherein the ethanol conversion is from about 20% to about 60%.

5. The method of claim 1 further comprising:
    contacting a butanol reaction mixture comprising a source of ethanol and a source of hydrogen with a Guerbet heterogeneous metal oxide catalyst in a gas phase butanol reactor having a fixed catalyst bed at a reaction temperature of from about 150° C. to 450° C. and at a reaction pressure of from about 10 to about 200 bara to form a butanol reactor product stream comprising ethanol, hydrogen, water, n-butanol and n-hexanol; and fractionating the butanol reactor product stream to form a recovered n-hexanol stream, a n-butanol product stream and recovered ethanol stream, wherein at least a portion of the n-hexanol recovered from the butanol reactor product forms a portion of the source of n-hexanol stream in the octanol reaction mixture.

6. The method of claim 1 wherein the Guerbet catalyst is a metal oxide that comprises (i) at least one bivalent metal selected from the list comprising Mg, Zn, Cu, Co, Mn, Fe, Ni and Ca, (ii) trivalent Ga, and (iii) a noble metal selected from the list comprising Pd, Pt, Ru, Rh and Re.

7. The method of claim 6 wherein the noble metal is Pd.

8. The method of claim 1 wherein the octanol reactor product stream comprises, at standard temperature and pressure:
(1) from about 0.25 to about 0.5 mole fraction ethanol;
(2) from about 0.01 to about 0.08 mole fraction n-butanol;
(3) from about 0.25 to about 0.45 mole fraction n-hexanol; and
(4) from about 0.01 to about 0.08 mole fraction n-octanol.

9. A continuous process for preparing n-butanol and n-octanol, the process comprising:
(a) (1) forming a gas phase n-butanol reaction mixture comprising a source of ethanol and a source of hydrogen, (2) reacting the gas phase n-butanol reaction mixture by contact with a Guerbet heterogeneous metal oxide catalyst in a gas-phase n-butanol reactor at a reaction temperature of from about 150° C. to 450° C. and a reaction pressure of from about 10 to about 200 bara to form a n-butanol reactor product stream comprising n-butanol and n-hexanol and (3) fractionating the n-butanol reactor product stream to form a n-butanol product stream and a recovered n-hexanol stream; and
(b) (1) forming a gas phase n-octanol reaction mixture comprising a source of n-hexanol, a source of ethanol and a source of hydrogen, (2) reacting the gas phase n-octanol reaction mixture by contact with a Guerbet catalyst in a gas phase n-octanol reactor at a reaction temperature of from about 150° C. to 450° C. and a reaction pressure of from about 10 to about 200 bara to form a n-octanol reactor product stream comprising n-octanol, n-butanol and n-hexanol and (3) fractionating the n-octanol reactor product stream to form a n-octanol product stream, a recovered n-hexanol stream and a n-butanol product stream, wherein the source of n-hexanol comprises at least a portion of the n-hexanol stream recovered from the n-butanol reactor product stream.

10. The process of claim 9 wherein:
(a) (1) the n-butanol reactor product stream further comprises ethanol and hydrogen, (2) the process further comprises fractionating the n-butanol reactor product stream to form a recovered ethanol stream and a recovered hydrogen stream and (3) the source of ethanol and the source of hydrogen in the gas phase n-butanol reaction mixture and the source of ethanol and the source of hydrogen in the gas phase n-octanol reaction mixture comprises (i) at least a portion of the recovered ethanol stream formed from the n-butanol reactor product stream and (ii) at least a portion of the recovered hydrogen stream formed from the n-butanol reactor product stream; and
(b) (1) the n-octanol reactor product stream further comprises ethanol and hydrogen, (2) the process further comprises fractionating the n-octanol reactor product stream to form a recovered ethanol stream and a recovered hydrogen stream and (3) the source of ethanol and the source of hydrogen in the gas phase n-butanol reaction mixture and the source of ethanol and the source of hydrogen in the gas phase n-octanol reaction mixture comprises (i) at least a portion of the recovered ethanol stream formed from the n-octanol reactor product stream and (ii) at least a portion of the recovered hydrogen stream formed from the n-octanol reactor product stream.

11. The process of claim 9 wherein:
(a) (1) the n-butanol yield based on ethanol in the n-butanol reaction mixture reaction is from about 10% to about 40% and (2) the selectivity to n-butanol in the n-butanol reaction mixture reaction is from about 65% to about 95%; and
(b) (1) the selectivity to n-butanol in the n-octanol reaction mixture reaction is from about 10% to about 40%, (2) the selectivity to n-octanol in the n-octanol reaction mixture reaction is from about 20% to about 55% and (3) the ethanol conversion in the n-octanol reaction mixture reaction is from about 20% to about 60%.

12. The process of claim 10 wherein: (a) the source of ethanol for the n-butanol reaction mixture and for the n-octanol reaction mixture each comprise at least 50 mole percent recovered ethanol; (b) the source of hydrogen for the n-butanol reaction mixture and for the n-octanol reaction mixture each comprise at least 50 mole percent recovered hydrogen; and (c) the source of n-hexanol for the n-octanol reaction mixture comprises at least 50 mole percent recovered n-hexanol.

13. The process of claim 9 wherein: (a) the mole ratio of ethanol to n-hexanol in the n-octanol reaction mixture is from about 0.3:1 to about 3:1; (b) the mole ratio of hydrogen to ethanol in the n-butanol reactor mixture is from about 0.1:1 to about 5:1; and (c) the mole ratio of hydrogen to the sum of ethanol and n-hexanol in the n-octanol reaction mixture is from about 0.1:1 to about 5:1.

14. The process of claim 9 wherein: (a) the n-butanol reaction mixture further comprises a source of acetaldehyde and the mole ratio of acetaldehyde to ethanol in the n-butanol reaction mixture is from about 0.001:1 to about 0.1:1; (b) the n-butanol product stream further comprises acetaldehyde and the n-butanol reactor product stream is fractionated to recover at least a portion of the acetaldehyde and form a recovered acetaldehyde stream; and (c) at least a portion of the source of acetaldehyde in the n-butanol reaction mixture comprises recovered acetaldehyde.

15. The process of claim 9 wherein the Guerbet catalyst is a metal oxide that comprises (a) at least one bivalent metal selected from the list comprising Mg, Zn, Cu, Co, Mn, Fe, Ni and Ca, (b) trivalent Ga, and (c) a noble metal selected from the list comprising Pd, Pt, Ru, Rh and Re.

16. The process of claim 15 wherein the noble metal is Pd.

17. A facility for manufacturing n-butanol and n-octanol from a source of ethanol and a source of n-hexanol, the facility comprising:
(a) a n-butanol reactor system comprising at least one gas phase reactor having a fixed catalyst bed containing a Guerbet heterogeneous metal oxide catalyst, the reactor comprising (1) an inlet for the input of a n-butanol reactor system feed stream gas comprising a source of ethanol and a source of hydrogen, (2) a reaction zone containing a heterogeneous catalyst for contact with the catalyst to form a n-butanol reactor product stream, and (3) an outlet for the discharge of a n-butanol reactor system product stream, the n-butanol reactor product stream comprising ethanol, water, n-butanol, n-hexanol, and hydrogen, wherein the n-butanol reactor system is operational at a reaction temperature of from about 150° C. to 450° C. and at a reaction pressure of from about 10 to about 200 bara;

(b) a n-octanol reactor system comprising at least one gas phase reactor having a fixed catalyst bed, the reactor comprising (1) an inlet for the input of a n-octanol reactor feed stream gas comprising a source of ethanol, a source of n-hexanol and a source of hydrogen, (2) a reaction zone containing a Guerbet heterogeneous metal oxide catalyst for contact with the reactor feed stream to form a n-octanol reactor product stream, and (3) an outlet for the discharge of the n-octanol reactor product stream, the n-octanol reactor product stream comprising ethanol, water, n-butanol, n-hexanol, n-octanol and hydrogen, wherein the n-octanol reactor system is operational at a reaction temperature of from about 150° C. to 450° C. and at a reaction pressure of from about 10 to about 200 bara;

(c) a first system for fractionating the n-butanol reactor product stream and the n-octanol reactor product stream, wherein the first fractionating system comprises a distillation column or a flash column that forms (1) a first fractionated stream comprising at least 95 mole percent each of the water, the ethanol and the hydrogen contained in the n-butanol reactor product stream and the n-octanol reactor product stream and (2) a second fractionated stream comprising at least 95 mole percent each of the n-butanol, the n-hexanol and the n-octanol contained in the n-butanol reactor stream and the n-octanol reactor product stream;

(d) a second system for fractionating the second fractionated stream, wherein the second fractionating system comprises a distillation column that forms (1) a n-butanol enriched stream comprising at least 95 mole percent of the n-butanol contained in the second fractionated stream and (2) a fourth fractionated stream comprising at least 95 mole percent each of the n-hexanol and the n-octanol contained in the second fractionated stream; and (e) a third system for fractionating the fourth fractionated stream, wherein the third fractionating system comprises a distillation column that forms (1) a recovered n-hexanol stream comprising at least 95 mole percent of the n-hexanol contained in the fourth fractionated stream, wherein the recovered n-hexanol stream is interconnected with the source of n-hexanol for the n-octanol reactor system and at least a portion of the recovered n-hexanol is recycled to the n-octanol reactor feed stream and (2) a n-octanol stream comprising at least 95 mole percent of the n-octanol contained in the fourth fractionated stream.

18. The facility of claim 17 further comprising a system for fractionating the first fractionated stream, wherein the first fractionated stream comprises vapor and the system for fractionating the first fractionated stream comprises a condenser and an ethanol dehydration system wherein (a) the first fractionated stream is passed through the condenser to form a recovered hydrogen gas stream and a wet ethanol condensate stream and (b) the wet ethanol condensate stream is dehydrated to form a recovered ethanol stream and a water stream wherein the recovered ethanol stream comprises at least 95 mole percent of the ethanol and less than 5 mole percent of the water contained in the first fractionated stream, and wherein the recovered ethanol stream and recovered hydrogen stream are interconnected with the source of ethanol and the source of hydrogen for the n-butanol reactor system and the n-octanol reactor system and at least a portion of the recovered ethanol and the recovered hydrogen is recycled to the each of the n-butanol reactor feed stream and the n-octanol reactor feed stream.

19. The facility of claim 17 wherein:

(a) the n-octanol stream is a crude n-octanol stream further comprising n-decanol and wherein the facility further comprises a distillation column for fractionating the crude n-octanol stream to form (1) a n-octanol product stream comprising at least 95 mole percent of the n-octanol contained in crude n-octanol stream and (ii) a n-decanol enriched stream comprising at least 95 mole percent of the n-decanol contained in the crude n-octanol stream;

(b) the n-butanol enriched stream further comprises i-butanol, wherein the facility further comprises a distillation column for fractionating the n-butanol enriched stream to form a n-butanol product stream having a purity in excess of 99 mole percent n-butanol and an impurity stream comprising i-butanol;

(c) the facility further comprises a n-octanol product stream purification distillation column, wherein said distillation column fractionates the n-octanol product stream to form a n-octanol finished product stream having a purity in excess of 99 mole percent n-octanol; and (d) the facility further comprises a n-decanol stream distillation column to fractionate the n-decanol enriched stream form (i) a n-decanol product stream comprising at least 90 mole percent or at least 95 mole percent of the n-decanol contained in the crude n-decanol enriched stream and (ii) a n-decanol stream distillation column bottoms stream enriched in compounds that boil a temperature greater than the boiling point of n-decanol as compared to the n-decanol enriched stream.

20. The facility of claim 17 characterized by the absence of a process output stream comprising in excess of 0.01 mole percent n-hexanol.

\* \* \* \* \*